US006562298B1

(12) United States Patent
Arnquist et al.

(10) Patent No.: US 6,562,298 B1
(45) Date of Patent: May 13, 2003

(54) STRUCTURE FOR DETERMINATION OF ITEM OF INTEREST IN A SAMPLE

(75) Inventors: David C. Arnquist, The Colony, TX (US); Grady Barnes, III, Grayslake, IL (US); Richard D. Button, Richardson, TX (US); Chadwick M. Dunn, McHenry, IL (US); Richard C. East, Jr., Dallas, TX (US); Patrick P. Fritchie, Southlake, TX (US); Charles M. Galitz, Kenosha, WI (US); Gregory E. Gardner, Euless, TX (US); Cass J. Grandone, Southlake, TX (US); Robert C. Gray, Gurnee, IL (US); James T. Holen, Mundelein, IL (US); Robert P. Luoma, II, Highland Village, TX (US); Jimmy D. McCoy, Keller, TX (US); James E. Mitchell, Windham, NH (US); Adrian John Murray, Arlington Heights, IL (US); David W. Murray, Allen, TX (US); Jack F. Ramsey, Grayslake, IL (US); Neal T. Sleszynski, Kenosha, WI (US); Julius J. Toth, Mundelein, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/298,711

(22) Filed: Apr. 23, 1999

Related U.S. Application Data

(62) Division of application No. 09/140,607, filed on Aug. 26, 1998, which is a division of application No. 08/715,780, filed on Sep. 19, 1996, now Pat. No. 5,856,194.

(51) Int. Cl.$^7$ .................. G01N 35/04; B65G 47/22
(52) U.S. Cl. .............. 422/63; 422/64; 422/67; 422/68.1; 422/82.05; 436/47; 436/48; 436/49; 436/50; 198/347.4; 198/348; 198/357
(58) Field of Search .................. 422/63, 64, 65, 422/67, 68.1, 82.05; 436/47, 48, 49, 50; 198/348, 357, 347.4

(56) References Cited

U.S. PATENT DOCUMENTS 893,469 A 7/1908 Essmuller (List continued on next page.)

FOREIGN PATENT DOCUMENTS

CA 2058175 12/1990

(List continued on next page.)

OTHER PUBLICATIONS

Luninescent Labels for Immunoassay From Concept to Practice; F. McCapra et al., Journal of Bioluminescence and Chemiliminescence vol. 4 51–58 1989.

(List continued on next page.)

*Primary Examiner*—Jill Warden
*Assistant Examiner*—Kathryn Bex
(74) *Attorney, Agent, or Firm*—David L. Weinstein

(57) ABSTRACT

The embodiments disclosed relate to determination of an item of interest in a sample. One embodiment relates to a structure which comprises a process path. The process path comprises a process lane including a process step performance lane where a process step is performed, and a process step avoidance lane where the process step is avoided. A first prime mover is operatively connected with the process path for moving a container holding the sample along the process path. A first pipetting system is operatively associated with the process path for introducing the sample to the container. A second pipetting system is operatively associated with the process path for introducing a reagent to the container. A device is operatively connected with the process path and is selectively engagable with the container for mixing the sample and the reagent in the container. A second prime mover is operatively connected with the process path for selectively positioning the container in a selected one of the process step performance lane and the process step avoidance lane. A reader is operatively connected with the process path for determining the item of interest in the sample based upon a reaction between the sample and the reagent.

19 Claims, 30 Drawing Sheets

U.S. PATENT DOCUMENTS

| | | | |
|---|---|---|---|
| 1,180,665 A | 4/1916 | McElroy | 215/247 |
| 2,587,221 A | 2/1952 | Richardson et al. | 23/230 |
| 2,837,092 A | 6/1958 | Scholler et al. | 128/218 |
| 2,906,423 A | 9/1959 | Sandhage | 215/47 |
| 2,948,940 A | 8/1960 | Degener | 24/257 |
| 2,955,722 A | 10/1960 | Antonious | 215/100.5 |
| 3,019,932 A | 2/1962 | Singiser | 215/37 |
| 3,038,340 A | 6/1962 | Isreeli | 73/423 |
| 3,085,705 A | 4/1963 | Varney | 215/41 |
| 3,107,537 A | 10/1963 | Isreeli et al. | 73/423 |
| 3,178,266 A | 4/1965 | Anthon | 23/253 |
| 3,190,731 A | 6/1965 | Weiskoff | 23/292 |
| 3,192,968 A | 7/1965 | Baruch et al. | 141/82 |
| 3,193,358 A | 7/1965 | Baruch | 23/253 |
| 3,223,269 A | 12/1965 | Williams | 215/43 |
| 3,272,240 A | 9/1966 | Roth | 141/176 |
| 3,302,772 A | 2/1967 | Alsop | 198/221 |
| 3,307,371 A | 3/1967 | Andros | 62/234 |
| 3,317,069 A | 5/1967 | Chin | 215/47 |
| 3,399,116 A | 8/1968 | Du Bois et al. | 196/98 |
| 3,457,048 A | 7/1969 | Stephens et al. | 23/272.6 |
| 3,489,521 A | 1/1970 | Buckle et al. | 23/253 |
| 3,489,525 A | 1/1970 | Natelson | 23/253 |
| 3,533,744 A | 10/1970 | Unger | 23/230 |
| 3,555,143 A | 1/1971 | Axen et al. | 424/1 |
| 3,578,291 A | 5/1971 | Oberil | 259/75 |
| 3,594,129 A | 7/1971 | Jones | 23/253 |
| 3,606,074 A | 9/1971 | Hayes | 220/42 |
| 3,607,094 A | 9/1971 | Beer | 23/253 |
| 3,607,098 A | 9/1971 | Strande | 23/259 |
| 3,609,040 A | 9/1971 | Kuzel et al. | 356/36 |
| 3,614,434 A | 10/1971 | Horwitz et al. | 250/71.5 |
| 3,615,230 A | 10/1971 | Barnick et al. | 23/253 |
| 3,616,264 A | 10/1971 | Ray et al. | 195/127 |
| 3,617,222 A | 11/1971 | Matte | 23/230 |
| 3,621,203 A | 11/1971 | Geominy et al. | 219/528 |
| 3,633,768 A | 1/1972 | Gulgen | 214/8.5 |
| 3,634,651 A | 1/1972 | Siegel | 219/400 |
| 3,635,094 A | 1/1972 | Oberli | 73/423 |
| 3,638,507 A | 2/1972 | Orner | 74/424 |
| 3,643,812 A | 2/1972 | Mander et al. | 211/74 |
| 3,644,095 A | 2/1972 | Netheler et al. | 23/259 |
| 3,652,761 A | 3/1972 | Woetail | 424/12 |
| 3,653,528 A | 4/1972 | Wimmer | 215/38 |
| 3,654,090 A | 4/1972 | Wilhelmus | 195/103 |
| 3,655,089 A | 4/1972 | Tower | 220/42 |
| 3,658,478 A | 4/1972 | Spergel et al. | 23/253 |
| 3,673,886 A | 7/1972 | Tomita et al. | 74/424 |
| 3,676,080 A | 7/1972 | Richterich | 23/253 |
| 3,676,679 A | 7/1972 | Waters | 250/83 |
| 3,687,632 A | 8/1972 | Natelson | 23/259 |
| 3,702,612 A | 11/1972 | Schlesinger | 128/350 |
| 3,708,264 A | 1/1973 | Jottier | 23/230 |
| 3,720,116 A | 3/1973 | Better et al. | 74/459 |
| 3,722,312 A | 3/1973 | Better et al. | 74/459 |
| 3,723,066 A | 3/1973 | Moran | 23/253 |
| 3,727,029 A | 4/1973 | Chrow | 219/301 |
| 3,728,079 A | 4/1973 | Moran | 23/253 |
| 3,746,514 A | 7/1973 | Colvin et al. | 23/253 |
| 3,753,657 A | 8/1973 | Downing et al. | 23/253 |
| 3,764,268 A | 10/1973 | Kosowsky et al. | 23/253 |
| 3,765,237 A | 10/1973 | Blackmer et al. | 73/190 |
| 3,767,364 A | 10/1973 | Ritchie et al. | 23/259 |
| 3,770,382 A | 11/1973 | Carter et al. | 23/253 |
| 3,784,785 A | 1/1974 | Noland | 219/301 |
| 3,790,346 A | 2/1974 | Ritchie | 23/253 |
| 3,791,537 A | 2/1974 | Conklin | 214/6.5 |
| 3,796,544 A | 3/1974 | Zauft et al. | 23/259 |
| 3,806,321 A | 4/1974 | Durrum et al. | 23/253 |
| 3,807,457 A | 4/1974 | Logsdon | 138/89 |
| 3,807,955 A | 4/1974 | Note, Jr. et al. | 23/230 |
| 3,811,842 A | 5/1974 | Diebler et al. | 23/259 |
| 3,813,215 A | 5/1974 | Ward | 432/226 |
| 3,823,840 A | 7/1974 | Zackheim | 215/37 |
| 3,826,397 A | 7/1974 | Atkins | 215/41 |
| 3,826,621 A | 7/1974 | Johnson, Jr. et al. | 23/259 |
| 3,830,108 A | 8/1974 | Spong | 73/425.6 |
| 3,843,323 A | 10/1974 | Quame | 23/230 |
| 3,850,174 A | 11/1974 | Ayres | 128/272 |
| 3,850,341 A | 11/1974 | Bart | 220/212 |
| 3,850,580 A | 11/1974 | Moore et al. | 23/259 |
| 3,851,541 A | 12/1974 | Ploss et al. | 74/459 |
| 3,854,879 A | 12/1974 | Figueroa et al. | 23/230 |
| 3,868,493 A | 2/1975 | Caroleo | 219/318 |
| 3,883,305 A | 5/1975 | Hoskins et al. | 23/253 |
| 3,883,306 A | 5/1975 | Widen | 23/253 |
| 3,894,706 A | 7/1975 | Mizusawa | 248/68 |
| 3,897,216 A | 7/1975 | Jones | 23/259 |
| 3,900,289 A | 8/1975 | Liston | 23/230 |
| 3,912,456 A | 10/1975 | Young | 23/253 |
| 3,917,455 A | 11/1975 | Bak et al. | 23/253 |
| 3,933,997 A | 1/1976 | Hersh et al. | 424/1 |
| 3,948,607 A | 4/1976 | Atwood et al. | 23/259 |
| 3,949,189 A | 4/1976 | Bilbro et al. | 219/301 |
| 3,951,605 A | 4/1976 | Natelson | 23/253 |
| 3,970,518 A | 7/1976 | Giaever | 195/1.5 |
| 3,977,551 A | 8/1976 | Ciarico | 215/1 |
| 3,980,268 A | 9/1976 | Ellis | 249/49 |
| 3,981,776 A | 9/1976 | Saxholm | 195/103 |
| 3,985,508 A | 10/1976 | Williams | 23/253 |
| 4,000,252 A | 12/1976 | Kosak | 424/1 |
| 4,000,973 A | 1/1977 | Petesen | 23/230 |
| 4,000,974 A | 1/1977 | Acord | 23/230 |
| 4,002,532 A | 1/1977 | Weltman et al. | 195/103 |
| 4,004,883 A | 1/1977 | Meyer et al. | 23/259 |
| RE29,169 E | 4/1977 | Schuurs et al. | 195/103.5 |
| 4,016,043 A | 4/1977 | Schuurs et al. | 195/103 |
| 4,018,886 A | 4/1977 | Giaever | 424/12 |
| 4,022,579 A | 5/1977 | Revillet et al. | 23/259 |
| 4,034,071 A | 7/1977 | Strickler | 424/1 |
| 4,039,287 A | 8/1977 | Moran | 23/253 |
| 4,039,652 A | 8/1977 | Adams et al. | 424/1 |
| 4,040,533 A | 8/1977 | De Boer et al. | 214/310 |
| 4,041,146 A | 8/1977 | Giaever | 424/1 |
| 4,045,179 A | 8/1977 | Bunce | 23/259 |
| 4,046,248 A | 9/1977 | Goffredo et al. | 198/583 |
| 4,047,034 A | 9/1977 | Auphan | 250/354 |
| 4,054,416 A | 10/1977 | Duff | 23/259 |
| 4,058,367 A | 11/1977 | Gilford | 23/253 |
| 4,065,358 A | 12/1977 | Kawai et al. | 195/127 |
| 4,066,412 A | 1/1978 | Johnson et al. | 23/253 |
| 4,067,694 A | 1/1978 | Blakely et al. | |
| 4,077,444 A | 3/1978 | Gilson et al. | 141/130 |
| 4,077,804 A | 3/1978 | Vanzo | 96/1 |
| 4,078,971 A | 3/1978 | Arkles et al. | 195/63 |
| 4,080,833 A | 3/1978 | Huber | 73/423 |
| 4,081,245 A | 3/1978 | Polito | 23/230 |
| 4,081,246 A | 3/1978 | Polito et al. | 23/230 |
| 4,094,641 A | 6/1978 | Friswell | 23/230 |
| 4,098,876 A | 7/1978 | Plasie et al. | 424/1 |
| 4,104,029 A | 8/1978 | Maier, Jr. | 23/230 |
| 4,106,907 A | 8/1978 | Charlton et al. | 23/230 |
| 4,108,972 A | 8/1978 | Dreyer | 424/1 |
| 4,112,517 A | 9/1978 | Giombini | 366/102 |
| 4,113,383 A | 9/1978 | Burns et al. | 356/36 |
| 4,113,436 A | 9/1978 | Werder et al. | 422/65 |
| 4,115,534 A | 9/1978 | Ithakissios | 424/1 |
| 4,115,535 A | 9/1978 | Giaever | 424/1 |
| 4,115,861 A | 9/1978 | Allington | 364/497 |
| 4,118,280 A | 10/1978 | Charles et al. | 195/127 |
| 4,118,801 A | 10/1978 | Kraft et al. | 366/111 |

| | | | | | | |
|---|---|---|---|---|---|---|
| 4,119,709 A | 10/1978 | Holub .......................... 424/1 | | 4,267,234 A | 5/1981 | Rembaum .................. 428/403 |
| 4,120,662 A | 10/1978 | Fosslien ...................... 73/425 | | 4,267,235 A | 5/1981 | Rembaum .................. 428/407 |
| 4,123,121 A | 10/1978 | Ernst et al. .................... 308/6 | | 4,268,477 A | 5/1981 | Herzstark .................... 422/64 |
| 4,125,492 A | 11/1978 | Cuatrecasas et al. ........... 260/9 | | 4,272,482 A | 6/1981 | Jessop et al. ................. 422/65 |
| 4,131,788 A | 12/1978 | Fulbrook ................... 219/535 | | 4,272,506 A | 6/1981 | Schwarzberg ................ 424/8 |
| RE29,880 E | 1/1979 | Duff ........................... 422/64 | | 4,272,510 A | 6/1981 | Smith et al. ................. 427/47 |
| 4,133,873 A | 1/1979 | Noller .......................... 424/8 | | 4,276,051 A | 6/1981 | Ginsberg et al. ............ 23/230 |
| 4,134,512 A | 1/1979 | Nugent ...................... 215/247 | | 4,276,258 A | 6/1981 | Ginsberg et al. ............ 422/64 |
| 4,137,216 A | 1/1979 | Lemper et al. .............. 260/42 | | 4,277,440 A | 7/1981 | Jessop et al. ............... 422/100 |
| 4,139,242 A | 2/1979 | Ernst ........................... 308/6 | | 4,278,437 A | 7/1981 | Haggar ........................ 23/230 |
| 4,139,604 A | 2/1979 | Gutcho et al. ................. 424/1 | | 4,279,992 A | 7/1981 | Boguslaski et al. ............ 435/7 |
| 4,140,020 A | 2/1979 | Cook .......................... 73/425 | | 4,281,387 A | 7/1981 | Kraft et al. .................. 364/497 |
| 4,141,524 A | 2/1979 | Corvese, Jr. .................. 248/70 | | RE30,730 E | 9/1981 | Duff ............................ 422/64 |
| 4,141,687 A | 2/1979 | Forrest et al. ................ 23/230 | | 4,292,920 A | 10/1981 | Smith et al. ................. 118/425 |
| 4,147,250 A | 4/1979 | Schulz ....................... 198/472 | | 4,294,078 A | 10/1981 | Percarpio et al. ........... 215/247 |
| 4,151,931 A | 5/1979 | Scherer et al. ............... 221/226 | | 4,294,799 A | 10/1981 | Stephens et al. ............. 422/62 |
| 4,152,210 A | 5/1979 | Robinson et al. .............. 195/63 | | 4,295,572 A | 10/1981 | Percarpio ................... 215/247 |
| 4,152,269 A | 5/1979 | Babson ...................... 210/516 | | 4,297,337 A | 10/1981 | Mansfield et al. ............. 424/1 |
| 4,152,577 A | 5/1979 | Leavines .................... 219/301 | | 4,298,593 A | 11/1981 | Ling ............................ 424/1 |
| 4,155,978 A | 5/1979 | Naono et al. ................. 422/64 | | 4,298,687 A | 11/1981 | Maes ........................... 435/7 |
| 4,157,323 A | 6/1979 | Yen et al. ..................... 260/29 | | 4,302,534 A | 11/1981 | Halmann et al. .............. 435/6 |
| 4,160,165 A | 7/1979 | McCombs et al. ........... 250/354 | | 4,305,668 A | 12/1981 | Bilbrey ....................... 366/111 |
| 4,166,095 A | 8/1979 | Kling et al. ................... 422/67 | | 4,305,924 A | 12/1981 | Piasio et al. .................. 424/1 |
| 4,166,104 A | 8/1979 | Wagner et al. ................. 424/1 | | 4,307,766 A | 12/1981 | Tanokura ...................... 150/8 |
| 4,168,955 A | 9/1979 | Allington ..................... 23/230 | | 4,311,348 A | 1/1982 | Olschewski et al. ........... 308/6 |
| 4,169,138 A | 9/1979 | Jonsson ....................... 424/12 | | 4,311,667 A | 1/1982 | Gocho ......................... 422/64 |
| 4,169,804 A | 10/1979 | Yapel et al. .................. 252/62 | | 4,312,835 A | 1/1982 | Zoltan et al. ................. 422/70 |
| 4,177,253 A | 12/1979 | Davies et al. .................. 424/1 | | 4,313,734 A | 2/1982 | Leuvering ................... 23/230 |
| 4,185,084 A | 1/1980 | Mochida et al. ................ 424/1 | | 4,313,735 A | 2/1982 | Yamashita et al. ........... 23/230 |
| 4,187,075 A | 2/1980 | Noller ......................... 23/230 | | 4,315,891 A | 2/1982 | Sakurada ..................... 422/64 |
| 4,191,287 A | 3/1980 | Brook et al. ................. 198/472 | | 4,315,907 A | 2/1982 | Fridlender et al. ............. 424/1 |
| 4,192,845 A | 3/1980 | Kalasek ....................... 422/25 | | 4,318,707 A | 3/1982 | Litman et al. ............... 23/230 |
| 4,193,866 A | 3/1980 | Slusarczuk et al. ............ 210/6 | | 4,318,884 A | 3/1982 | Suzuki ......................... 422/63 |
| 4,200,436 A | 4/1980 | Mochida et al. .............. 23/230 | | 4,318,980 A | 3/1982 | Boguslaski et al. ............ 435/7 |
| 4,202,634 A | 5/1980 | Kraft et al. .................. 366/111 | | 4,320,109 A | 3/1982 | Wolf et al. .................... 424/1 |
| 4,205,885 A | 6/1980 | Ernst et al. .................... 308/6 | | 4,322,216 A | 3/1982 | Lillig et al. .................. 23/230 |
| 4,206,094 A | 6/1980 | Yen et al. ....................... 260/8 | | 4,325,909 A | 4/1982 | Coulter et al. ................ 422/63 |
| 4,206,951 A | 6/1980 | Ernst et al. .................... 308/6 | | 4,325,910 A | 4/1982 | Jordan ......................... 422/64 |
| 4,207,289 A | 6/1980 | Weiss ........................ 422/104 | | 4,330,299 A | 5/1982 | Cerami ....................... 23/230 |
| 4,208,484 A | 6/1980 | Sogi et al. ................... 435/286 | | 4,332,471 A | 6/1982 | Gross ......................... 356/246 |
| 4,213,999 A | 7/1980 | Witiak et al. ................ 424/285 | | 4,332,783 A | 6/1982 | Pernice et al. ................. 424/1 |
| 4,218,539 A | 8/1980 | Weltman .................... 435/188 | | 4,333,356 A | 6/1982 | Bartels et al. ................ 73/864 |
| 4,228,237 A | 10/1980 | Hevey et al. ................... 435/7 | | 4,335,620 A | 6/1982 | Adams ........................ 73/863 |
| 4,229,104 A | 10/1980 | Lahme et al. ............... 356/246 | | 4,335,730 A | 6/1982 | Griffin ....................... 128/760 |
| 4,230,685 A | 10/1980 | Senyei et al. ................. 424/12 | | 4,341,736 A | 7/1982 | Drbal et al. ................. 422/100 |
| 4,230,797 A | 10/1980 | Bogulaski et al. .............. 435/7 | | 4,343,766 A | 8/1982 | Sisti et al. .................... 422/63 |
| 4,231,750 A | 11/1980 | Dowben et al. .............. 23/230 | | 4,343,901 A | 8/1982 | DeFilippi ................... 435/176 |
| 4,232,119 A | 11/1980 | Carlsson et al. ................ 435/7 | | 4,345,843 A | 8/1982 | Berglund et al. ............ 366/219 |
| 4,234,538 A | 11/1980 | Ginsberg et al. ............. 422/64 | | 4,346,056 A | 8/1982 | Sakurada ..................... 422/64 |
| 4,234,540 A | 11/1980 | Ginsberg et al. ............. 422/64 | | 4,346,742 A | 8/1982 | Chase et al. ................... 141/1 |
| 4,235,869 A | 11/1980 | Schwarzberg ................ 424/8 | | 4,349,510 A | 9/1982 | Kolehmainen et al. ....... 422/66 |
| 4,235,960 A | 11/1980 | Sasse et al. .................... 435/7 | | 4,351,800 A | 9/1982 | Kopp et al. .................. 422/70 |
| 4,238,195 A | 12/1980 | Boguslaski et al. ........... 23/230 | | 4,355,165 A | 10/1982 | Boguslaski et al. ......... 544/237 |
| 4,239,298 A | 12/1980 | Ernst et al. .................... 308/6 | | 4,356,722 A | 11/1982 | Bunce et al. .................. 73/53 |
| 4,241,176 A | 12/1980 | Avrameas et al. .............. 435/7 | | 4,356,967 A | 11/1982 | Lunick ........................ 237/14 |
| 4,244,459 A | 1/1981 | Garrett ....................... 198/389 | | 4,357,301 A | 11/1982 | Cassaday et al. ............. 422/64 |
| 4,244,920 A | 1/1981 | Manschot et al. ........... 422/102 | | 4,362,531 A | 12/1982 | de Steenwinkel et al. .... 23/230 |
| 4,250,400 A | 2/1981 | Lee ........................... 219/549 | | 4,363,759 A | 12/1982 | Boguslaski et al. ......... 260/112 |
| 4,254,460 A | 3/1981 | Achter et al. ................ 364/104 | | 4,363,781 A | 12/1982 | Akamatsu et al. ............ 422/65 |
| 4,256,106 A | 3/1981 | Shoor ........................ 128/247 | | 4,366,118 A | 12/1982 | Bunce et al. ................. 422/57 |
| 4,256,725 A | 3/1981 | Rutner et al. .................. 424/1 | | 4,366,119 A | 12/1982 | Takeuchi ..................... 422/65 |
| 4,256,960 A | 3/1981 | Snider ........................ 250/252 | | 4,369,226 A | 1/1983 | Rembaum .................. 428/334 |
| 4,257,884 A | 3/1981 | Lim ........................... 210/656 | | 4,372,745 A | 2/1983 | Mandle et al. .............. 436/537 |
| 4,259,288 A | 3/1981 | Welch ........................ 422/63 | | 4,373,925 A | 2/1983 | Litman et al. ................. 435/7 |
| 4,259,289 A | 3/1981 | Curry et al. .................. 422/64 | | 4,373,931 A | 2/1983 | Takekawa .................. 436/539 |
| 4,259,291 A | 3/1981 | Smythe ....................... 422/82 | | 4,376,110 A | 3/1983 | David et al. ................ 436/513 |
| 4,261,893 A | 4/1981 | Boguslaski et al. .......... 260/326 | | 4,380,580 A | 4/1983 | Boguslaski et al. ............ 435/7 |
| RE30,627 E | 5/1981 | Bagshawe et al. ............ 23/230 | | 4,383,031 A | 5/1983 | Boguslaski et al. ............ 435/7 |
| 4,265,855 A | 5/1981 | Mandle et al. .............. 422/654 | | 4,385,126 A | 5/1983 | Chen et al. ................. 436/518 |
| 4,266,651 A | 5/1981 | Strom ........................ 198/345 | | 4,397,385 A | 8/1983 | Booth et al. ................ 198/345 |
| 4,267,149 A | 5/1981 | Bruckner et al. ............. 422/65 | | 4,402,909 A | 9/1983 | Solazzi ........................ 422/50 |

| Patent | Date | Inventor | Class |
|---|---|---|---|
| 4,403,040 A | 9/1983 | Van Aken | 436/501 |
| 4,407,943 A | 10/1983 | Cole et al. | 435/7 |
| 4,407,964 A | 10/1983 | Elings et al. | 436/518 |
| 4,414,324 A | 11/1983 | Stout | 435/7 |
| 4,415,700 A | 11/1983 | Batz et al. | 524/548 |
| 4,418,846 A | 12/1983 | Pong et al. | 222/189 |
| 4,419,734 A | 12/1983 | Wolfson et al. | 365/567 |
| 4,421,860 A | 12/1983 | Elings et al. | 436/518 |
| 4,433,059 A | 2/1984 | Chang et al. | 436/512 |
| 4,433,060 A | 2/1984 | Frenzel | 436/518 |
| 4,435,509 A | 3/1984 | Berthold et al. | 436/518 |
| 4,437,762 A | 3/1984 | Glenn et al. | 356/326 |
| 4,438,068 A | 3/1984 | Forrest | 422/61 |
| 4,438,986 A | 3/1984 | Teramachi | 308/6 |
| 4,451,433 A | 5/1984 | Yamashita et al. | 422/63 |
| 4,454,226 A | 6/1984 | Ali et al. | 435/7 |
| 4,454,234 A | 6/1984 | Czerlinski | 436/526 |
| 4,454,939 A | 6/1984 | Kampf et al. | 198/341 |
| 4,455,280 A | 6/1984 | Shinohara et al. | 422/63 |
| 4,456,037 A | 6/1984 | Gocho | 141/1 |
| 4,459,265 A | 7/1984 | Berglund | 422/64 |
| 4,459,359 A | 7/1984 | Neurath | 436/54 |
| 4,472,352 A | 9/1984 | Quesneau et al. | 422/52 |
| 4,477,576 A | 10/1984 | Deutsch et al. | 436/500 |
| 4,477,578 A | 10/1984 | Miles et al. | 436/518 |
| 4,478,817 A | 10/1984 | Campbell et al. | 424/7 |
| 4,482,636 A | 11/1984 | Mochida et al. | 436/518 |
| 4,483,823 A | 11/1984 | Umetsu et al. | 422/63 |
| 4,483,927 A | 11/1984 | Takekawa | 436/43 |
| 4,484,061 A | 11/1984 | Zelinka et al. | 219/301 |
| 4,484,815 A | 11/1984 | Akiyama | 356/325 |
| 4,488,633 A | 12/1984 | Kampf | 198/472 |
| 4,491,634 A | 1/1985 | Frenzel | 436/518 |
| 4,492,751 A | 1/1985 | Boguslaski et al. | 435/7 |
| 4,495,295 A | 1/1985 | Neurath | 436/518 |
| 4,495,296 A | 1/1985 | Neurath et al. | 436/530 |
| 4,497,774 A | 2/1985 | Scordato | 422/73 |
| D278,182 S | 3/1985 | Aihara et al. | D24/29 |
| 4,504,585 A | 3/1985 | Reynolds | 436/518 |
| 4,506,009 A | 3/1985 | Lenhoff et al. | 435/7 |
| 4,506,777 A | 3/1985 | Kampf | 198/341 |
| 4,515,752 A | 5/1985 | Miramanda | 422/99 |
| 4,517,160 A | 5/1985 | Galle et al. | 422/65 |
| 4,517,288 A | 5/1985 | Giegel et al. | 435/7 |
| 4,517,460 A | 5/1985 | Meulenbrugge et al. | 250/252 |
| 4,517,851 A | 5/1985 | Tice | 73/864 |
| 4,522,921 A | 6/1985 | Ogawa | 436/65 |
| 4,523,295 A | 6/1985 | Zato | 364/900 |
| 4,523,862 A | 6/1985 | Yasui et al. | 384/564 |
| 4,523,864 A | 6/1985 | Walter et al. | 384/613 |
| 4,528,159 A | 7/1985 | Liston | 422/65 |
| 4,533,255 A | 8/1985 | Gronholz et al. | 366/108 |
| 4,533,629 A | 8/1985 | Litman et al. | 435/7 |
| 4,534,465 A | 8/1985 | Rothermel et al. | 206/443 |
| 4,536,369 A | 8/1985 | Sakurada et al. | 422/65 |
| 4,537,510 A | 8/1985 | Takahasi | 356/435 |
| 4,537,861 A | 8/1985 | Elings et al. | 436/518 |
| 4,540,660 A | 9/1985 | Harte et al. | 435/7 |
| 4,541,291 A | 9/1985 | Churchill et al. | 73/864 |
| 4,542,661 A | 9/1985 | Teramachi | 74/424 |
| 4,542,833 A | 9/1985 | DeVaughn | 215/319 |
| 4,545,497 A | 10/1985 | Martha, Jr. | 215/253 |
| 4,551,426 A | 11/1985 | Freytag et al. | 435/7 |
| 4,551,619 A | 11/1985 | Lefebvre | 219/523 |
| 4,552,812 A | 11/1985 | Margel et al. | 428/407 |
| 4,552,839 A | 11/1985 | Gould et al. | 435/7 |
| 4,554,088 A | 11/1985 | Whitehead et al. | 252/62 |
| 4,555,183 A | 11/1985 | Thomas | 366/208 |
| 4,559,120 A | 12/1985 | Royse et al. | 204/182 |
| 4,560,269 A | 12/1985 | Baldszun et al. | 356/246 |
| 4,561,820 A | 12/1985 | Matheny, III et al. | 414/331 |
| 4,576,912 A | 3/1986 | Yaverbaum et al. | 435/7 |
| 4,578,244 A | 3/1986 | Cosgrove, Jr. et al. | 422/65 |
| 4,581,521 A | 4/1986 | Grise | 219/535 |
| 4,583,668 A | 4/1986 | Maynard, Jr. | 222/529 |
| 4,584,277 A | 4/1986 | Ullman | 436/501 |
| D283,728 S | 5/1986 | Aihara | D24/29 |
| 4,588,697 A | 5/1986 | Khanna et al. | 436/518 |
| 4,595,562 A | 6/1986 | Liston et al. | 422/65 |
| 4,604,348 A | 8/1986 | Neurath | 435/7 |
| 4,610,546 A | 9/1986 | Intraub | 366/110 |
| 4,613,567 A | 9/1986 | Yasoshima et al. | 435/7 |
| 4,615,360 A | 10/1986 | Jacobs | 141/18 |
| 4,623,621 A | 11/1986 | Pestka | 435/7 |
| 4,623,629 A | 11/1986 | Kerschensteiner | 436/518 |
| 4,628,037 A | 12/1986 | Chagnon et al. | 436/526 |
| 4,629,688 A | 12/1986 | Bolguslaski et al. | 435/7 |
| 4,629,690 A | 12/1986 | Weng et al. | 435/7 |
| 4,629,703 A | 12/1986 | Uffenheimer | 436/45 |
| 4,634,575 A | 1/1987 | Kawakami et al. | 422/63 |
| 4,634,576 A | 1/1987 | Galle et al. | 422/102 |
| 4,637,985 A | 1/1987 | Sidki et al. | 436/518 |
| 4,639,135 A | 1/1987 | Borer et al. | 356/246 |
| 4,639,425 A | 1/1987 | Baier | 436/518 |
| 4,639,875 A | 1/1987 | Abraham et al. | 364/479 |
| 4,643,879 A | 2/1987 | Hanaway | 422/104 |
| 4,645,646 A | 2/1987 | Gadow et al. | 422/61 |
| 4,645,747 A | 2/1987 | Cais et al. | 436/500 |
| D288,845 S | 3/1987 | Borer et al. | D24/29 |
| 4,647,432 A | 3/1987 | Wakatake | 422/64 |
| 4,649,116 A | 3/1987 | Daty et al. | 435/287 |
| 4,651,813 A | 3/1987 | Witt et al. | 165/30 |
| 4,652,519 A | 3/1987 | Warshawsky et al. | 435/7 |
| 4,652,533 A | 3/1987 | Jolley | 436/518 |
| 4,654,299 A | 3/1987 | Lentfer | 435/7 |
| 4,654,300 A | 3/1987 | Zuk et al. | 435/7 |
| 4,657,851 A | 4/1987 | Feller et al. | 435/7 |
| 4,659,678 A | 4/1987 | Forrest et al. | 436/512 |
| 4,661,444 A | 4/1987 | Li | 435/7 |
| 4,661,498 A | 4/1987 | Lau et al. | 428/405 |
| 4,663,277 A | 5/1987 | Wang | 435/5 |
| 4,666,866 A | 5/1987 | Krauth | 436/518 |
| 4,668,617 A | 5/1987 | Furuta et al. | 435/4 |
| 4,670,219 A | 6/1987 | Nelson et al. | 422/63 |
| 4,670,381 A | 6/1987 | Frickey et al. | 435/7 |
| 4,670,383 A | 6/1987 | Baier et al. | 435/7 |
| 4,672,040 A | 6/1987 | Josephson | 436/526 |
| 4,676,656 A | 6/1987 | Cook et al. | 366/142 |
| 4,676,951 A | 6/1987 | Armes et al. | 422/65 |
| 4,678,752 A | 7/1987 | Thorne et al. | 435/291 |
| 4,680,275 A | 7/1987 | Wagner et al. | 436/518 |
| 4,681,741 A | 7/1987 | Hanaway | 422/100 |
| 4,687,638 A | 8/1987 | Benajam | 422/73 |
| 4,689,305 A | 8/1987 | Stiffey et al. | 435/291 |
| 4,693,969 A | 9/1987 | Saxena et al. | 435/7 |
| 4,693,970 A | 9/1987 | O'Connell et al. | 435/7 |
| 4,695,392 A | 9/1987 | Whitehead et al. | 252/62 |
| 4,695,393 A | 9/1987 | Whitehead et al. | 252/62 |
| 4,698,302 A | 10/1987 | Whitehead et al. | 435/94 |
| 4,699,797 A | 10/1987 | Aihara | 422/65 |
| 4,706,736 A | 11/1987 | Gyori | 165/30 |
| 4,708,886 A | 11/1987 | Nelson | 422/72 |
| 4,710,472 A | 12/1987 | Saur et al. | 435/287 |
| 4,711,839 A | 12/1987 | Singhal | 435/4 |
| 4,713,974 A | 12/1987 | Stone | 73/864 |
| 4,731,225 A | 3/1988 | Wakatake | 422/65 |
| 4,731,337 A | 3/1988 | Luotola et al. | 436/526 |
| 4,732,811 A | 3/1988 | Margel | 428/403 |
| 4,737,342 A | 4/1988 | Herrmann et al. | 422/64 |
| 4,737,453 A | 4/1988 | Primus | 435/5 |
| 4,738,825 A | 4/1988 | Kelln | 422/72 |
| 4,740,457 A | 4/1988 | Parratt | 435/7 |

| Patent No. | | Date | Inventor | Class |
|---|---|---|---|---|
| 4,743,536 | A | 5/1988 | Evanega et al. | 435/7 |
| 4,743,544 | A | 5/1988 | Namba et al. | 435/7 |
| 4,743,560 | A | 5/1988 | Campbell et al. | 436/501 |
| 4,745,077 | A | 5/1988 | Holian et al. | 436/526 |
| 4,747,693 | A | 5/1988 | Kahl | 366/208 |
| 4,753,775 | A | 6/1988 | Ebersole et al. | 422/81 |
| 4,754,414 | A | 6/1988 | Gocho | 364/497 |
| 4,755,055 | A | 7/1988 | Johnson et al. | 356/440 |
| 4,755,356 | A | 7/1988 | Robbins et al. | 422/102 |
| 4,758,523 | A | 7/1988 | Harjunmaa | 436/531 |
| 4,761,268 | A | 8/1988 | Andersen et al. | 422/72 |
| 4,761,379 | A | 8/1988 | Williams et al. | 435/296 |
| 4,763,803 | A | 8/1988 | Schneider | 215/260 |
| 4,764,342 | A | 8/1988 | Kelln et al. | 422/72 |
| 4,771,429 | A | 9/1988 | Davis et al. | 371/27 |
| 4,772,453 | A | 9/1988 | Lisenbee | 422/52 |
| 4,772,550 | A | 9/1988 | Greenquist | 435/7 |
| 4,774,055 | A | 9/1988 | Wakatake et al. | 422/64 |
| 4,774,174 | A | 9/1988 | Giegel et al. | 435/5 |
| 4,774,191 | A | 9/1988 | Khanna et al. | 436/518 |
| 4,775,635 | A | 10/1988 | Ebersole et al. | 436/501 |
| 4,775,636 | A | 10/1988 | Moeremans et al. | 436/518 |
| 4,777,145 | A | 10/1988 | Luotola et al. | 436/526 |
| 4,778,763 | A | 10/1988 | Makiguchi et al. | 436/47 |
| 4,778,767 | A | 10/1988 | Hummelen et al. | 436/531 |
| 4,780,421 | A | 10/1988 | Kameda et al. | 436/518 |
| 4,781,891 | A | 11/1988 | Galle et al. | 422/64 |
| 4,783,336 | A | 11/1988 | Margel et al. | 424/462 |
| 4,783,835 | A | 11/1988 | Satoh | 382/40 |
| 4,784,213 | A | 11/1988 | Eager et al. | 165/2 |
| 4,785,953 | A | 11/1988 | Buchholz et al. | 215/365 |
| 4,786,606 | A | 11/1988 | Giegel et al. | 436/500 |
| 4,788,136 | A | 11/1988 | Grenier et al. | 435/7 |
| 4,788,150 | A | 11/1988 | Nelson et al. | 436/45 |
| 4,791,055 | A | 12/1988 | Boguslaski et al. | 435/7 |
| 4,791,056 | A | 12/1988 | Sizto et al. | 435/7 |
| 4,793,973 | A | 12/1988 | Ringrose | 422/102 |
| 4,798,095 | A | 1/1989 | Itoh | 73/863 |
| 4,799,599 | A | 1/1989 | Herrmann | 215/307 |
| 4,806,313 | A | 2/1989 | Ebersole et al. | 422/61 |
| 4,808,380 | A | 2/1989 | Minekane | 422/64 |
| 4,808,522 | A | 2/1989 | Atabekov et al. | 435/7 |
| 4,816,418 | A | 3/1989 | Mack et al. | 436/518 |
| 4,820,497 | A | 4/1989 | Howell | 422/63 |
| 4,824,778 | A | 4/1989 | Nagai et al. | 435/7 |
| 4,827,780 | A | 5/1989 | Sarrine et al. | 73/864 |
| 4,830,832 | A | 5/1989 | Arpagauset et al. | 422/65 |
| 4,837,159 | A | 6/1989 | Yamada | 436/45 |
| 4,837,395 | A | 6/1989 | Leeder et al. | 435/7 |
| 4,842,827 | A | 6/1989 | Graf et al. | 422/112 |
| 4,843,000 | A | 6/1989 | Litman et al. | 435/7 |
| 4,843,001 | A | 6/1989 | Haug et al. | 435/7 |
| 4,843,010 | A | 6/1989 | Nawinski et al. | 435/7 |
| 4,845,025 | A | 7/1989 | Lary et al. | 435/2 |
| 4,848,917 | A | 7/1989 | Benin et al. | 366/208 |
| 4,849,176 | A | 7/1989 | Sakagami | 422/64 |
| 4,849,338 | A | 7/1989 | Litman et al. | 435/7 |
| 4,850,470 | A | 7/1989 | Ferkany | 198/345 |
| 4,852,967 | A | 8/1989 | Cook et al. | 350/96 |
| 4,855,110 | A | 8/1989 | Marker et al. | 422/102 |
| 4,855,242 | A | 8/1989 | Soeldner | 436/539 |
| 4,859,423 | A | 8/1989 | Perlman | 422/102 |
| 4,859,583 | A | 8/1989 | Heller et al. | 435/7 |
| 4,861,553 | A | 8/1989 | Mawhirt et al. | 422/65 |
| 4,861,554 | A | 8/1989 | Sakuma | 422/65 |
| 4,863,690 | A | 9/1989 | Berthold et al. | 422/52 |
| 4,863,875 | A | 9/1989 | Bailey et al. | 436/518 |
| 4,868,130 | A | 9/1989 | Hargreaves | 436/526 |
| 4,868,131 | A | 9/1989 | Hiratsuka | 436/528 |
| 4,871,683 | A | 10/1989 | Harris et al. | 436/531 |
| 4,886,177 | A | 12/1989 | Foster | 215/247 |
| 4,890,930 | A | 1/1990 | Nohso | 366/208 |
| 4,891,311 | A | 1/1990 | Anawis et al. | 435/7 |
| 4,895,453 | A | 1/1990 | Devlin et al. | 366/219 |
| 4,895,650 | A | 1/1990 | Wang | 210/222 |
| 4,900,513 | A | 2/1990 | Barker et al. | 422/64 |
| 4,900,686 | A | 2/1990 | Arnost et al. | 436/546 |
| 4,904,583 | A | 2/1990 | Mapes et al. | 435/7 |
| 4,904,632 | A | 2/1990 | Pesek et al. | 502/158 |
| 4,906,432 | A | 3/1990 | Geiselman | 422/63 |
| 4,906,433 | A | 3/1990 | Minekane | 422/64 |
| 4,908,186 | A | 3/1990 | Sakamaki | 422/64 |
| 4,910,148 | A | 3/1990 | Sorensen et al. | 435/317 |
| 4,911,230 | A | 3/1990 | Mayer et al. | 165/48 |
| 4,916,080 | A | 4/1990 | Imai et al. | 436/518 |
| 4,916,081 | A | 4/1990 | Kamada et al. | 436/526 |
| 4,919,887 | A | 4/1990 | Wakatake | 422/67 |
| 4,927,545 | A | 5/1990 | Roginski | 210/745 |
| 4,927,605 | A | 5/1990 | Dom et al. | 422/102 |
| 4,927,769 | A | 5/1990 | Chang et al. | 436/518 |
| 4,928,539 | A | 5/1990 | Champecix | 73/864 |
| 4,931,385 | A | 6/1990 | Block et al. | 435/7 |
| 4,931,402 | A | 6/1990 | Abplanalp | 435/291 |
| 4,933,146 | A | 6/1990 | Meyer et al. | 422/63 |
| 4,933,276 | A | 6/1990 | Baret | 453/7 |
| 4,935,339 | A | 6/1990 | Zahradnik | 435/5 |
| 4,937,048 | A | 6/1990 | Sakai et al. | 422/63 |
| D309,080 | S | 7/1990 | Buchholz | D9/375 |
| 4,939,946 | A | 7/1990 | Teramschi | 74/89 |
| 4,941,201 | A | 7/1990 | Davis | 455/41 |
| 4,941,809 | A | 7/1990 | Pinkerton | 417/500 |
| 4,942,017 | A | 7/1990 | Turpen | 422/64 |
| 4,943,164 | A | 7/1990 | Ohishi et al. | 366/149 |
| 4,944,924 | A | 7/1990 | Mawhirt et al. | 422/104 |
| 4,946,651 | A | 8/1990 | Liston et al. | 422/102 |
| 4,948,726 | A | 8/1990 | Longoria | 435/7 |
| 4,950,588 | A | 8/1990 | Dattagupta | 435/6 |
| 4,951,512 | A | 8/1990 | Mazza et al. | 73/861 |
| 4,952,707 | A | 8/1990 | Edwards et al. | 549/221 |
| 4,953,075 | A | 8/1990 | Nan et al. | 364/140 |
| 4,954,149 | A | 9/1990 | Fullemann | 55/386 |
| 4,954,319 | A | 9/1990 | Koizumi et al. | 422/67 |
| 4,954,452 | A | 9/1990 | Yost et al. | 436/524 |
| 4,954,882 | A | 9/1990 | Kamemoto | 358/22 |
| 4,959,303 | A | 9/1990 | Milburn et al. | 435/7 |
| 4,961,906 | A | 10/1990 | Andersen et al. | 422/102 |
| 4,962,023 | A | 10/1990 | Todd et al. | 435/7 |
| 4,965,049 | A | 10/1990 | Lillig et al. | 422/68 |
| 4,965,187 | A | 10/1990 | Tonelli | 435/5 |
| 4,966,839 | A | 10/1990 | Kaspar | 435/7 |
| 4,967,159 | A | 10/1990 | Manes | 324/650 |
| 4,969,565 | A | 11/1990 | Justai et al. | 215/250 |
| 4,977,786 | A | 12/1990 | Davis | 73/864 |
| 4,978,625 | A | 12/1990 | Wagner et al. | 436/518 |
| 4,980,293 | A | 12/1990 | Jeffs | 435/296 |
| 4,984,628 | A | 1/1991 | Uchida et al. | 165/26 |
| 4,986,891 | A | 1/1991 | Sarrine et al. | 204/299 |
| 4,988,618 | A | 1/1991 | Li et al. | 435/6 |
| 4,989,822 | A | 2/1991 | Fannon | 248/632 |
| 4,992,377 | A | 2/1991 | Saxholm | 435/299 |
| 4,997,768 | A | 3/1991 | Uffenheimer et al. | 436/45 |
| 5,004,582 | A | 4/1991 | Miyata et al. | 422/56 |
| 5,004,904 | A | 4/1991 | Yamakawa et al. | 250/257 |
| 5,008,082 | A | 4/1991 | Shaw | 422/65 |
| 5,009,942 | A | 4/1991 | Benin et al. | 428/36 |
| 5,009,998 | A | 4/1991 | Chow et al. | 435/7 |
| 5,015,157 | A | 5/1991 | Pinkerton et al. | 417/500 |
| 5,017,790 | A | 5/1991 | Kojima | 250/455 |
| 4,906,432 | A | 6/1991 | Geiselman | 422/63 |
| 5,020,980 | A | 6/1991 | Pinkerton | 417/500 |
| 5,024,256 | A | 6/1991 | Vadher | 141/329 |
| 5,030,418 | A | 7/1991 | Miyata | 422/63 |

| Patent No. | | Date | Inventor | Class |
|---|---|---|---|---|
| 5,037,612 | A | 8/1991 | Takahashi et al. | 422/64 |
| 5,038,958 | A | 8/1991 | Dreier | 220/366 |
| 5,039,860 | A | 8/1991 | Yrjonen et al. | 250/328 |
| 5,043,141 | A | 8/1991 | Wilson et al. | 436/52 |
| 5,043,143 | A | 8/1991 | Shaw et al. | 422/65 |
| 5,044,889 | A | 9/1991 | Pinkerton | 417/53 |
| 5,047,210 | A | 9/1991 | Melet | 422/64 |
| 5,055,262 | A | 10/1991 | Sakagami | 422/64 |
| 5,057,281 | A | 10/1991 | Torti et al. | 422/100 |
| 5,061,448 | A | 10/1991 | Mahe et al. | 422/99 |
| 5,061,630 | A | 10/1991 | Knopf et al. | 435/290 |
| 5,066,135 | A | 11/1991 | Meyer et al. | 366/208 |
| 5,066,844 | A | 11/1991 | Schuster et al. | 219/85 |
| 5,068,088 | A | 11/1991 | Hall et al. | 422/52 |
| 5,071,625 | A | 12/1991 | Kelln et al. | 73/72 |
| 5,071,766 | A | 12/1991 | Barr et al. | 435/284 |
| 5,073,625 | A | 12/1991 | Derbyshire | 530/333 |
| 5,077,013 | A | 12/1991 | Guigan | 422/64 |
| 5,077,488 | A | 12/1991 | Davis | 307/296 |
| 5,079,424 | A | 1/1992 | Kobayashi | 250/369 |
| 5,081,872 | A | 1/1992 | Greter | 73/864 |
| 5,082,628 | A | 1/1992 | Andreotti et al. | 422/82 |
| 5,084,242 | A | 1/1992 | Sakuma et al. | 422/100 |
| 5,086,215 | A | 2/1992 | Carsner et al. | 235/462 |
| 5,086,233 | A | 2/1992 | Stafford et al. | 250/256 |
| 5,087,423 | A | 2/1992 | Ishibashi | 422/67 |
| 5,089,418 | A | 2/1992 | Shaw et al. | 436/46 |
| 5,091,206 | A | 2/1992 | Wang et al. | 427/2 |
| 5,096,670 | A | 3/1992 | Harris et al. | 422/65 |
| 5,098,660 | A | 3/1992 | Devaney, Jr. | 422/99 |
| 5,098,661 | A | 3/1992 | Froehlich et al. | 422/102 |
| 5,098,663 | A | 3/1992 | Berthold et al. | 422/104 |
| 5,102,631 | A | 4/1992 | Jordan et al. | 422/42 |
| 5,104,231 | A | 4/1992 | Collier et al. | 366/208 |
| 5,104,621 | A | 4/1992 | Pfost et al. | 422/67 |
| 5,104,807 | A | 4/1992 | mitsumaki et al. | 436/47 |
| 5,104,808 | A | 4/1992 | Laska et al. | 436/48 |
| 5,108,175 | A | 4/1992 | Whitlock | 356/218 |
| 5,108,703 | A | 4/1992 | Pfost et al. | 422/65 |
| 5,108,928 | A | 4/1992 | Menard et al. | 436/43 |
| 5,112,646 | A | 5/1992 | Koshi et al. | 422/52 |
| 5,122,343 | A | 6/1992 | Ishizaka et al. | 422/66 |
| 5,123,477 | A | 6/1992 | Tyler | 165/2 |
| 5,127,541 | A | 7/1992 | Wakatake | 220/737 |
| 5,128,103 | A | 7/1992 | Wang et al. | 422/64 |
| 5,128,105 | A | 7/1992 | Berthold et al. | 422/104 |
| 5,130,254 | A | 7/1992 | Collier et al. | 436/54 |
| 5,133,936 | A | 7/1992 | Umetsu et al. | 422/64 |
| 5,137,693 | A | 8/1992 | Mawhirt | 422/104 |
| 5,139,743 | A | 8/1992 | Ishizaka et al. | 422/63 |
| 5,139,744 | A | 8/1992 | Kowalski | 422/67 |
| 5,139,951 | A | 8/1992 | Butz et al. | 435/284 |
| 5,143,236 | A | 9/1992 | Gueret | 215/311 |
| 5,145,784 | A | 9/1992 | Cox et al. | 436/526 |
| 5,147,529 | A | 9/1992 | Lee et al. | 210/695 |
| D330,428 | S | 10/1992 | Lewis et al. | D24/224 |
| 5,158,895 | A | 10/1992 | Ashihara et al. | 436/526 |
| 5,162,236 | A | 11/1992 | Pang et al. | 436/517 |
| 5,163,360 | A | 11/1992 | Petz | 99/468 |
| 5,163,582 | A | 11/1992 | Godolphin et al. | 222/1 |
| 5,164,318 | A | 11/1992 | Sato et al. | 435/288 |
| 5,167,929 | A | 12/1992 | Korf et al. | 422/102 |
| 5,171,979 | A | 12/1992 | Kwa et al. | 250/223 |
| 5,174,960 | A | 12/1992 | Shaw et al. | 422/63 |
| 5,175,086 | A | 12/1992 | Takekawa et al. | 435/7 |
| 5,176,203 | A | 1/1993 | Larzul | 165/61 |
| 5,178,019 | A | 1/1993 | Keiter | 73/863 |
| 5,178,479 | A | 1/1993 | Brown et al. | 403/13 |
| 5,178,834 | A | 1/1993 | Kagayama et al. | 422/65 |
| 5,180,555 | A | 1/1993 | Monget | 422/102 |
| 5,183,638 | A | 2/1993 | Wakatake | 422/64 |
| 5,186,339 | A | 2/1993 | Heissler | 211/74 |
| 5,186,827 | A | 2/1993 | Liberti et al. | 210/222 |
| 5,187,084 | A | 2/1993 | Hallsby | 435/91 |
| 5,200,084 | A | 4/1993 | Liberti et al. | 210/695 |
| 5,200,151 | A | 4/1993 | Long | 422/100 |
| 5,200,975 | A | 4/1993 | Kato | 373/109 |
| 5,202,093 | A | 4/1993 | Cloyd | 422/102 |
| 5,206,171 | A | 4/1993 | Dillon et al. | 435/293 |
| 5,207,986 | A | 5/1993 | Kadota et al. | 422/65 |
| 5,209,903 | A | 5/1993 | Kanamori et al. | 422/65 |
| 5,212,094 | A | 5/1993 | Ogawa | 436/47 |
| 5,213,761 | A | 5/1993 | Sakagami | 422/63 |
| 5,215,376 | A | 6/1993 | Schulte et al. | 366/348 |
| 5,215,714 | A | 6/1993 | Okada et al. | 422/64 |
| 5,216,926 | A | 6/1993 | Lipscomb | 73/864 |
| 5,223,218 | A | 6/1993 | Fukuoka et al. | 422/52 |
| 5,225,165 | A | 7/1993 | Perlman | 422/102 |
| 5,229,074 | A | 7/1993 | Heath et al. | 422/64 |
| 5,232,664 | A | 8/1993 | Krawzak et al. | 422/64 |
| 5,232,665 | A | 8/1993 | Burkovich | 422/65 |
| 5,236,666 | A | 8/1993 | Hulette | 422/65 |
| 5,236,824 | A | 8/1993 | Fujiwara et al. | 435/5 |
| 5,238,810 | A | 8/1993 | Fujiwara et al. | 435/5 |
| 5,240,674 | A | 8/1993 | Armor | 422/6 |
| 5,240,679 | A | 8/1993 | Stettler | 422/67 |
| 5,242,659 | A | 9/1993 | Wurschum | 422/65 |
| 5,242,660 | A | 9/1993 | Hsei | 422/102 |
| 5,244,633 | A | 9/1993 | Jakubowicz et al. | 422/64 |
| 5,244,663 | A | 9/1993 | Bruttmann et al. | 424/400 |
| 5,246,354 | A | 9/1993 | Pardinas | 417/500 |
| 5,246,665 | A | 9/1993 | Tyranski et al. | 422/64 |
| 5,250,440 | A | 10/1993 | Kelln et al. | 436/48 |
| 5,252,485 | A | 10/1993 | Zlobinsky et al. | 435/316 |
| 5,254,312 | A | 10/1993 | Staebler et al. | 422/100 |
| 5,260,028 | A | 11/1993 | Astle | 422/81 |
| 5,264,182 | A | 11/1993 | Sakagami | 422/63 |
| 5,266,272 | A | 11/1993 | Griner et al. | 422/104 |
| 5,270,210 | A | 12/1993 | Weyrauch et al. | 436/43 |
| 5,272,092 | A | 12/1993 | Hamasaki et al. | 436/172 |
| 5,273,715 | A | 12/1993 | Bridgham et al. | 422/63 |
| 5,275,299 | A | 1/1994 | Konrad et al. | 215/341 |
| 5,277,873 | A | 1/1994 | Hsei | 422/102 |
| 5,279,210 | A | 1/1994 | Pinkerton | 92/170 |
| 5,282,149 | A | 1/1994 | Grandone et al. | 364/497 |
| D344,138 | S | 2/1994 | Nagata | D24/224 |
| 5,283,079 | A | 2/1994 | Wang et al. | 427/2 |
| 5,286,652 | A | 2/1994 | James et al. | 436/48 |
| 5,288,466 | A | 2/1994 | Burns | 422/102 |
| 5,290,513 | A | 3/1994 | Berthold et al. | 422/52 |
| 5,290,708 | A | 3/1994 | Ashihara et al. | 436/526 |
| 5,296,191 | A | 3/1994 | Hall et al. | 422/52 |
| 5,296,195 | A | 3/1994 | Pang et al. | 422/82 |
| 5,297,599 | A | 3/1994 | Bucheli | 141/329 |
| 5,298,425 | A | 3/1994 | Kuhn et al. | 436/43 |
| 5,304,347 | A | 4/1994 | Mann et al. | 422/67 |
| 5,304,787 | A | 4/1994 | Wang | 235/462 |
| D347,479 | S | 5/1994 | Hansen et al. | D24/224 |
| 5,309,981 | A | 5/1994 | Binder | 265/64 |
| 5,312,730 | A | 5/1994 | Piran et al. | 435/7 |
| 5,314,663 | A | 5/1994 | Mimura | 422/67 |
| 5,314,825 | A | 5/1994 | Weyrauch et al. | 436/43 |
| 5,315,375 | A | 5/1994 | Allen | 356/417 |
| 5,316,245 | A | 5/1994 | Ruckwardt | 248/68 |
| 5,316,726 | A | 5/1994 | Babson et al. | 422/65 |
| 5,316,954 | A | 5/1994 | Hupe et al. | 436/89 |
| 5,318,914 | A | 6/1994 | Matte et al. | 436/526 |
| 5,320,809 | A | 6/1994 | Dunn et al. | 422/64 |
| 5,322,668 | A | 6/1994 | Tomasso | 422/104 |
| 5,324,480 | A | 6/1994 | Shumate et al. | 422/63 |
| 5,332,679 | A | 7/1994 | Simons et al. | 436/518 |
| 5,344,610 | A | 9/1994 | Shaw | 422/100 |

| Patent No. | Type | Date | Inventor | Class |
|---|---|---|---|---|
| 5,346,303 | A | 9/1994 | Heinonen et al. | 366/208 |
| 5,348,705 | A | 9/1994 | Koreyasu et al. | 422/67 |
| 5,350,564 | A | 9/1994 | Mazza et al. | 422/63 |
| 5,351,801 | A | 10/1994 | Markin et al. | 198/346 |
| 5,352,612 | A | 10/1994 | Huber et al. | 436/47 |
| 5,355,304 | A | 10/1994 | DeMoranville et al. | 364/413 |
| 5,363,885 | A | 11/1994 | McConnell et al. | 141/1 |
| 5,366,062 | A | 11/1994 | Markin et al. | 198/345 |
| 5,366,697 | A | 11/1994 | Tomasso et al. | 422/64 |
| 5,370,843 | A | 12/1994 | Chiodo | 422/99 |
| 5,371,350 | A | 12/1994 | Motolese | 250/207 |
| 5,372,782 | A | 12/1994 | Karkantis et al. | 422/63 |
| 5,374,395 | A | 12/1994 | Robinson et al. | 422/64 |
| 5,377,854 | A | 1/1995 | Cusack | 215/364 |
| 5,378,433 | A | 1/1995 | Duckett et al. | 422/100 |
| 5,378,881 | A | 1/1995 | Adachi | 235/462 |
| 5,380,485 | A | 1/1995 | Takahashi et al. | 422/62 |
| 5,380,487 | A | 1/1995 | Choperena et al. | 422/63 |
| 5,380,488 | A | 1/1995 | Wakatake | 422/65 |
| 5,384,096 | A | 1/1995 | Burns | 422/102 |
| 5,391,499 | A | 2/1995 | Karkantis et al. | 436/180 |
| 5,392,949 | A | 2/1995 | McKenna | 220/712 |
| 5,393,965 | A | 2/1995 | Bravman et al. | 235/383 |
| 5,399,846 | A | 3/1995 | Pavlidis et al. | 235/462 |
| 5,401,465 | A | 3/1995 | Smethers et al. | 422/52 |
| D358,660 | S | 5/1995 | Swift | D24/224 |
| 5,414,251 | A | 5/1995 | Durbin | 235/462 |
| 5,415,839 | A | 5/1995 | Zaun et al. | 422/64 |
| D359,261 | S | 6/1995 | Swift | D24/224 |
| 5,422,075 | A | 6/1995 | Saito et al. | 422/52 |
| 5,424,036 | A | 6/1995 | Ushikubo | 422/64 |
| 5,426,976 | A | 6/1995 | McHardy et al. | 73/299 |
| 5,427,243 | A | 6/1995 | Roshdy | 206/438 |
| 5,428,470 | A | 6/1995 | Labriola, II | 359/119 |
| 5,429,330 | A | 7/1995 | Bond et al. | 248/61 |
| 5,430,957 | A | 7/1995 | Eigen et al. | 34/423 |
| 5,433,120 | A | 7/1995 | Boyd et al. | 73/863 |
| 5,434,051 | A | 7/1995 | Allard et al. | 435/7 |
| 5,434,083 | A | 7/1995 | Mitsumaki et al. | 436/48 |
| 5,437,361 | A | 8/1995 | Ohmori et al. | 198/465 |
| 5,437,838 | A | 8/1995 | DeMoranville et al. | 422/67 |
| 5,437,841 | A | 8/1995 | Balmer | 422/102 |
| 5,439,645 | A | 8/1995 | Saralegui et al. | 422/64 |
| 5,439,646 | A | 8/1995 | Tanimizu et al. | 422/64 |
| 5,441,895 | A | 8/1995 | Jakubowicz et al. | 436/518 |
| 5,442,164 | A | 8/1995 | Adachi | 235/463 |
| 5,443,790 | A | 8/1995 | Coeurveille et al. | 422/63 |
| 5,443,791 | A | 8/1995 | Cathcart et al. | 422/65 |
| 5,445,936 | A | 8/1995 | Piran et al. | 435/6 |
| 5,445,970 | A | 8/1995 | Rohr | 436/526 |
| 5,445,971 | A | 8/1995 | Rohr | 436/526 |
| 5,447,687 | A | 9/1995 | Lewis et al. | 422/52 |
| 5,453,610 | A | 9/1995 | Gibbons | 250/207 |
| 5,455,175 | A | 10/1995 | Wittwer et al. | 435/286 |
| 5,455,414 | A | 10/1995 | Wang | 235/462 |
| 5,456,360 | A | 10/1995 | Griffin | 206/443 |
| 5,457,530 | A | 10/1995 | Nagai | 356/330 |
| 5,458,785 | A | 10/1995 | Howe et al. | 210/695 |
| 5,458,852 | A | 10/1995 | Buechler | 422/58 |
| 5,462,715 | A | 10/1995 | Koch et al. | 422/64 |
| 5,468,453 | A | 11/1995 | Holt et al. | 422/100 |
| 5,469,749 | A | 11/1995 | Shimada et al. | 73/861 |
| 5,483,843 | A | 1/1996 | Miller et al. | 73/864 |
| 5,501,841 | A | 3/1996 | Lee et al. | 422/101 |
| 5,503,036 | A | 4/1996 | Nguyen et al. | 73/864 |
| 5,507,193 | A | 4/1996 | Ishihara | 73/864 |
| 5,519,635 | A | 5/1996 | Miyake et al. | 364/497 |
| 5,543,112 | A | 8/1996 | Ghead et al. | 422/52 |
| 5,972,295 | A | * 10/1999 | Hanawa et al. | 422/65 |
| 5,985,672 | A | * 11/1999 | Kegelman et al. | 436/50 |
| 6,024,204 | A | * 2/2000 | van Dyke et al. | 198/459.6 |

FOREIGN PATENT DOCUMENTS

| | | | |
|---|---|---|---|
| CA | 2083424 | 11/1992 | |
| DE | 51272 | 3/1890 | |
| DE | 92212 | 6/1897 | |
| DE | 130053 | 4/1902 | |
| DE | 338227 | 8/1918 | |
| DE | 1428777 | 3/1973 | |
| DE | 2505268 | 9/1975 | |
| DE | 1798481 | 6/1976 | G01N/1/00 |
| DE | 3244508 | 6/1984 | |
| DE | 3621831 | 1/1988 | |
| DE | 3934890 | 4/1990 | G01N/35/02 |
| DE | 3926462 A1 | 2/1991 | |
| EP | 0019277 | 5/1980 | |
| EP | 0019871 | 5/1980 | |
| EP | 0030087 | 11/1980 | |
| EP | 0038181 | 4/1981 | |
| EP | 0106536 A2 | 9/1982 | |
| EP | 0078948 | 10/1982 | |
| EP | 0080108 | 11/1982 | |
| EP | 0080109 | 11/1982 | |
| EP | 0087786 | 2/1983 | |
| EP | 0097591 | 6/1983 | |
| EP | 0097591 A1 | 6/1983 | |
| EP | 0097591 B1 | 6/1983 | |
| EP | 0100663 | 7/1983 | |
| EP | 0101192 | 7/1983 | |
| EP | 0102661 | 8/1983 | |
| EP | 0106662 | 10/1983 | |
| EP | 0125995 | 5/1984 | |
| EP | 0125995 | 6/1984 | |
| EP | 0144006 B1 | 11/1984 | |
| EP | 0148166 | 1/1985 | |
| EP | 0149565 | 1/1985 | |
| EP | 0149565 A2 | 1/1985 | |
| EP | 0149565 B1 | 1/1985 | |
| EP | 0152964 | 2/1985 | |
| EP | 0152964 A2 | 2/1985 | |
| EP | 0167834 | 6/1985 | |
| EP | 0169434 | 7/1985 | |
| EP | 0169434 B1 | 7/1985 | |
| EP | 0169434 A2 | 7/1985 | |
| EP | 0189280 | 1/1986 | |
| EP | 0198413 | 4/1986 | |
| EP | 0209290 | 7/1986 | |
| EP | 0219695 | 9/1986 | |
| EP | 0221308 | 9/1986 | |
| EP | 0239382 B1 | 3/1987 | |
| EP | 0251087 | 6/1987 | |
| EP | 0252631 A2 | 6/1987 | |
| EP | 0252631 B1 | 6/1987 | |
| EP | 0253519 A2 | 6/1987 | |
| EP | 0253519 B1 | 6/1987 | |
| EP | 0273969 B1 | 7/1987 | |
| EP | 0285654 | 10/1987 | |
| EP | 0285654 B1 | 10/1987 | |
| EP | 0269752 | 12/1987 | |
| EP | 0281390 | 3/1988 | |
| EP | 0286119 B1 | 4/1988 | |
| EP | 0549573 A1 | 6/1988 | |
| EP | 0299659 A2 | 7/1988 | |
| EP | 0314525 | 10/1988 | |
| EP | 0353264 B1 | 11/1988 | |
| EP | 0329183 B1 | 2/1989 | |
| EP | 0329183 A2 | 2/1989 | |
| EP | 0316766 | 5/1989 | G01N/35/02 |
| EP | 0346878 B1 | 6/1989 | |
| EP | 0355801 B1 | 8/1989 | |
| EP | 0355802 B1 | 8/1989 | |
| EP | 0355823 | 8/1989 | |
| EP | 0355823 A2 | 8/1989 | |

| | | |
|---|---|---|
| EP | 0356250 B1 | 8/1989 |
| EP | 0356883 | 8/1989 |
| EP | 0358948 B1 | 8/1989 |
| EP | 0358948 A2 | 8/1989 |
| EP | 0396657 B1 | 9/1989 |
| EP | 0371265 | 10/1989 |
| EP | 0371265 B1 | 10/1989 |
| EP | 0417301 A1 | 2/1990 |
| EP | 0658762 A2 | 2/1990 |
| EP | 0660115 A2 | 2/1990 |
| EP | 0409126 A2 | 7/1990 |
| EP | 0409606 | 7/1990 |
| EP | 0410645 A2 | 7/1990 |
| EP | 0410645 A3 | 7/1990 |
| EP | 0410645 | 7/1990 |
| EP | 0416285 B1 | 8/1990 |
| EP | 0435481 A2 | 12/1990 |
| EP | 0435481 | 12/1990 |
| EP | 0436995 A2 | 12/1990 |
| EP | 0438158 B1 | 1/1991 |
| EP | 0449321 | 3/1991 |
| EP | 0452892 A2 | 4/1991 |
| EP | 0365569 B1 | 5/1991 |
| EP | 0467302 A2 | 7/1991 |
| EP | 0492499 A2 | 12/1991 |
| EP | 0502638 | 2/1992 |
| EP | 0502638 A2 | 2/1992 |
| EP | 0512368 A2 | 4/1992 |
| EP | 0512368 A3 | 4/1992 |
| EP | 0523425 | 6/1992 |
| EP | 0528708 A1 | 7/1992 |
| EP | 0596987 B1 | 7/1992 |
| EP | 0597017 B1 | 7/1992 |
| EP | 0544578 A1 | 11/1992 |
| EP | 0571716 A1 | 2/1993 |
| EP | 0572185 A2 | 5/1993 |
| EP | 0572185 A3 | 5/1993 |
| EP | 0572217 A1 | 5/1993 |
| EP | 0596205 A2 | 8/1993 |
| EP | 0567892 | 11/1993 .......... G01N/35/04 |
| EP | 0616208 A1 | 3/1994 |
| EP | 0637750 A2 | 7/1994 |
| EP | 0657382 A2 | 7/1994 |
| EP | 0638806 A3 | 8/1994 |
| EP | 0638806 | 8/1994 |
| EP | 0664501 A1 | 8/1994 |
| EP | 0643306 A2 | 9/1994 |
| EP | 0645631 A2 | 9/1994 |
| EP | 0653720 A2 | 11/1994 |
| EP | 0661535 | 12/1994 |
| EP | 0670483 A3 | 2/1995 |
| EP | 0682258 A1 | 2/1995 |
| EP | 0672906 A1 | 3/1995 |
| EP | 0692308 A2 | 7/1995 |
| EP | 0712000 A2 | 9/1995 |
| EP | 0712000 | 9/1995 |
| EP | 0712000 | 5/1996 .......... G01N/35/02 |
| EP | 0712000 | 6/1996 .......... G01N/35/02 |
| FR | 1573224 | 4/1968 |
| FR | 1573224 | 4/1969 |
| FR | 2144110 | 2/1973 ............ G01N/1/00 |
| FR | 2309869 | 4/1976 |
| FR | 2523320 | 3/1983 |
| FR | 2655426 | 12/1990 |
| GB | 1-23637 | 8/1964 |
| GB | 1180957 | 12/1967 |
| GB | 1473042 | 5/1977 |
| GB | 1566098 | 4/1980 |
| GB | 1592297 | 7/1981 |
| GB | 1592299 | 7/1981 |
| GB | 2199407 | 7/1988 |
| GB | 2202814 | 10/1988 |
| GB | 2228730 | 9/1990 |
| GB | 2239093 | 6/1991 |
| JP | 1322728 | 11/1969 |
| JP | 60-188849 | 9/1985 |
| JP | 62-49070 | 3/1987 |
| JP | 62-165057 | 7/1987 |
| JP | 62-194464 | 8/1987 |
| JP | 2-210266 | 8/1990 |
| JP | 4047266 | 2/1992 |
| WO | WO 80/02280 | 10/1980 |
| WO | WO 86/00139 | 1/1986 |
| WO | WO 86/05518 | 9/1986 |
| WO | WO 87/03966 | 7/1987 |
| WO | WO 87/07727 | 12/1987 |
| WO | WO 88/02866 | 4/1988 |
| WO | WO 89/04373 | 5/1989 |
| WO | WO 91/07662 | 11/1989 |
| WO | WO 90/00252 | 1/1990 |
| WO | WP 90/01168 | 2/1990 |
| WO | WO 90/05903 | 5/1990 |
| WO | WO 90/11511 | 10/1990 |
| WO | WO 90/05411 | 5/1991 |
| WO | WO 91/07662 | 5/1991 |
| WO | WO 91/13335 | 9/1991 |
| WO | WO 91/15768 | 10/1991 |
| WO | WO 92/05448 | 4/1992 |
| WO | WO92/12255 | 7/1992 |
| WO | WO 92/16841 | 10/1992 |
| WO | WO 92/16844 | 10/1992 |
| WO | WO 92/20449 | 11/1992 |
| WO | WO 92/22201 | 12/1992 |
| WO | WO 83/01308 | 1/1993 |
| WO | WO 93/01308 | 1/1993 |
| WO | WO 93/02364 | 2/1993 |
| WO | WO 93/03383 | 2/1993 |
| WO | WO 93/12430 | 6/1993 |
| WO | WO 93/12431 | 6/1993 |
| WO | WO 93/16801 | 9/1993 |
| WO | WO 93/22686 | 11/1993 |
| WO | WO 94/04929 | 3/1994 |
| WO | WO 94/19451 | 9/1994 |
| WO | WO 95/00829 | 1/1995 |
| WO | WO 95/03548 | 2/1995 |
| WO | 9625712 | 8/1996 ........... G06F/17/00 |

OTHER PUBLICATIONS

J. Guesdon, et al Magnetic Solid Phase Enxyme Immunoassay; Immunochemistry 1977, vol. 14 443–447.

Yolken; Enzyme Immunoassays for the Detection of Infectious Antigens in Body Fluids: Current Limitations and Future Prospects; Reviews of Infectious Diseases vol. 4, No. 1 Jan.–Feb. 1982.

Hirschbein, et al; Magnetic separations in chemistry and biochemistry; Chemtech Mar. 1982.

Oellerich; Enzyme–Immunoassay: A Review J. Clin Chem Clin Biochem vol. 22, 1984 pp895–904.

Guesdon, et al.;Magnetic enzyme immunoassay for measuring human IgE; J. Allergy Clin Immunol Jan. 1978; vol. 61, No. 1, 23–27.

Kamel, et al; Magnetizable Solid–Phase Fluoroimmunoassay of Phenytoin in Disposable Test Tubes; Clin chem 26/9/1281–1284 (1980).

Klibanov; Immobilized Enzymes and Cells as Practical Catalysts; Science vol. 219.

Mosbach, et al; Magnetic ferrofluids for preparation of magnetic polymers and their application in affinity chromatography; Nature vol. 270 Nov. 17, 1977.

Dawes, et al.; Radioimmunoassay of Digoxin Employing Charcoal Entrapped in Magnetic Polyacrylamide Particles; Clinica Chimica Acta 86 1978; 353–356.

Nye,et al., Solide Phase, Magnetic Particle Radioimmunoassay; Clinica Chimica Acta 69(1976) 387–396.

Hersh,et al; Magnetic Solid Phase Radioimmunoassay; Clinica chimica Acta, 63 1975 69–72.

Pourfarzaneh, et al., Cortisol Directly Determined in Serum by Fluoroimmunoassay with Magnetizable Solid Phase; Clin Chem 26/6 730–733.

Kamel, et al., Nove 125I–Labeled Nortriptyline Derivatives and Their Use in Liquid Pahse or Magnetizable Solid Pahse Second–Antibody Radioimmunoassays; Clin Chem 25/12, 1997–2002 (1979).

Ithakissioset al., Use of Protein Containing Magnetic Microparticles in Radioassays; Clin chem 23/11; 2072–1079 (1977).

Robinson; The Properties of Magnetic Supports in Relation to Immobilized Enzyme Reactors; Biotech and Bioeng. vol. XV 1973.

Carter; Preparation of Ligand Free Human Serum for Radioimmunoassay by Adsorption on Activated Charcoal; Clin Chem 24/2, 362–364(1978).

Jacobs; Separation Methods in Immunoassays; The Ligand Quarterly vol. 4, No. 4, 1981.

Rembaum et al., Synthesis and Reactionsof Hydrophilic Functional Microspheres; J. Macromaol Sci Chem A13(5) 603–632 (1979).

Pourfarzaneh, et al, Production and Use of Magnetizable Particles in Immunoassay, The Ligand Quarterly, vol. 5, No. 1, 1982.

Kaiser, et al., Magnetic Properties of Stable Dispersions of subdomain Magnetite Particles; Journal of Applied Physics; vol. 41, No. 3, Mar. 1970.

Halling et al., Magnetic supports for immobilized enzymes and bioaffinity adsorbents; Enzyme Microb Technol. 1980 vol. 2, Jan.

Allman, et al., Fluoroimmunoassay of Progesterone in Human Serum of Plasma; Clin Chem 27/7 1176–1179–(1981).

Radioimmunoassay and Related Procedures in Medicine 1982.

Klingler, et al., Immunoassay of unconjugated estriol in serum of pregnant women monitored by chemiluminescence; Steroids, vol. 42, No. 2, Aug. 1983.

Wisdom; Enxyme Immunoassay; Clin Chem 22/8/ 1243–1255 (1976).

Scholmerich, et al., Bioluminescence and Chemiluminescence; New Perspectives.

Thorpe et al., [29]Enhanced Chemiluminescent Reactions Catalyzed by Horseradish Peroxidase; Method in Enzymology vol. 133.

Margel et al., Polyglutaraldehyde: A new reagent for coupling proteins to microspheres and for labeling cell surface receptors . . . ; Jounal of Immunologica Methods 28(1979) 341–353.

Margel; Polyaldehyde Microspheres as Probes for Cell Membranes; Ind. Eng. Chem. Prod. Res. Dev. 1982, 21, 343–348.

Sovetskaia Meditsina No Translation.

Margel, et al., Polyacrolein Microspheres as a New Tool in Cell Biology, J. Cell Sci. 56, 157–175 (1982).

Margel, et al., Cell Fractionation with Affinity Ligands Conjugated to Agarose–Polyacrolein Microsphere Beads; J. Cell Sci. 62, 149–159(1983).

Kreuter; Evaluation of Nanoparticles as Drug–Delivery Sysntems I: Preparation Methods. Pharm Acta Helv. 58 No. 7, 1983.

Margel, et al., Chelation of Mercury by Polymercaptal Microspheres: new Potential Antidote for Mercury Poisoning; Joun of Pharm. Sciences; vol. 71. No. 9, Sep. 1982.

Basch, et al., Cell Separation Using Positive Immunoselective Techniques, Journ. of Immunol. Methods, 56(1983) 269–280.

Kaplan,et al., The Selective Detection of Cell Surface Determinants by means of Antibodies and Acetylated Avidin Attached tooHighly Fluorescent Polymer Microspheres; Biochem and Biophysic Acta 728(1983)112–120.

Margel, et al., Novel Effective Immunoadsorbents Based on Agarose–Polyaldehyde Microsphere Beads: Synthesis and Affinity Chromatography, Analytical Biochem. 128 342–350(1983).

Marcus, et al., A New Immunoadsorbent for Hemoperfusion: Agarose–Polyacrolein Microsheres Beads; Biomat Med. Dev., Art. Org. 10(3) 157–171 (1982).

Merivuori, et al., Cell Labelling and separation with polyglutaraldehyde microspheres; Exp Cell Res 130 (1980).

Kempner,et al., Electrophoretic cell sepatation using polyacrolein microspheres, Electrophosesis 1982, 3, 109–113.

Kumakura et al.,; Polymeric Microspheres for Immunoresearch; Immunological communications 13(2), 119–125(1984).

Morimoto et al., Dispersion State of Protein stabilized Magnetic Emulsions; Chem Pharm Bull 30(8) 3024–3027(1982).

Boland et al., The Ciba Corning ACS:180 Benchtop Immunoassay Analyzer; Clin Chem 36/9, 1598–1602 (1990).

ACS:180 Automated Chemiluninescence System.

Rembaum et al., Immunomicrospheres: Reagents for Cell Labeling and Separation, Science vol. 208. Apr. 25, 1980.

Tokes et al., Synthesis of adriamycin coupled polyglutaraldehyde microspheres and evaluation of their cytostatic activity; Proc Natl. Acad Sci. USA vol. 79: 2026–2030 Mar. 1982.

Margel et al., Synthesis and Characterization of Poly(glutaraldehyde). A Potential Reagent for Protein Immobilization and Cell Separation; Macromolucule vol. 13, No. 1, Jan. Feb. 1980.

Margel; Characterization and Chemistry of Polyaldehyde Microshpheres; Journ of Polymer Science vol. 22, 3521–3522(1984).

Marcus et al., Extracorporeal removal of specific antibodies by hemoperfusion through the immunosorbent agarase–polyacrolein micrsphere beads: Remaoval of Anti–bovine serum albumin in animals; Journ of Viomed Materials Research vol. 18 1153–1167(1984).

Margel; Agarose polyacrolein microsphere beads;Febs Letter; vol. 145 No. 2; Aug. 1982.

Margel et al., Novel Effective Immunoadsorbents Based on Agarose–Polyaldehyde Microshere Beads: Synthesis and Affinity Chromatography; Analytical Biochem 128(342–350(1983).

Margel et al., Polyacrolein Microspheres as a new tool in cell biology; J. Cell Sci 56, 157–175(1982).

Marel et al., A novel synthesis of polyacrolein microspheres and their application for cell labeling and cell separation; Immuno Communications 10(7), 567–575(1981).

Hage et al., High performance immunoaffinity chromatography and Chemiluminscent Detection in the Automation of a Parthyroid Hormone Sandwich Immunoassay; Anal. Chem 1991, 63, 586–595.

Bronstein et al., Instrumentation for luminescent assays; ACL: 33.

Campbell, Chemiluminescence Principles and Applications in Biology and Medicine.

The Ideal chemiluminometer. Sec. 2.4.

Chemiluminescence immunoassay Sec. 8.2.

O'Brien et al., The magic lite system and acridinium ester-based immunoassays; Immunoassay Automation: A practical guide.

Dudley; Chemiluminescence Immunoassay: An Altermantive to RIA; Laboratory Medicine vol. 21, No. 4, Apr. 1990.

Dyke; Luminescence Immunoassay and Molecular Applications.

Luminescence Immunopassay and Molecular Applications; pp. 69–75, 149–156.

Woodhead et al., Magic Lite Design and Development, Journ of Bioluminescence vol. 4, 611–614 (1989).

Express. New Intelligent random access cheimistry analysis Circle No. 578.

Shamberger et al., Evaluation of bichromatic random access analyzer; Analyzer Oct. 1989, 22.

The Lancet Jan. 14, 1984. vol. 1 1984.

550 EXPRESS Shemistry Analyzer.

T3 Uptake [1251] Radioassay MAGIC Ciba Corning.

Quality Value. Customer Satisfaction Ciba Corning Diagnostics Corp.

Corning Magic Lite II.

ACS–180.

Kamel et al., Magnetizable Solid–Phase Fluoroimmunoassay of Phenytoin in Disposable Test Tubes; Clin Chem vol. 26, No. 9. 1980.

Berry et al., A Laboratory and Clinical Evaluation of an Immunochemiluminometric Assay of Thyrotropin in Serum; Clin Chem. vol. 34. No. 10, 1988.

Weeks et al., Chemiluminescence immunoassay: an overview; Clin Science 1986 70,403–408.

Weeks et al., Acridinium Esters as High–Specific–Activity Labels in Immunoassay; Clin Chem 29/8, 1474–1479(1983).

Shridi et al., A direct fluoroimmunoassay for conjugated chenodeoxycholic acid using antibody coupling to magnetisable particles; Ann Clin Biochem 1980; 17:188–191.

Sidki et al., Direct determination of primidone in serum of plasma by a magnetisable solid–phase fluoroimmunoassay; Ann Clin Biochem 1983:20: 227–232.

Abdulla et al., Development of a Magnetisable solid–phase fluoroimmunoassay for primaquine and carboxyprimaquine; Southeast Asian J. Trop Med. Pub Hlth. vol. 20, No. 3, 1989.

Ciba Corning Laboratory Diagnostic Reagents and Systems packet.

Patent Abstracts of Japan vol. 16 Num 225(p1360).

Symbol: A New Communications Medium fo the Information Age.

European Search Report ep 92 30 1483.

The Future of Bar Coding.

Symbol Technologies: The Bar Code Data Capture Company.

Symbol Just What the Doctors Ordered: Met Path Boosts Qualigy, Beats the Competition with PDF417.

Symbol: A PDF417 Primer: A guide to understanding second generation bar codes and portable data files.

* cited by examiner

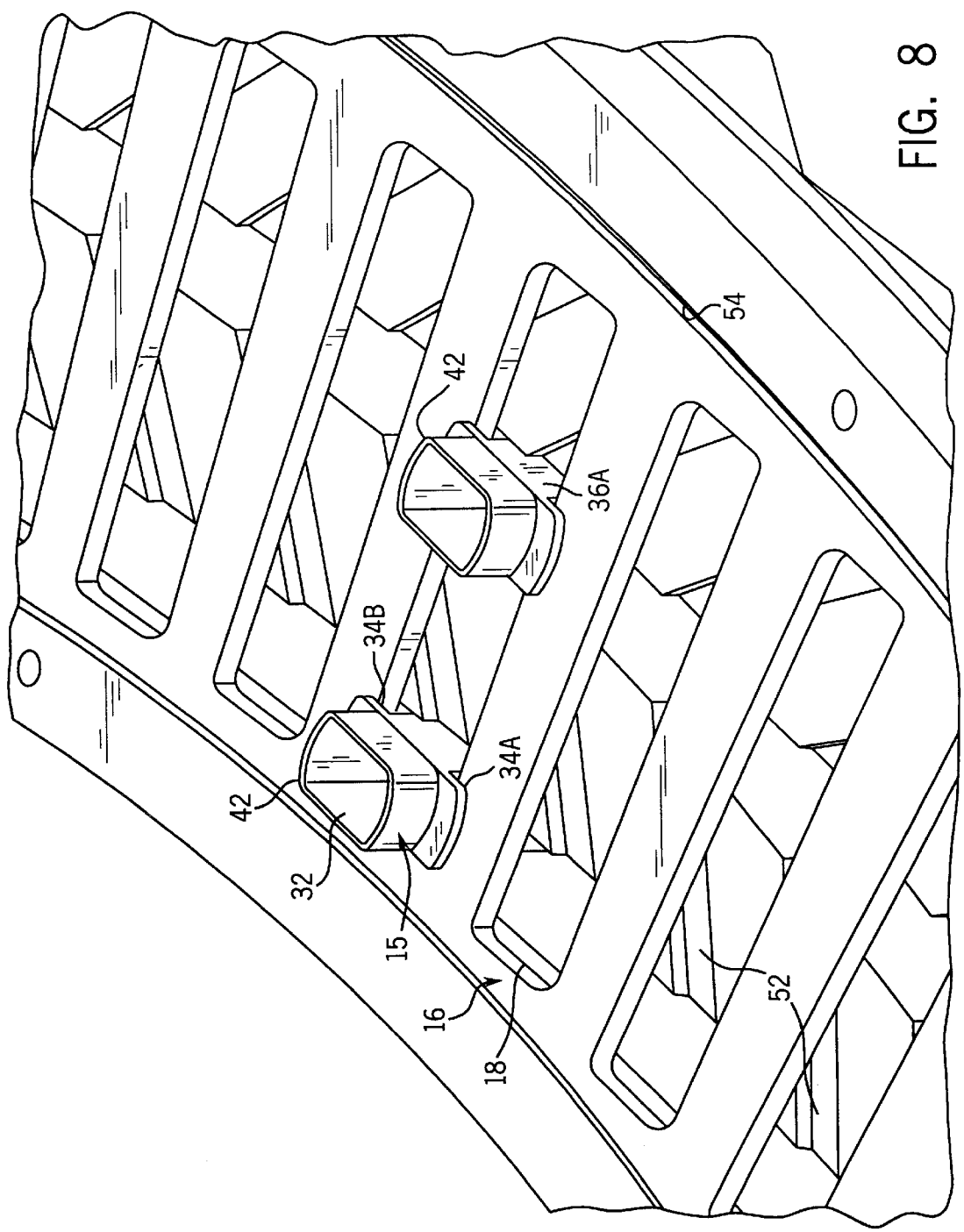

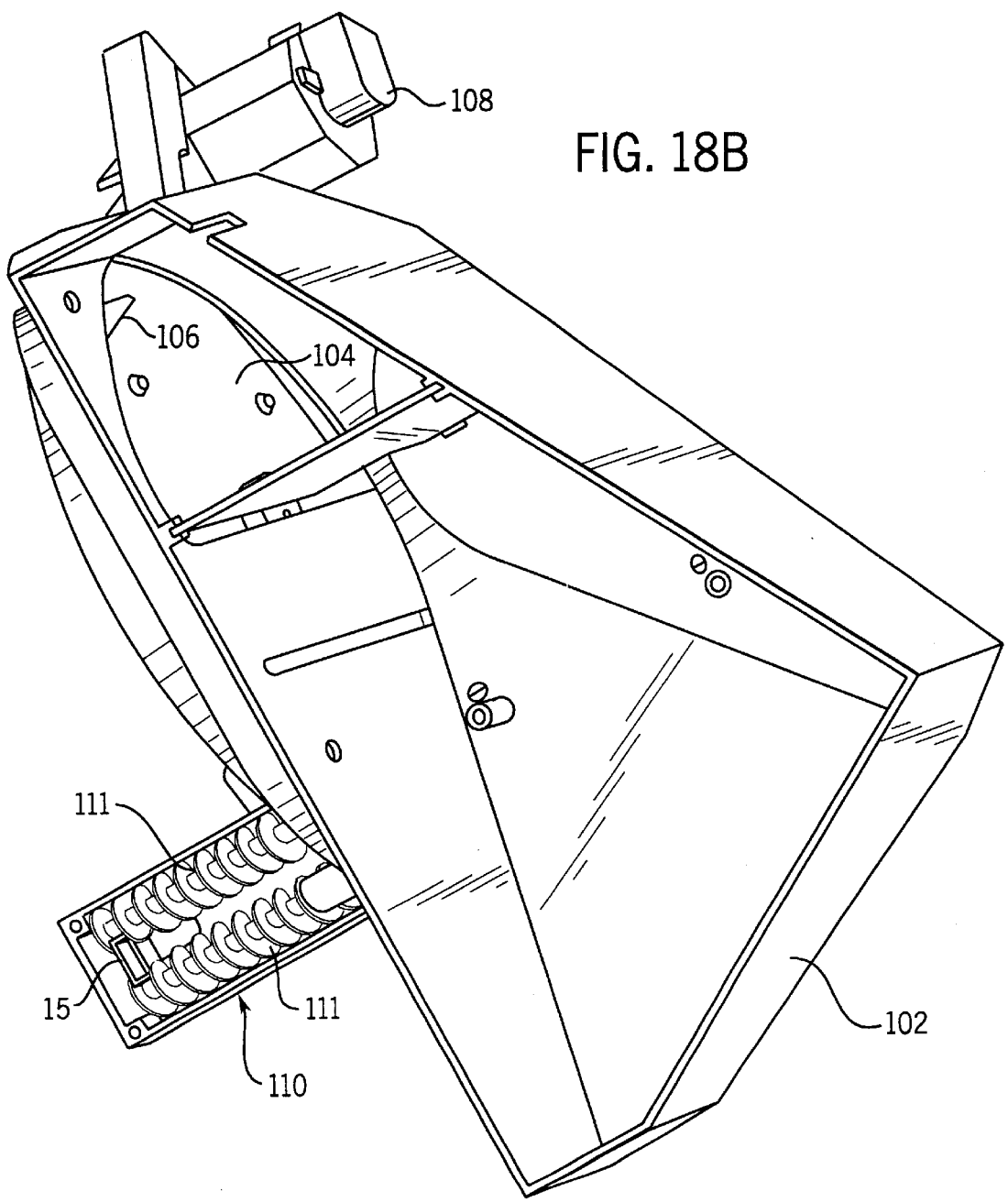

133A →

135A 137A  137B

133B →

135B

139

133C →

135C

STRUCTURE FOR DETERMINATION OF ITEM OF INTEREST IN A SAMPLE

REFERENCE TO RELATED APPLICATION

This case is a divisional application of U.S. patent application, Ser. No. 09/140,607, filed on Aug. 26, 1998, which is a divisional of Ser. No. 08/715,780, now U.S. Pat. No. 5,856,194 filed on Sep. 19, 1996, both of which are assigned to the assignee of the present case.

BACKGROUND

Embodiments described herein relate generally to methods and structures which determine an item of interest in a sample.

To provide information about a patient's health, a number of tests can be performed on a patient sample, such as the patient's bodily fluids. These bodily fluids may include blood, urine, etc. The tests performed on the patient's bodily fluids can determine an item of interest in the bodily fluids. Based on the determination of the item of interest in the patient's bodily fluids, information about the patient's health status can be obtained.

SUMMARY

One embodiment discussed herein relates to a structure for performing a process for determining an item of interest in a sample. The structure comprises a process path. The process path comprises a process lane including a process step performance lane where a process step is performed, and a process step avoidance lane where the process step is avoided. A first prime mover is operatively connected with the process path for moving a container holding the sample along the process path. A first pipetting system is operatively associated with the process path for introducing the sample to the container. A second pipetting system is operatively associated with the process path for introducing a reagent to the container. A device is operatively connected with the process path and is selectively engagable with the container for mixing the sample and the reagent in the container. A second prime mover is operatively connected with the process path for selectively positioning the container in a selected one of the process step performance lane and the process step avoidance lane. A reader is operatively connected with the process path for determining the item of interest in the sample based upon a reaction between the sample and the reagent.

In another embodiment, the structure comprises a process path. The process path comprises a process lane accepting a container for the sample. The process lane includes a process step performance lane where a process step is performed, and a process step avoidance lane where the process step is avoided.

In an additional embodiment, a structure comprises a process step performance lane accepting a container for the sample where a process step is performed, and a process step avoidance lane accepting the container where the process step is avoided.

Another embodiment provides a structure comprising a cover, a base connected with the cover, a disk rotatably disposed between the cover and the base and a slot disposed on the disk for accepting a container for the sample. The slot has a longitudinal axis and the container is movable along the longitudinal axis.

Yet a further embodiment provides a structure comprising a process lane for accepting a container for holding the sample. The process lane includes a bypass region for selectively automatically performing a process step on the sample in the container.

Other embodiments provide a structure comprising a process lane for accepting a container for holding the sample. The process lane includes an element for providing selective automated performance of a determination of item of interest process step.

BRIEF DESCRIPTION OF DRAWINGS

FIG. 8 is an enlarged sectional view of a portion of the component of FIG. 1 showing interaction with the container of FIG. 7B;

FIGS. 18A, 18B and 18C illustrate an element of the component shown in FIG. 1;

DETAILED DESCRIPTION OF PREFERRED EMBODIMENTS

Figure 1:
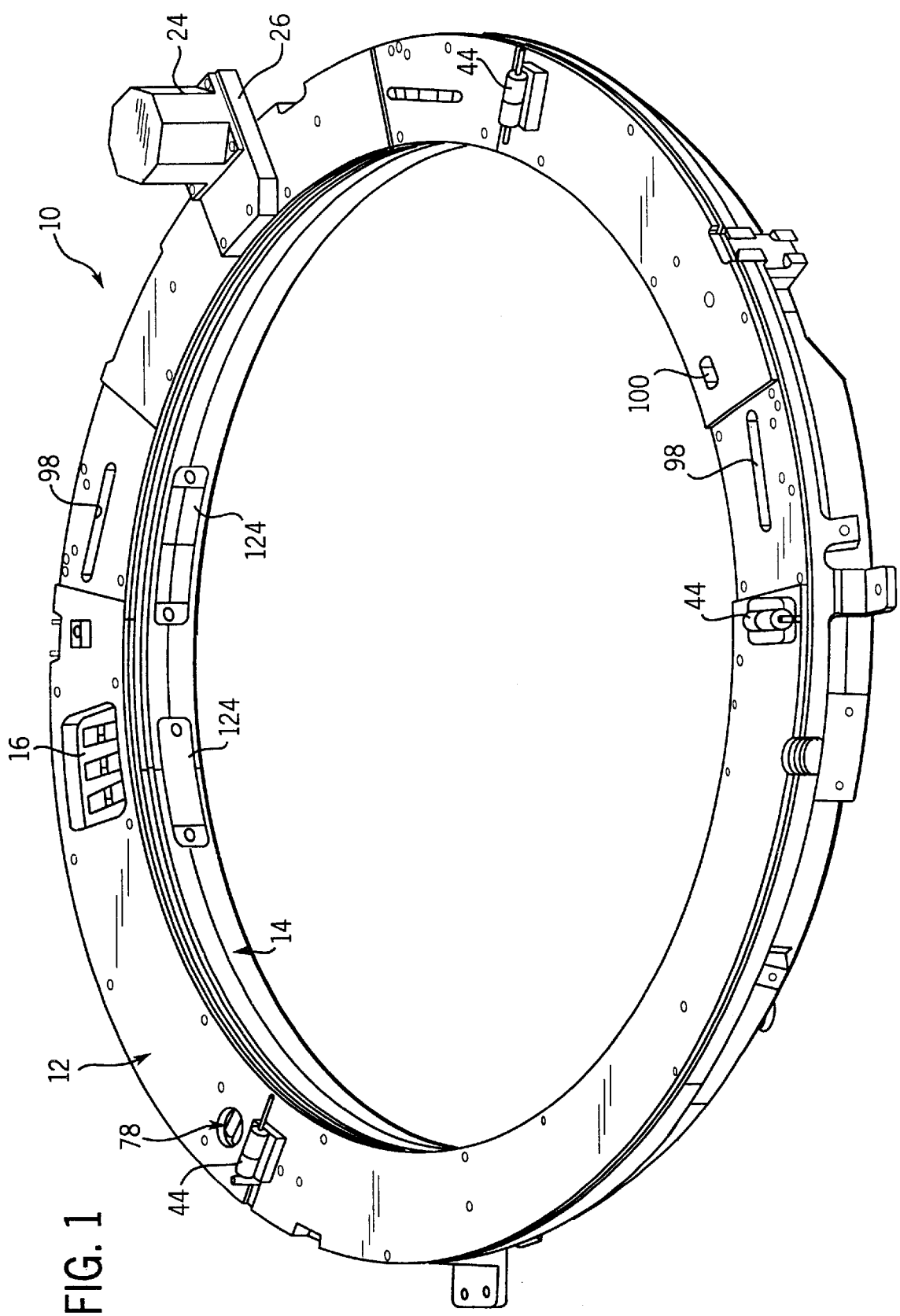
FIG. 1 is a perspective view of a component of an analyzer.

The embodiments described herein relate to methods and structures for determining an item of interest in a sample. The item of interest may be an antibody, an antigen, concentrations of the former or latter or any other desired element of the sample. In an exemplary embodiment, the item of interest is selected from, but are no limited to, antibodies to HCV, antibodies to HIV 1/HIV 2, antibodies to hepatitis B core antigen (HBcAb), carcinoembryonic antigen (CEA), cancer antigen 19-9 (CA19-9), Hepatitis B Surface Antigen (HBsAg), antibodies to Hepatitis B Surface antigen (HBsAb), alpha-fetoprotein (AFP), Total prostate specific antigen (Total PSA), Free PSA, Thyroid stimulating Hormone (TSH), luteinizing hormone (LH), follicle stimulating hormone (FSH), beta human chorionic gonadotropin (B-hCG), Free Thyroxine (Free T4), Free triiodothyronine (Free T3), Total T4, Total T3, Progesterone, Testosterone, Estradiol, Prolactin, vitamin B12 (B12), Folate, Glycated Hemoglobin, and Ferritin. The structures and methods may be employed in a number of different configurations.

For the sake of clarity of understanding, the structures and methods will be discussed with respect to their employment in an immunoassay analyzer which performs approximately 200 determinations of items of interest in a sample in an hour. It is to be noted that the structures and methods can be used in other employments, such as analyzers which perform 600, 400, 100, 50, etc. determinations in an hour. A number of analyzers may be joined together or integrated to meet individual needs, such as modifying the number of tests performed in a given time period (throughput), tailoring the items of interest to be determined, etc. For example a number X of analyzers which perform Y determinations in a given hour may be connected such that the connected analyzers perform XY determinations in an hour.

It is to be noted that all such analyzers perform all determinations of items on interest in substantially the same way. For instance, all determination process steps for all items of interest are performed within the same time frame, such as 18 seconds, irrespective of the number or type of determinations to be performed by the given analyzer. These analyzers may include common elements, such as reagents, disposable articles, element, such as fluids and the like, delivery technologies, determination step performance mechanisms, software, etc.

In other applications, the analyzer may be joined, e.g. with a conveyor system and the like, along with supporting hardware and software, such that the analyzer can be used with different analyzers, such as clinical chemistry or hematology analyzers and the like, in the same setting. This conveyor system may move samples among the analyzers such that different determinations can be made with respect to one sample. Also, while operation of the analyzer is described herein with respect to only one analyzer, for the sake of clarity, it is to be remembered that multiple analyzers can operate in the same of in different fashion, either simultaneously or at different times. Furthermore, steps of one method of operation can be combined with steps of another method of operation to arrive at yet more methods of operation.

As illustrated in FIG. 1, the analyzer comprises a process path 10. It is understood that there are other elements (not shown), such as fluid delivery mechanisms, suppliers, and the like, of the analyzer that support operation of the process path 10. While the process path 10 is illustrated as being substantially circular in configuration, the process path 10 may take other configurations, such as linear, serpentine, etc., as desired.

The process path 10 includes a cover 12 and a base 14. The base 14 may be attached to a support frame (FIG. 17) and the cover 12 is attached to the base 14. The cover 12 may be a single piece or may comprise multiple, sometimes 6, pieces. Various elements, some of which are described below, of the process path 10 are connected to at least one of the cover 12 and the base 14. The cover 12 and the base 14 include structures, such as openings and the like, for accommodating some of the elements. In, one embodiment, the base 14 has an inner diameter of about 24.58 inches, an outer diameter of about 30.08 inches and a height of about 1.99 inches. The base 14 may be made of any suitable material, such as a metal, a polymer and the like. In one embodiment, the base 14 is made of anodized aluminum, including a reduced friction coating, such as a PTFE-impregnated anodized coating. In a particular embodiment, the base 14 is made from 6061-T6 aluminum with a MIL-A-63576, Type I finish. The cover 12 may be made of a material which is substantially similar to the material of the base 14.

Figure 2:
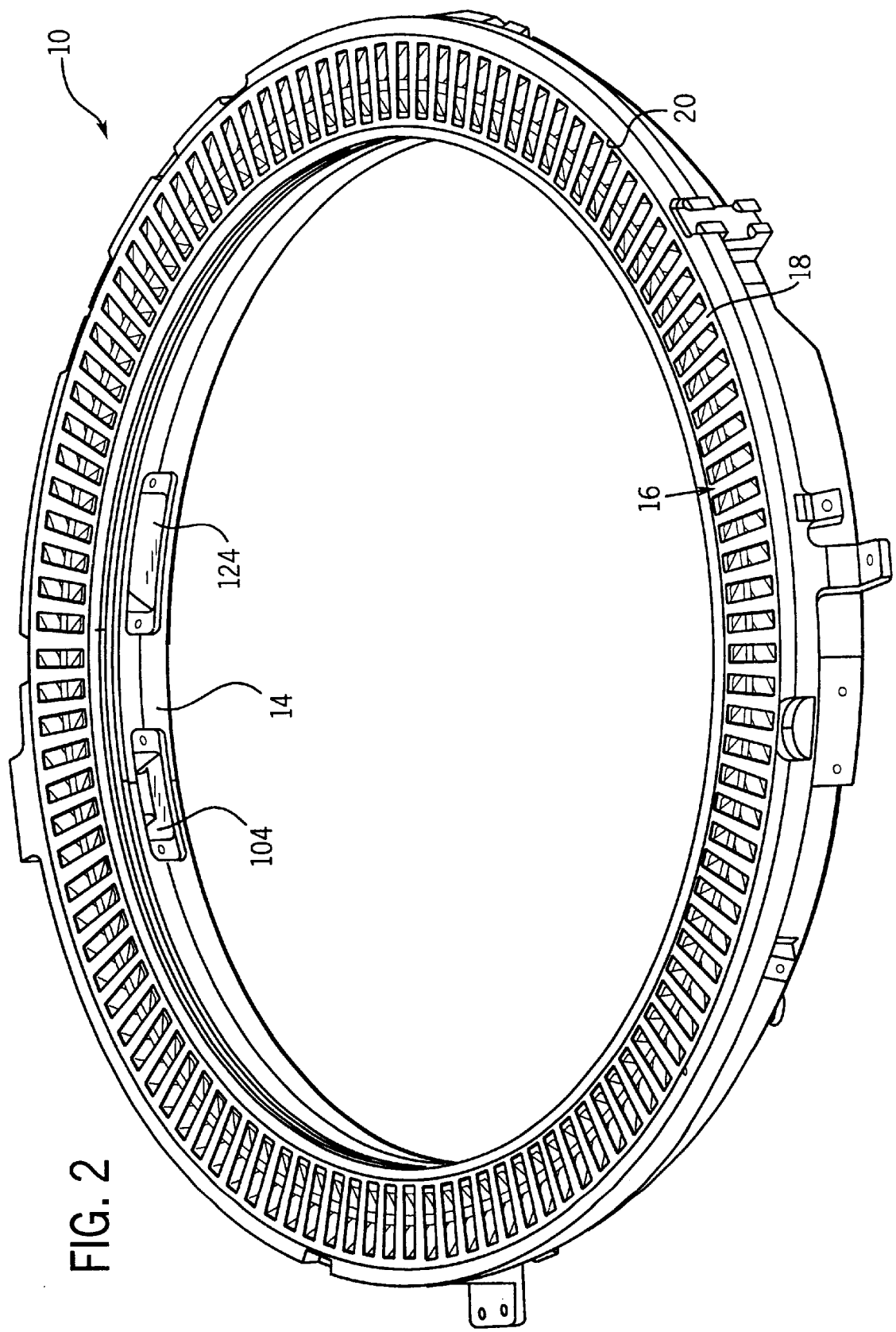
FIG. 2 shows the component of FIG. 1 with elements thereof removed for clarity.

FIG. 2 shows the process path 10 with the cover 12 removed from the base 14. With the cover 12 removed, a disk 16 is visible. The disk 16 is located between the cover 12 and the base 14 and is movable with respect to both the cover 12 and the base 14.

Figure 32A:
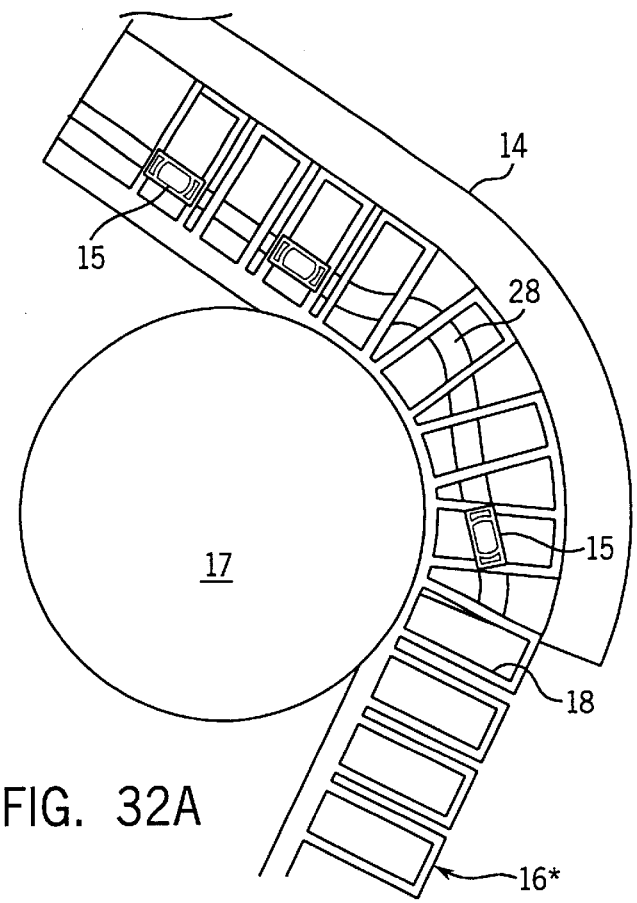
FIGS. 32A and 32B illustrate portions of another embodiment of the process path.
Figure 32B:
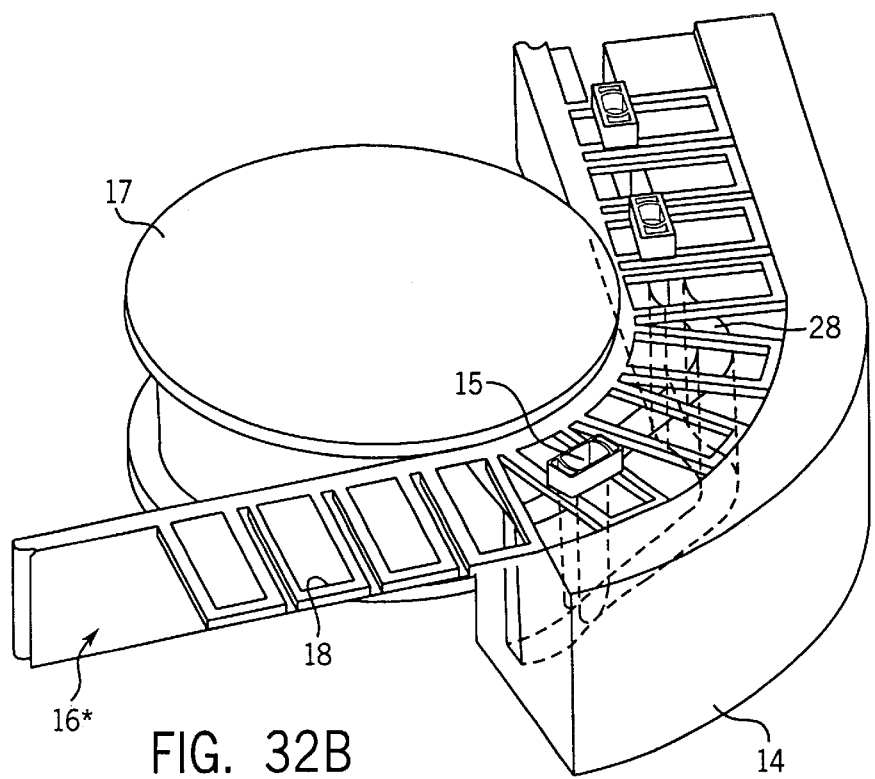

In some embodiments, the disk 16 may be replaced by a belt 16', shown in FIGS. 32A and 32B, driven by a wheel 17. Use of the belt 16' provides for orientations other than substantially circular, i.e. serpentine and like, of the process path 10. The belt 16' moves with respect to the cover 12 and the base 14 in substantially the same manner as the disk 16. In other aspects, construction of the process path 10 is substantially similar irrespective of use of the disk 16 or the belt 16'.

Figure 3:
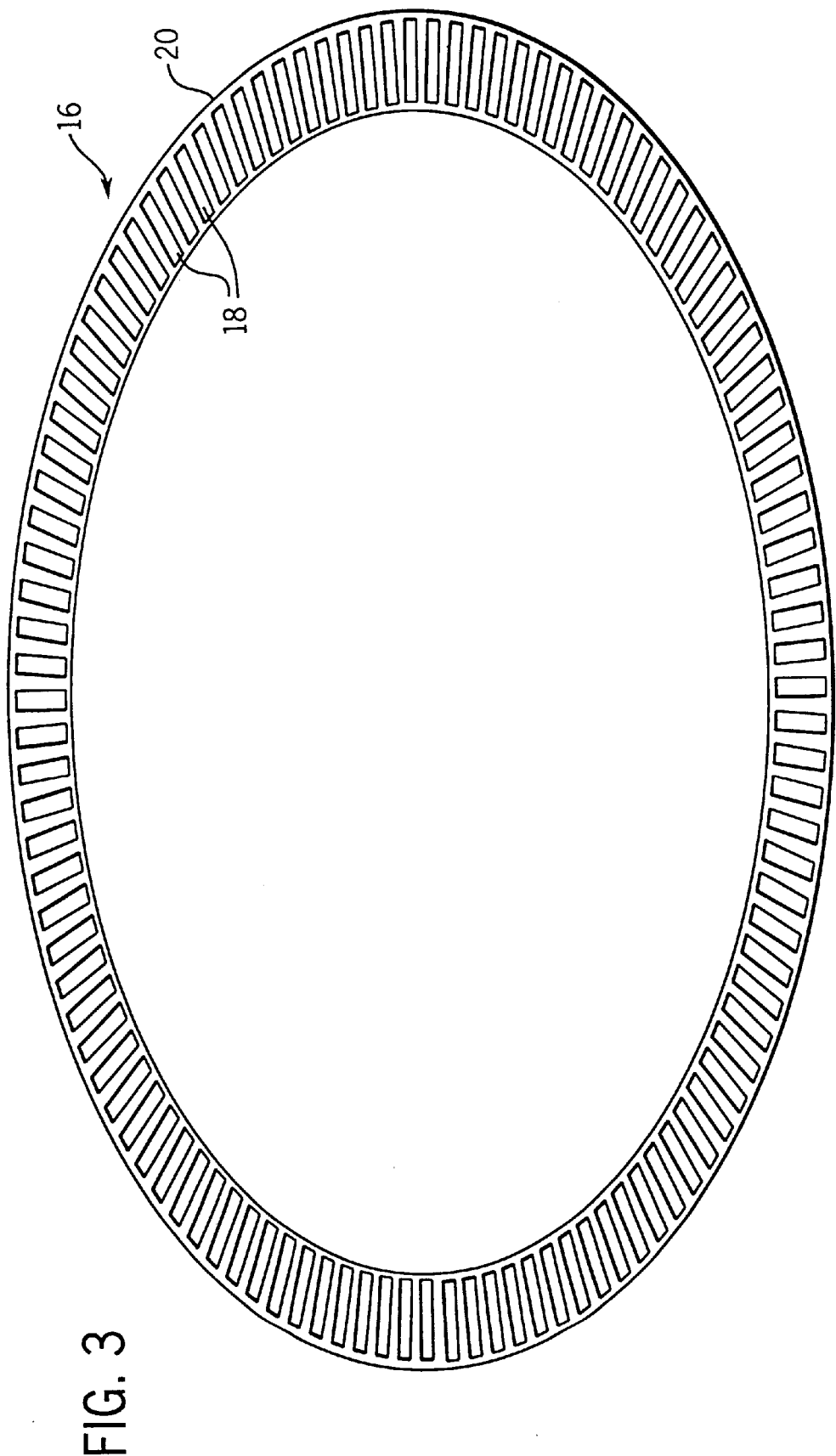
FIG. 3 is a perspective view of an element of the component shown in FIG. 1.

The disk 16, illustrated more clearly in FIG. 3, has, in one embodiment, an inner radius of about 25.2 inches and an outer radius of about 29.3 inches. The disk 16 may have a thickness of about 0.063 inches. The disk 16 may be formed from any suitable material, such as a polymer and the like. In a particular embodiment, the disk 16 is made from polyvinyl chloride. The disk 16 may be machined, molded or the like. In an exemplary embodiment, the material comprising the disk 16 is chosen with respect to the material of the base 14 to reduce friction between the base 14 and the disk 16.

Figure 19:
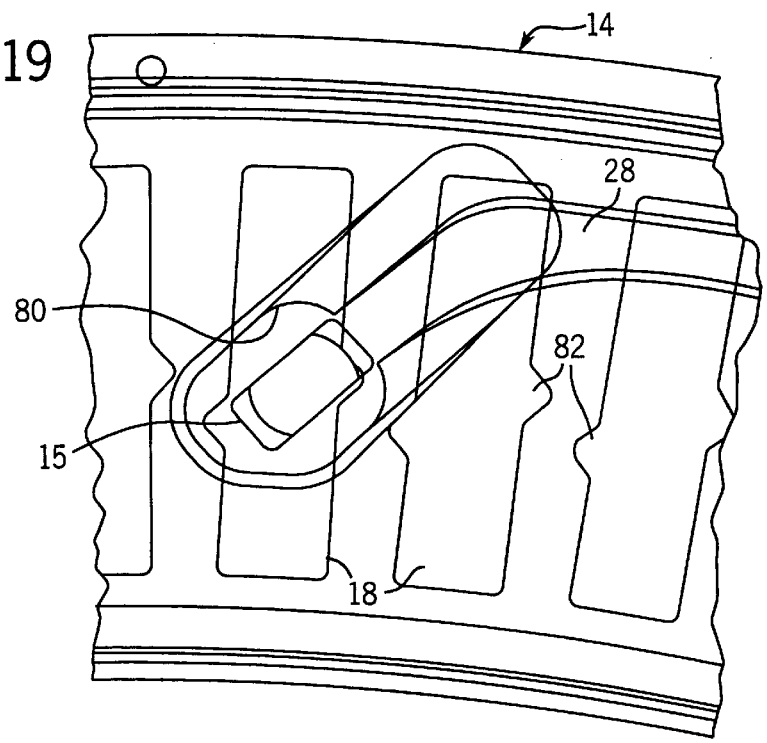
FIG. 19 is an enlarged sectional view of a section of another embodiment substantially similar to that shown in FIG. 13.
Figure 20B:
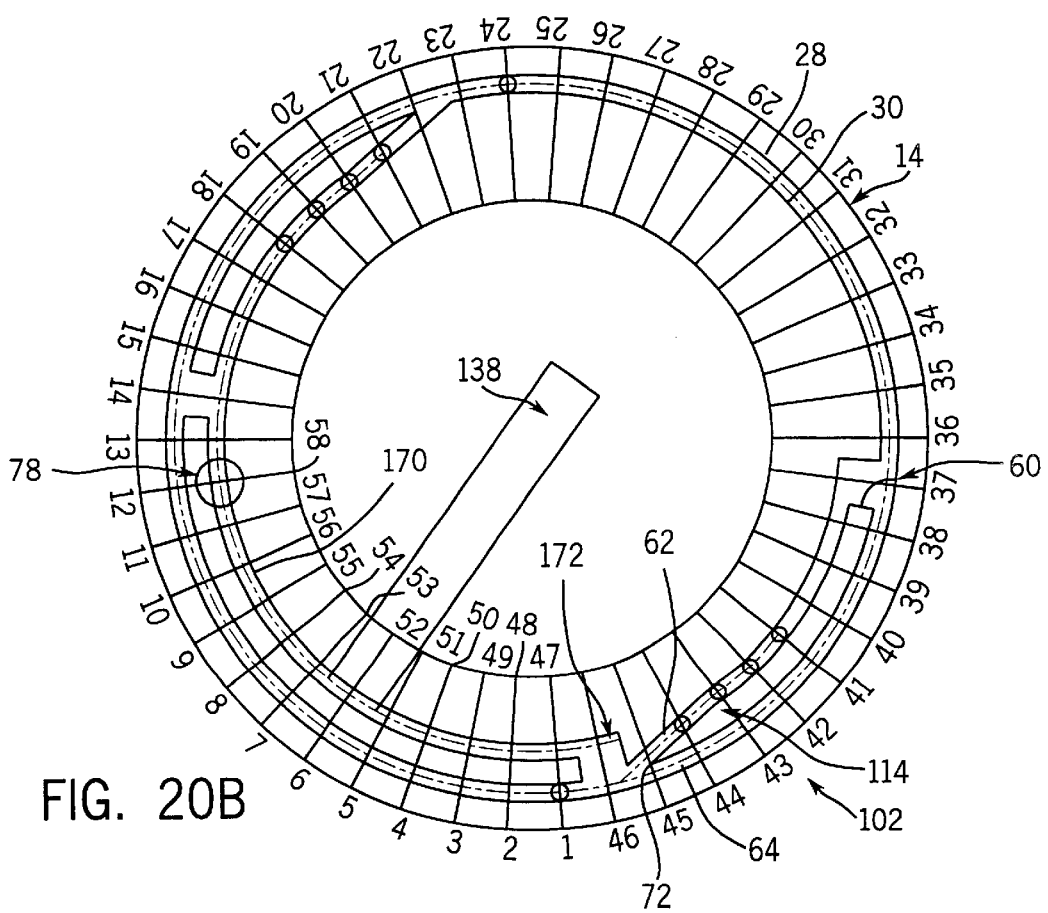

A plurality 112 in the illustrated embodiment, of slots 18 are disposed on the disk 16. As is discussed in greater detail later, the slots 18 cooperate with structures on the base 14 to move containers 15 (FIGS. 7A and 7B) along the process path 10. Each slot 18 has, with respect to the disk 16 in an exemplary embodiment, a radial length of about 1.75 inches and a tangential width of about 0.45 inches with a slot 18 centerline being located at a radius of about 13.614 inches. As is discussed further below, the slot 18 has a longitudinal axis and the container 15 is capable of moving within the slot 18 along the slot's 18 longitudinal axis. To facilitate movement of the container 15 along the longitudinal axis of the slot 18, the process path 10 may include a configuration, such as a surface, a diverter, a prime mover engagable with the container 15, and the like. In another embodiment, one end of the slot 18 may include a latitudinally expanded width (FIG. 13) to facilitate removal of a container 15 from the disk 16. In still a further embodiment, the latitudinally expanded width may be located at another region of the slot 18 (FIG. 19).

The disk 16 is configured to facilitate movement of the disk 16 with respect to the cover 12 and the base 14. In one embodiment, a plurality of teeth 20 are disposed along an outer diameter surface of the disk 16. In an exemplary embodiment, the teeth 20 may be about 938 in number with a diametral pitch of about 32, a pressure angle of about 20 degrees and a pitch diameter of about 29.3125 inches.

Figure 6:
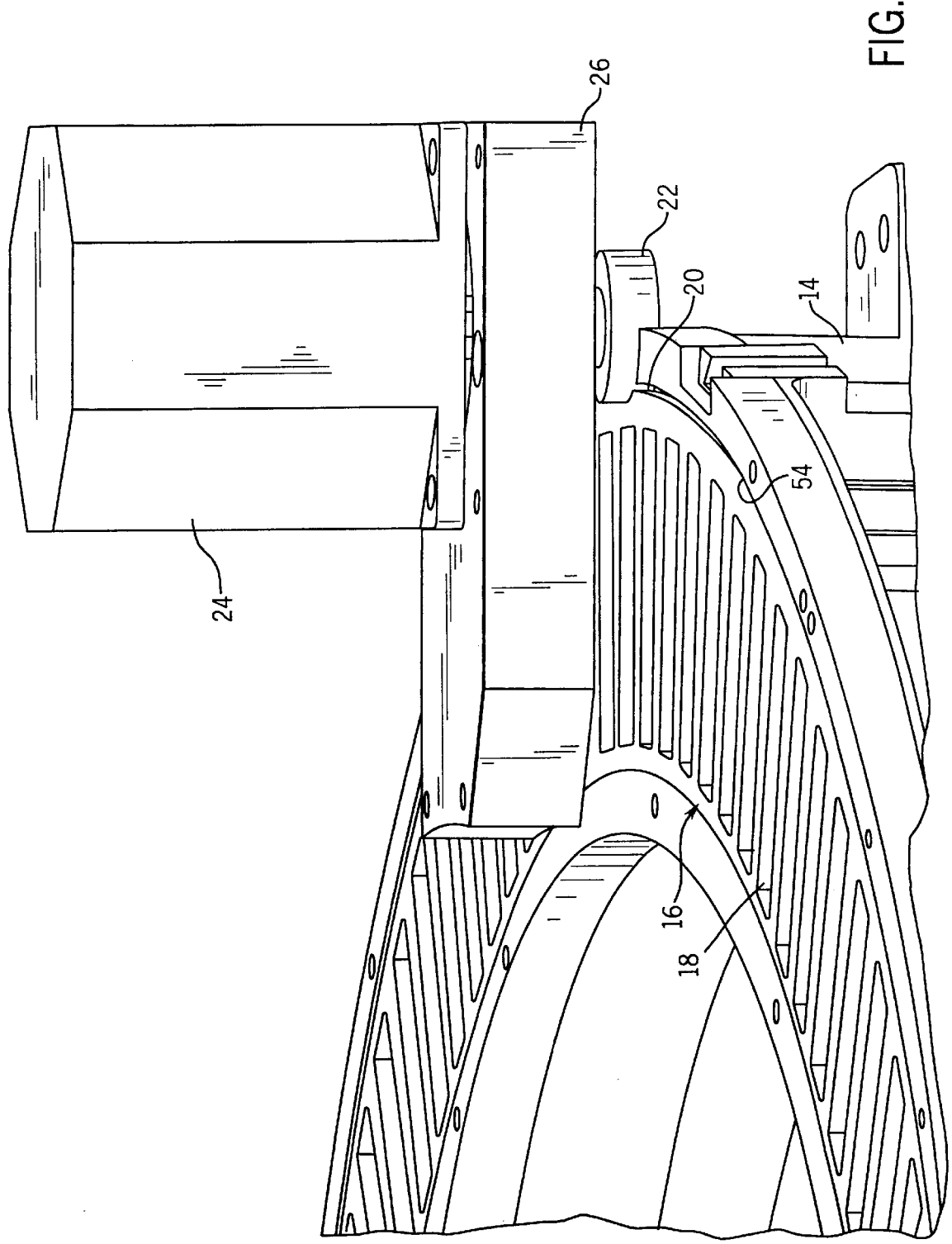
FIG. 6 is an enlarged sectional view of the component of FIG. 1 with elements removed for clarity.

As shown in FIG. 6, the teeth 20 mate with a gear 22 which is driven by a prime mover 24 attached to the base cover 12 by a bracket 26. In an exemplary embodiment, the gear 22 is made from Estane 58130 natural 92A/50D polyurethane and the motor 24 is a P21 model available from Pacific Scientific of Rockford, Ill. The prime mover 24, the entire process path 10 and its supporting elements, are connected with and are operated by a suitable controller, such as a computer (not shown) running appropriate routine and the like. In this manner, the disk 16 moves responsive to movement of the gear 22 by the prime mover 24. In a particular embodiment, the prime mover 24 is a stepper motor.

Figure 4:
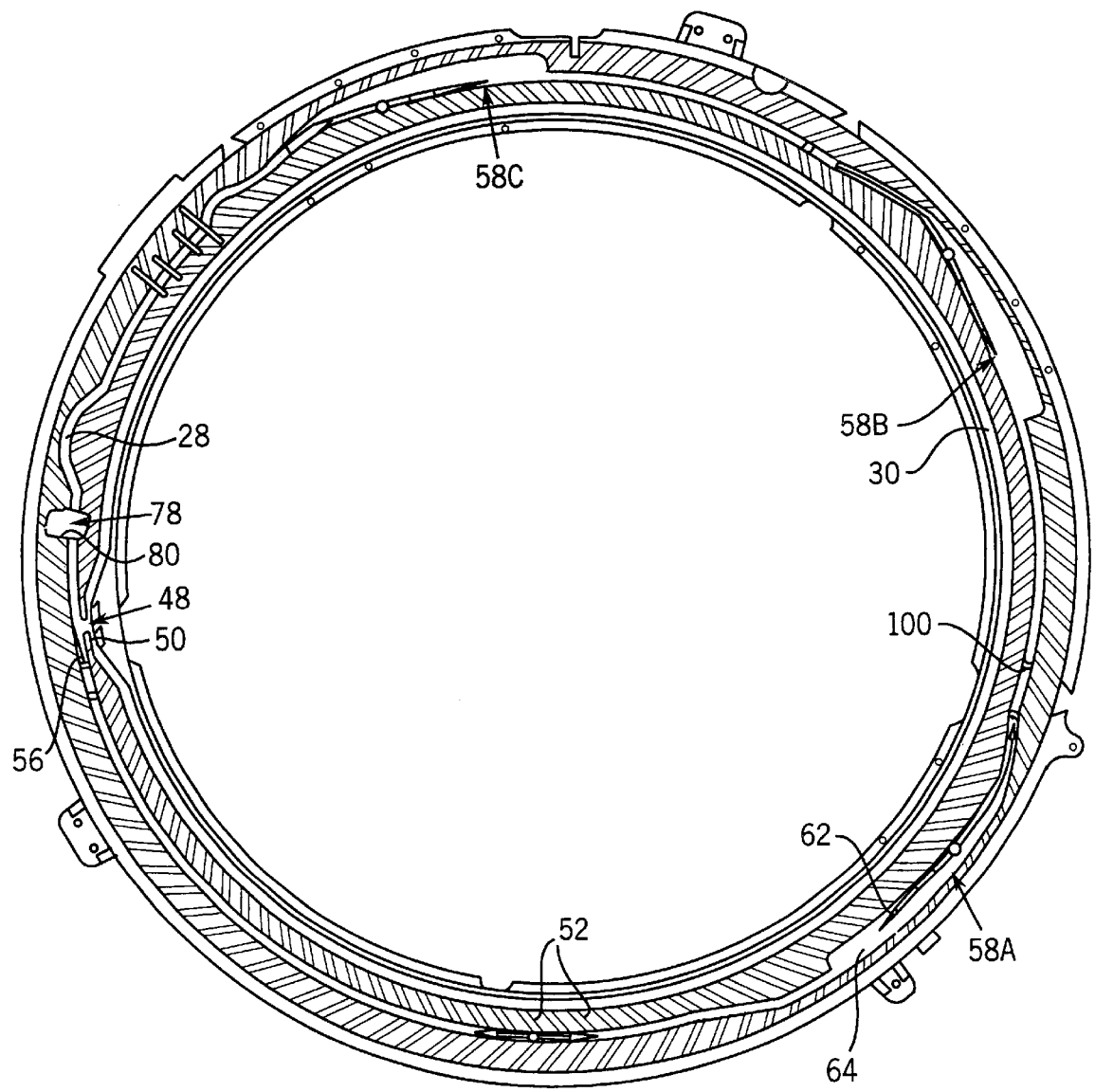
FIG. 4 is a top view of the component of FIG. 1 with elements thereof removed for clarity.

Referring to FIG. 4, the base 14 includes structures to facilitate determination of an item of interest in a sample. The base 14 comprises at least one lane 28 for guiding movement of a container 15 along the process path 10 responsive to movement of the disk 16. As the disk 16 moves responsive to activation of the prime mover 24, the container 15 moves along the lane 28 from one processing station to another to complete determination of the item of interest in the sample.

In the illustrated embodiment, there are a first processing lane 28 and a loading lane 30 in the process path 10. Complimentary portions of the lanes 28 and 30 are formed in both the cover 12 and the base 14. Because these two lanes 28 and 30 are substantially concentric, the desk 16, which is adjacent to both lanes 28 and 30, and its slots 18 are dimensioned to accept and to support containers 15 disposed in both the process lane 28 and the loading lane 30 at substantially the same circumferential position, while being radially offset, on the disk 16. In an exemplary embodiment, the lanes 28 and 30 have a width of about 0.279 inches at the top and have a draft angle of about 1.5 degrees.

Figure 18A:
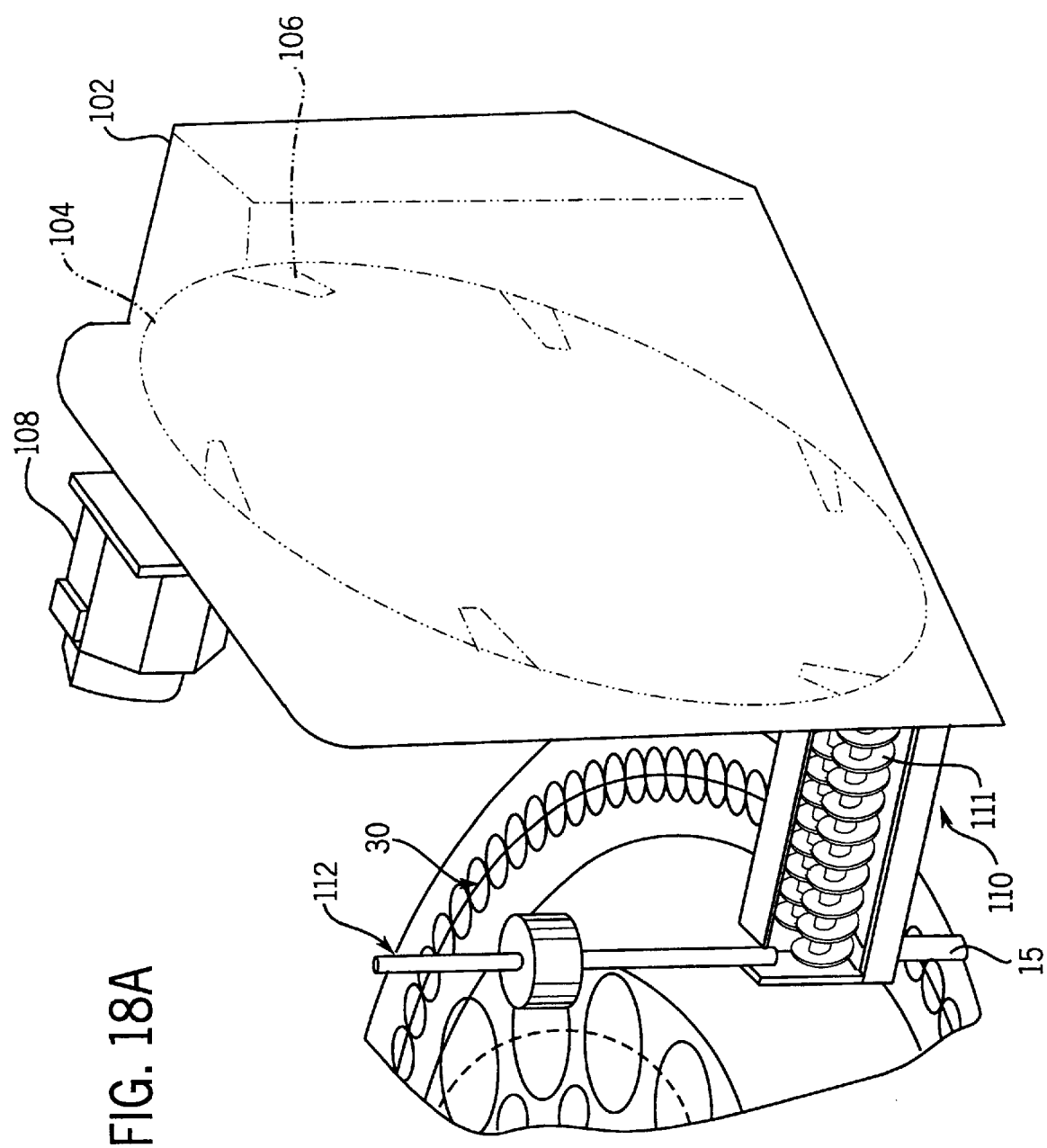
Figure 18C:
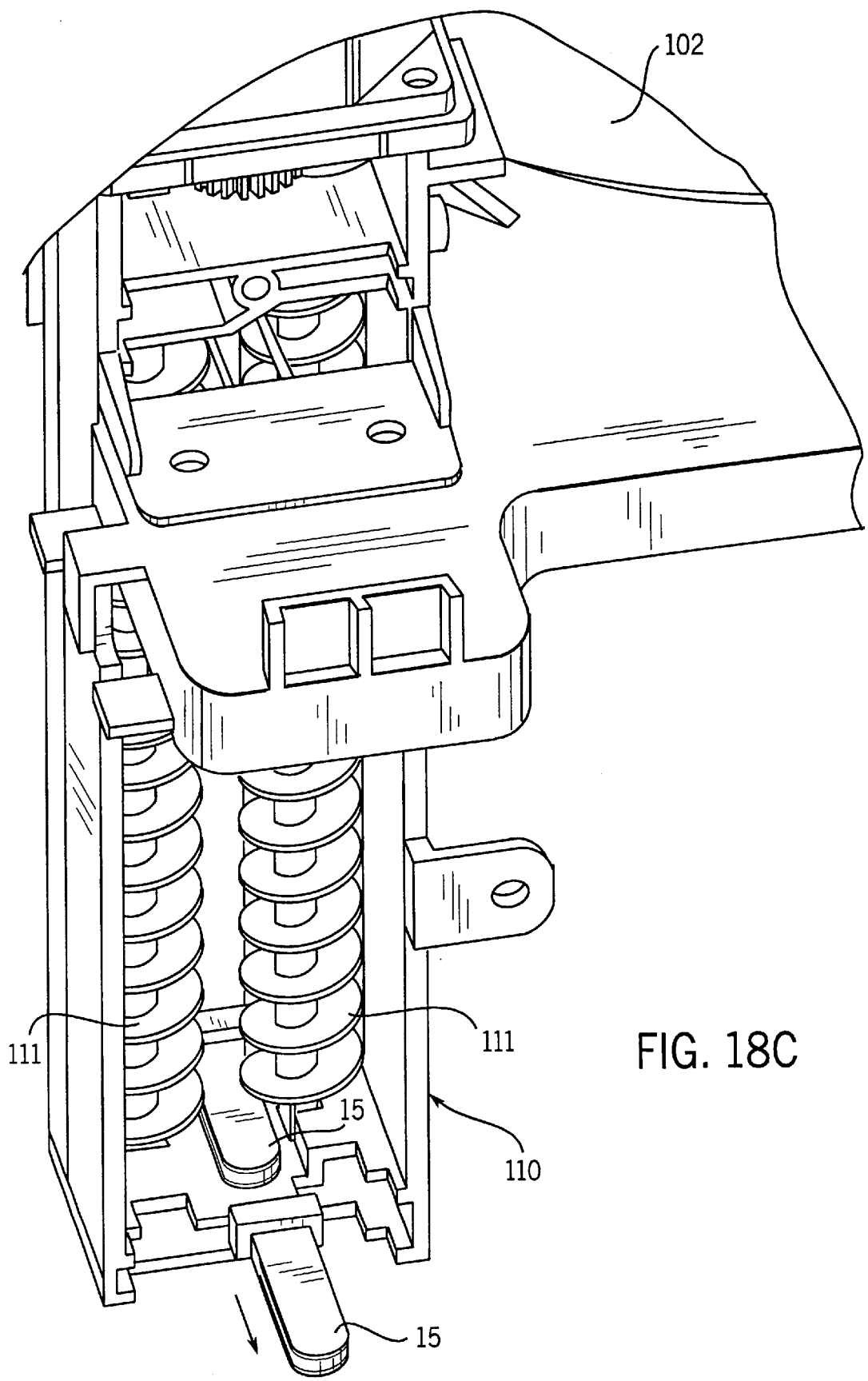

As shown in FIGS. 18A, 18B and 18C, in one embodiment, the loading lane 30 accepts and orients containers 15 from a container 15 supply or hopper 102. A disk 104 including a projection 106 is moved within the hopper 102 by a prime mover 108. In some embodiments, structures may be included with the hopper 102, such as a baffle for directing container 15 movement within the hopper 102 responsive to disk 104 movement, an "inherent flat spring" actuated by a cam driven mechanism associated with the disk 104 to move containers 15 within the hopper 102, and the like, to facilitate movement of the containers 15. As the disk 104 moves within the hopper 102, the projection 106 is inserted through the top surface 42 of a container 15 in the hopper 102. The projection 106 carries the container 15 toward a loading mechanism 110, which may include a mover 111, such as a barrel cam and the like, for moving a container 15 from the hopper 102 toward the loading lane 30. As the container 15 approaches the loading lane 30, in one embodiment, another mover 112, such as a solenoid-driven rod and the like, moves the container 15 into a slot 18 in the disk 16 at the loading lane 30. Alternatively, the container 15 may, move from an end of the mover 111 into a slot 18 in the disk 16 at the loading lane 30 under the influence of gravity.

In an exemplary embodiment, the hooper 102 is made from Lexan WR2210 (GE Plastics of Pittsfield, Mass.) with a black SPI B1 finish and has a volume substantially within the range of about 396 to about 540 cubic inches, thereby allowing the hopper 102 to hold approximately 1000 containers 15. The disk 104 is made from Lexan 500 with a finish of gray SPI B1 and the projection 106 is made from Lexan WR2210 with a finish of black SPI B1. The disk 104 includes four projection 106 mounts spaced equidistantly along a circumference of the disk 104, i.e. every 90 degrees, at a radius of about 4.5 inches from a center of the disk 102. To assist movement of containers 15 within the hopper 102, the disk 102 includes a plurality, such as four, of nubs having a spherical radius of about 0.165 inches spaced equidistantly along a circumference of the disk 104, i.e. every 90 degrees, at a radius of about 3.312 inches from a center of the disk 102. The projection 106 has a nominal thickness of about 0.1 inches and a length of about 0.9 inches. The projection 106 is aligned substantially tangentially to a 4.5 inch radius of the disk 102. The mover 108 may be No. 78431-101 from Pacific Scientific of Elgin, Ill. The mover 111 includes a screw made from Delrin 500 having a black SPI B1 finish. The screw is about 7.126 inches long and has 18 threads of a diameter measuring about 0.706 inches and of a pitch of about 0.394 inches. The screw is connected to a drive gear made from Celcon M90 having a finish of black SPI B1. The drive gear is an involute gear having 24 teeth with a diametral pitch of about 32, a pressure angle of about 20 degrees and a pitch diameter of about 0.75 inches. The mover 112 may be No. 78851-102 available from Haydon Switch & Instrument of Waterbury, Conn. In other embodiments, No. 78425-101 available from SPM/Portland of Hillsboro, Oreg. may be used for some of the components.

Figure 7A:
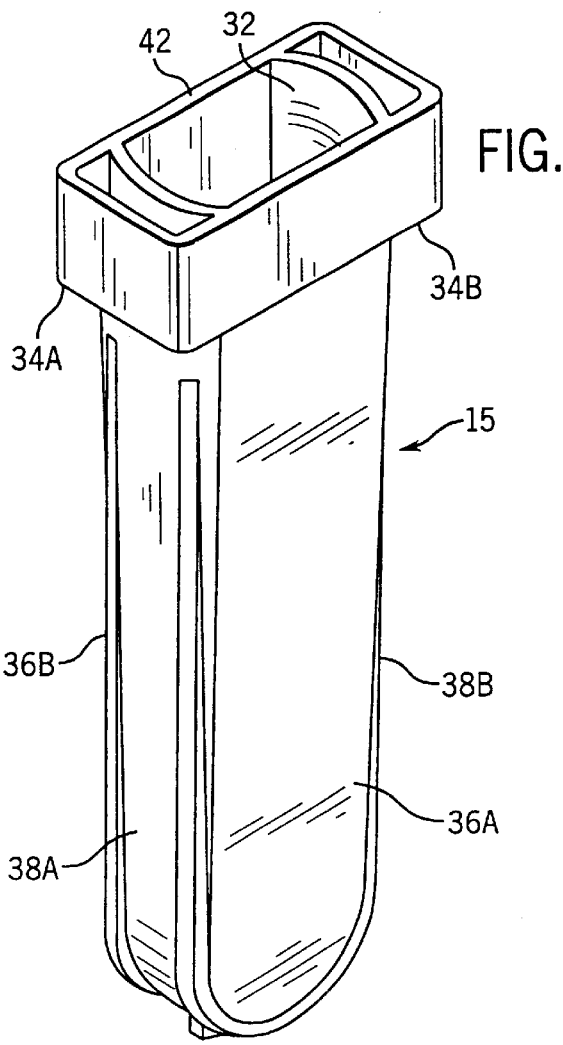
FIG. 7A is a perspective view of a container for use with the component of FIG. 1.
Figure 7B:
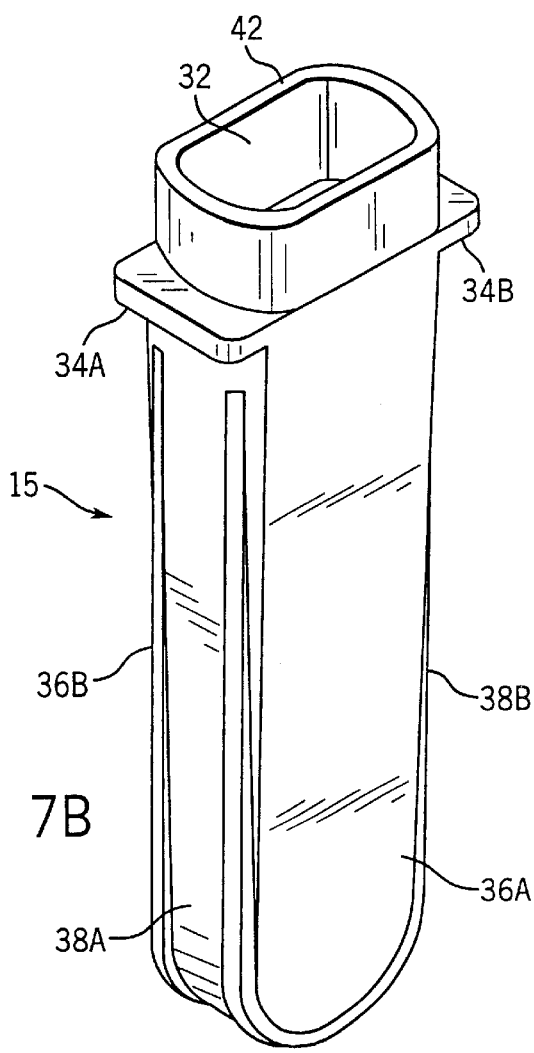
FIG. 7B is a perspective view of another container for use with the component of FIG. 1.

As shown in FIGS. 7A and 7B, the container 15 includes a sample receiving chamber 32 and a pair of support surfaces 34A and 34B connected with the sample receiving chamber 32. As shown in FIG. 8, the support surfaces 34A and 34B rest on portions of the disk 16 which bound the slot 18. The chamber 32 is formed by two sets of side walis 36A, 36B, 38A and 38B and a bottom wall 40. In an exemplary embodiment, the largest external distance between the side walls 36A and 36B, which have a rib width of about 0.020 inches, is about 0.26 inches, the largest external distance between the side walls 38A and 38B is about 0.44 inches, the support surfaces 34A and 34B extend a distance measuring about 0.085 inches from the side walls 38A and 38B, respectively, the maximum length of the container 15 is about 1.445 inches, an open end of the sample receiving chamber 32 measures about 0.391 inches by about 0.219 inches, a nominal thickness of the walls 36A, 36B, 38A and 38B is about 0.030 inches, an inside depth of the sample receiving chamber 32 is about 1.34 inches having a volume of about 1.4 ml and a volume of the sample receiving chamber 32 at a location, from which determination measurements are made, measuring about 0.699 inches from a bottom of the container 15 is about 0.45 ml. A top surface 42 of the container 15 is located a distance measuring about 0.18 inches from the support surfaces 34A and 34B. The container 15 may be made from Escorene 3345-E5 (Exxon, Houston, Tex.) or Montell PD701N (Wilmington, Del.) with an internal finish of polished SPE/SPE 1 B-2.

Returning to FIGS. 4 and 8, cooperation among the container 15, the slots 18 in the disk 16 and the lanes 28 and 30 facilitate movement of the container 15 along the process path 10. Specifically, the dimensions of the container 15, the slots 18 and the lanes 28 and 30 are predetermined such that the support surfaces 34A and 34B of the container 15 radially slidingly engage the disk 16 adjacent to the slot 18 in which the container 15 is disposed while the container 15 itself is restrained from rotation within the slot 18. In one embodiment, the process lane 28 has a radius of about 27.6 inches and a width of about 0.28 inches while the loading lane 30 has a smaller radius but a similar width. The container 15 is disposed such that axes of the side walls 36A and 36B are positioned substantially radially with respect to the process path 10 and the support surfaces 34A and 34B are aligned substantially circumferentially with respect to the process path 10. In this manner, as the disk 16 moves responsive to activation of the prime mover 24, the container 15 within the slot 18 moves substantially tangentially to the process path 10 within the lanes 28 and 30.

As the process path 10 may be used with biological samples, it is desirable to maintain the process path 10, or portions thereof, at a suitable temperature, such as 37 degrees Celsius, to facilitate determination of the item of interest. Thus, a heater (not shown), such as an electric heater and the like, may be thermally associated with the process path 10. In an exemplary embodiment, a plurality of electric resistive flexible strip heaters may be applied, such as by a suitable adhesive and the like, to the cover 12 and/or the base 14 of the process path 10. These heaters apply sufficient thermal energy to the process path 10 such that the contents of the container 15 is maintained at the desired temperature. Also, because the loading lane 30 is part of the process path 10, it is possible to bring the container 15 to the desired temperature prior to addition of anything to the container 15. For example, if determination of an item of interest in a sample is performed optimally at a given temperature, the container 15 in the loading lane 30 can be brought to that given temperature at a certain time period after introduction of the container 15 from the hopper to the loading lane 30 but before the container 15 is needed to perform the desired determination. Suitable temperature control devices, such as thermistors and the like, are also provided along the process path 10. Additionally, in some embodiments, materials, such as reagents and the like, to be added to the container 15 may be heated prior to addition to the container 15. In some cases, the material delivery apparatus, such as a fluid conduit and the like, may be associated with appropriate heaters and heat sensors.

Figure 10:
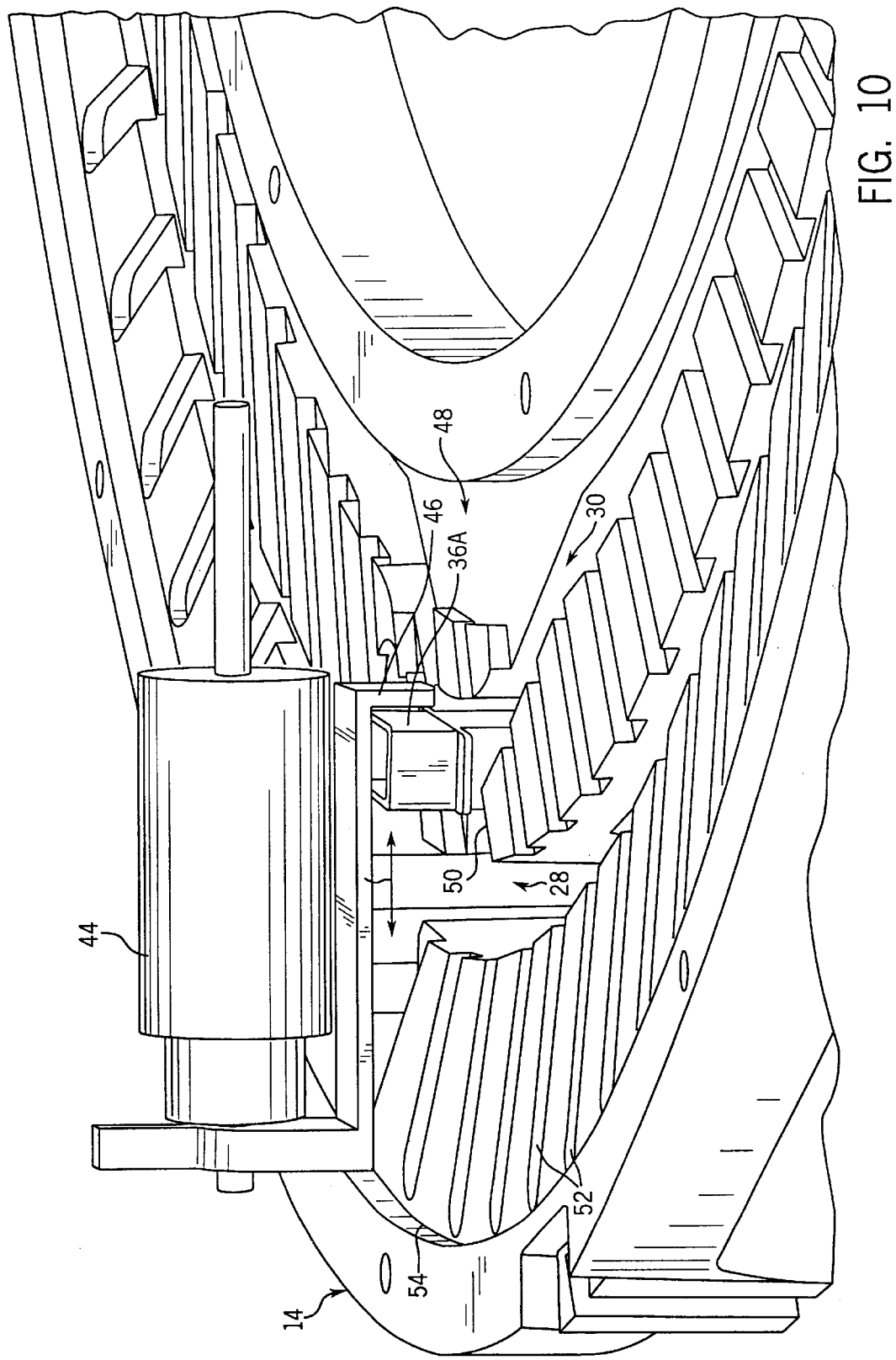
FIG. 10 is substantially similar to FIG. 9 but shows another portion oft the component of FIG. 1.

When a container 15 is needed to perform a given item of interest determination, the container 15 is moved from the loading lane 30 to the process lane 28. This function is performed at location 48 shown at FIG. 4 To move the container 15 from the loading lane 30 toward the process lane 28, as shown in FIG. 10, a prime mover 44, mounted on the process path 10, is operated. A container 15 engaging member 46 operatively connected with the prime mover 44 bears against the side wall 36A of the container 15 and moves the container 15 radially outward with respect to the disk 16 within the slot 18 from the loading lane 30 towards the process lane 28 responsive to activation of the prime mover 44. In an exemplary embodiment, the member 46 is made from 6061-T6 aluminum with a MIL-A-63576, Type I finish. The member 46 may include structures, such as a slot, which mate with complimentary structures, such as a pin, on the prime mover 44 to provide desired alignment of the mover 44 and the arm 46 and to limit undesired movement, such as rotation, of the member 46. Operation of the prime mover 44 causes the member 46 to move a distance of about 0.5 inches with a minimum starting force of about 7.08/0.25 gm/oz and a minimum ending force of about 56.7/2.0 gm/oz.

To accommodate movement of the container 15, a passageway 50 is formed on the cover 12 and the base 14 connecting the process lane 28 with the loading lane 30. Once the container 15 is in the process lane 28, the prime mover 44 moves the container 15 engaging member 46 away from the container 15 just moved to a waiting position to move another container 15 from the loading lane 30 toward the process lane 28. In an exemplary embodiment, the prime mover 44 is a solenoid, a pneumatically actuated motor, a linear positioner or the like. In a particular embodiment, the prime mover 44 is an electric solenoid with its windings modified such that the solenoid travel occurs without splashing or spilling of container 15 contents.

Now that the container 15 has been moved from the loading lane 30 to the process lane 28, movement of the disk 16 causes the container 15 to move along the process lane 28 for performance of determination of an item of interest in a sample. In some cases, the sample, such as blood or other bodily fluids, added to the container 15 is in liquid form. Also, in some cases, other substances, such as reagents and the like, are added to the sample in the container 15 during determination of an item of interest in the sample. These other substances may also be in liquid form.

As these liquids are added to the container 15 it is possible that some of the liquids may not end up within the container 15 but may be disposed on the disk 16 or other portions of the process path 10. To substantially remove these liquids, drain ducts 52 are provided on the base 14 of the process path 10. These drain ducts 52 are recessed from a groove 54 on the base 14 in which the disk 16 is disposed. In an exemplary embodiment, the drain ducts 52, about 112 in number, are equidistantly spaced along a circumference of the base 14, recess a distance of about 0.125 inches from the groove 54, have an internal angle of about 90 degrees and are about 0.05 inches deep and about 0.1875 inches wide. In some embodiments, the drain ducts 52 may be inclined toward the process lane 28 such that liquid within the drain ducts 52 will move under the influence of gravity toward and into the process lane 28. In the illustrated embodiment, the drain ducts 52 are oriented in an expected direction of disk 16 rotation. In this embodiment, liquid movement within the drain ducts 52 is encouraged by movement of the disk 16. Similar drain ducts 52 may be formed on the cover 12. To facilitate substantial removal of the liquids from the process lane 28, drain holes 56 are provided in he base 14 at various locations along bottom portions of the process lane 28.

The process of determining an item of interest in a sample comprises a number of steps. However, given the specific item of interest to be determined, different steps are to be performed. For instance, for determination of a first item of interest, three process steps are to be performed, whereas for a second item of interest, only two process steps are to be performed. These process steps may include, for example, solid,/liquid phase (for example, magnetic) separation, aspiration of container 15 contents, container 15 contents washing, etc. To offer determination of both the first and second items of interest, the process path 10 includes structures for selective automated performance of process steps. However, it is to be noted that the process path 10 includes all structures necessary to perform all process steps for determining a predetermined set of items of interest.

At at least one location along the process lane 28, structures or elements for providing selective automated performance of a determination of item of interest process step are disposed. As shown in FIG. 4, in one embodiment, these structures or elements are located in a bypass region of the process path 10. In the illustrated embodiment, the process path 10 includes three bypass regions 58A, 58B and 58C. At the bypass regions 58A, 58B and 58C, the process lane 28 is radially expanded with respect to other portions of the process lane 28. In an exemplary embodiment, the process lane 28 at the bypass regions 58A, 58B and 58C is about 0.65 inches wide radially. The radial expansion of the process lane 28 at the bypass regions 58A, 58B and 58C allows the container 15 to be positioned at multiple places longitudinally along the slot 18 and radially with respect to the disk 16 at the bypass regions 58A, 58B and 58C. Depending on the position of the container 15 within the slot 18 in the disk 16, the container 15 may or may not participate in the item of interest determination process step performed at the bypass regions 58A, 58B and 58C.

In an alternate embodiment, the structures or elements for providing selective automated performance of a determination of item of interest process step may include routines, such as those embodied in software, hardware and the like, for selectively activating or deactivating certain process path 10 elements, such as a wash zone and the like, selectively moving process path 10 elements into and out of a process step performance position with respect to the process path 10, such as moving a magnet and the like, or any appropriate combination of the methods discussed herein.

Figure 5A:
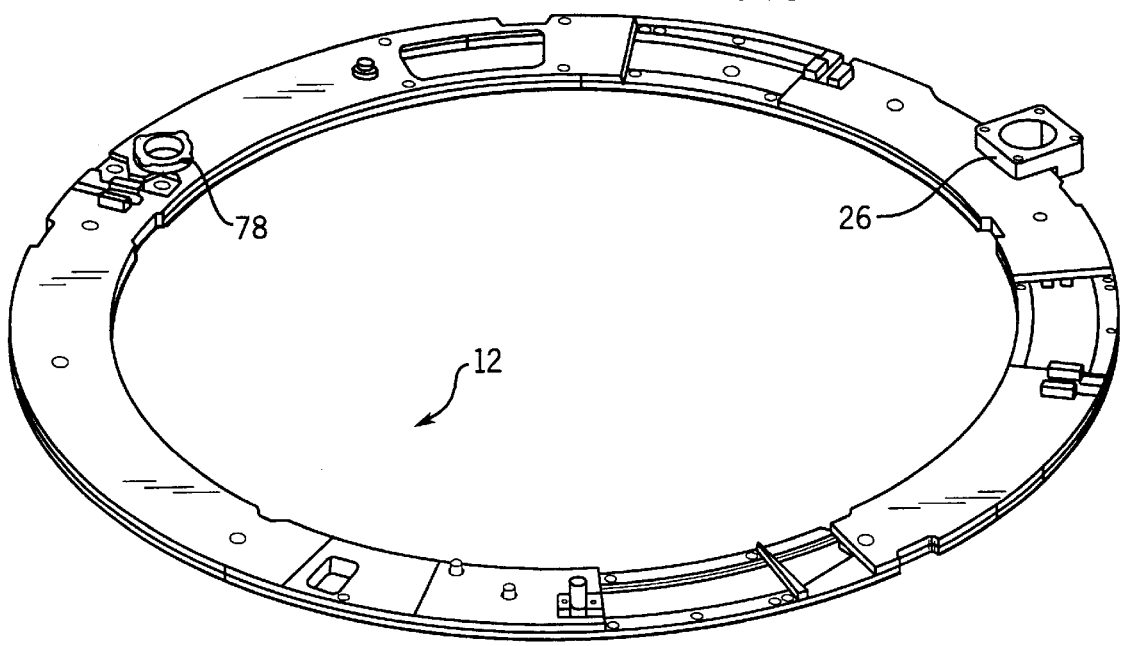
FIGS. 5A and 5B show another element of the component of FIG. 1 which is connected with the structure shown in FIG. 2.
Figure 5B:
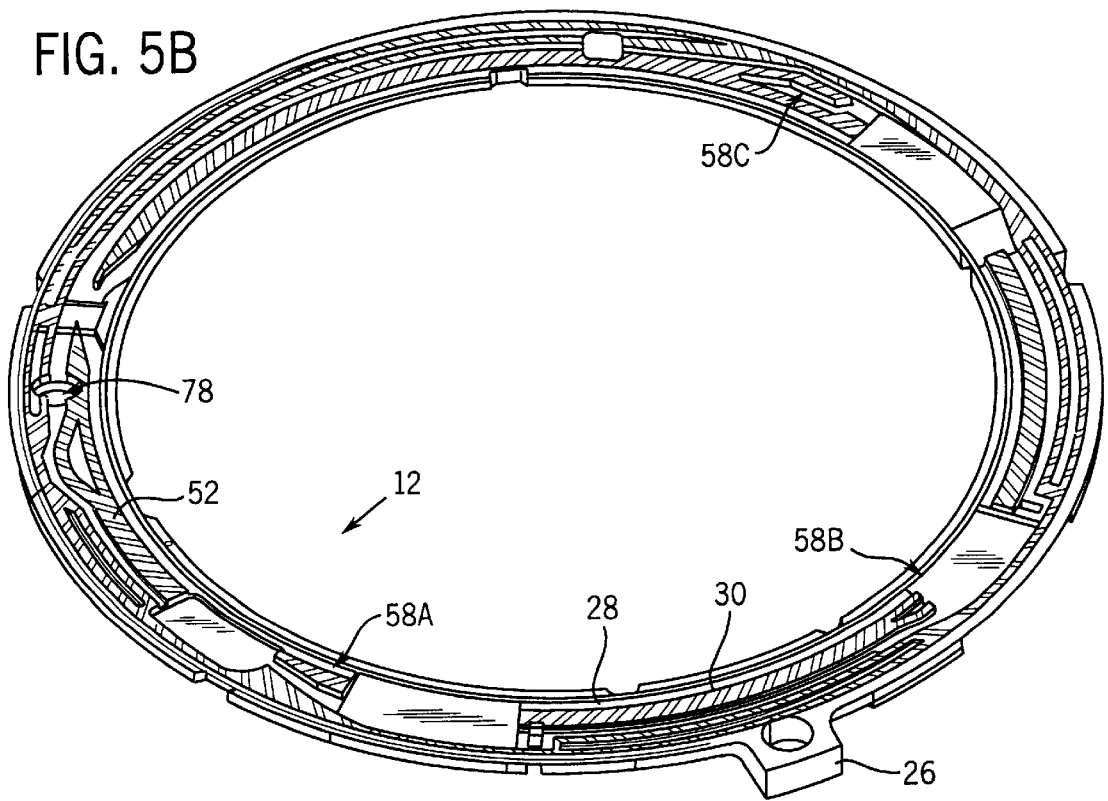

The cover 12 also includes structures forming the bypass regions 58A, 58B and 58C on the process path 10. As shown in FIGS. 5A and 5B, a wall 60 on the cover 12 separates the process lane 28 on the cover 12 at the bypass regions 58A, 58B and 58C into a process step performance lane 62 and a process step avoidance lane 64 offset radially on the cover 12. The wall 60 engages a portion of the side walls 36A and 36B adjacent of top surface 42 of the container 15 to guide the container 15 through either the process step performance lane 62 or the process path avoidance lane 64.

Figure 9:
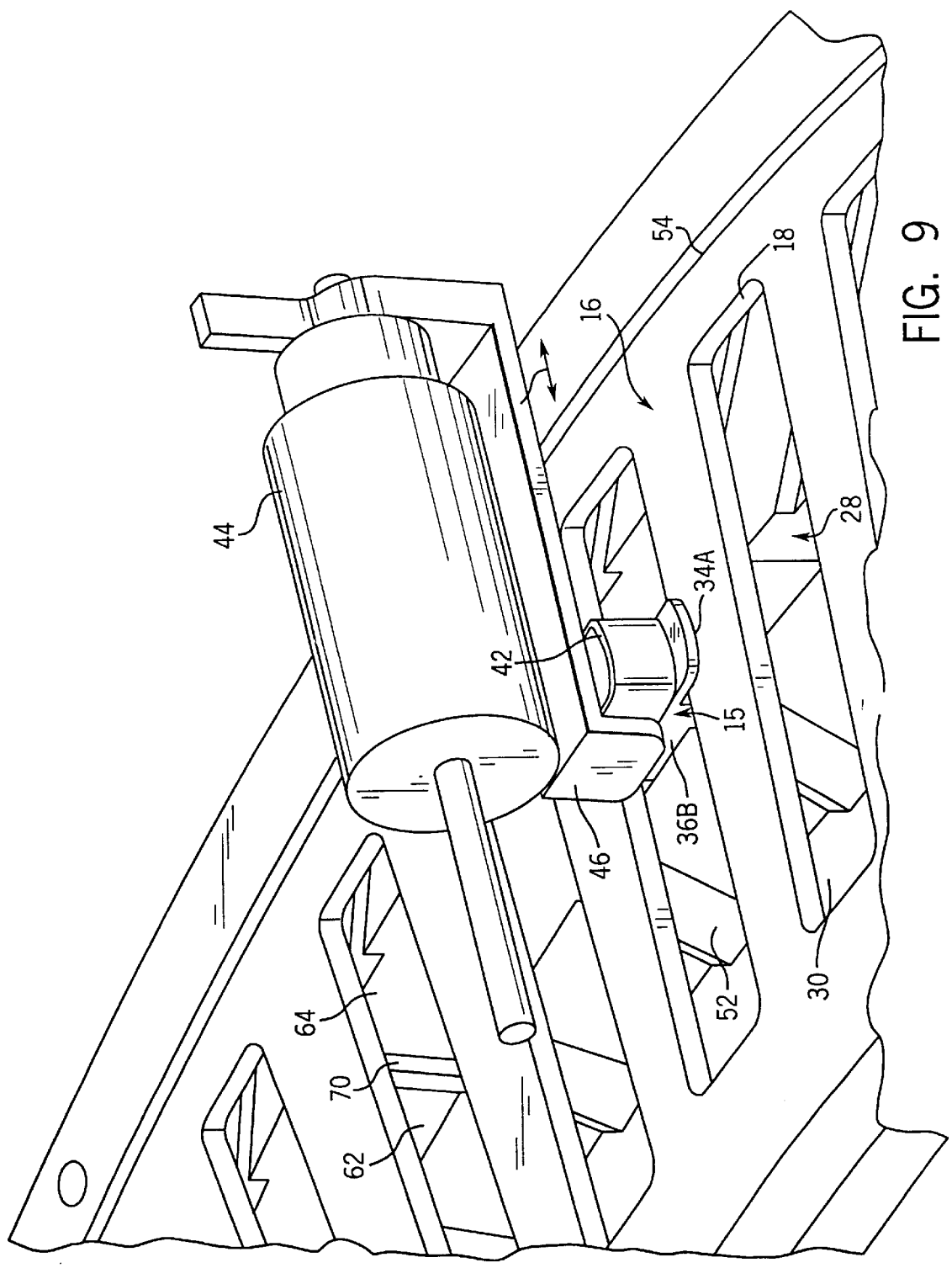
FIG. 9 is an enlarged sectional view, substantially similar to that of FIG. 8, of another portion of the component of FIG. 1.

To encourage a desired container 15 into the desired one of the process step performance lane 62 or the process step avoidance lane 64, a prime mover 44 connected with a container engaging member 46 is provided attached to the process path 10, as shown in FIG. 9. The structure illustrated in FIG. 9 is substantially similar to the construction illustrated in FIG. 10, hence the like reference numbers. Activation of the prime mover 44 enables selective radial positioning of the container 15 at either an inner 66 or outer radial edge 68 (FIGS. 5A and 5B) of the process lane 28. Once so positioned, advancement of she disk 16 with respect to the base 14 moves the container 15 into the preselected one of the process step performance lane 62 or the process step avoidance lane 64.

In some embodiments, the prime mover 44, and/or the wall 60 may be constructed to take advantage of natural movement of the container 15 in the process lane 16. For instance, the container 15 may tend to move radially outwardly along the process lane 28. In this case, the prime mover 44 and/or the wall 60 may be constructed such that a container 15 moved toward the process step avoidance lane 64 moves toward that lane 64 under centrifugal force without any assistance from the prime mover 44. In this case, the prime mover 44 would only act on a container 15 to be moved into the process step performance lane 62.

In the illustrated embodiment, the bypass regions 58A, 58B and 58C are positioned along the process lane 28 dependent upon the anticipated frequency of performance and avoidance of a particular process step. This frequency is, in turn, dependent upon a particular step of determinations of items of interest to be performed with the process path 10. Also, depending upon the determinations to be performed, there may be more or less bypass regions 58A, 58B and 58C provided.

Illustrating further by example, the process lane 28 diverges radially prior to entering the bypass region 58A (FIGS. 5A and 5B). The process lane 28 enters the bypass region 58A along its outer radial edge. Since performance of the process step occurs at the inboard process step performance lane 62 of the bypass region 58A, the prime mover 44 associated with the bypass region 58A moves the container 15 radially inward toward the process step performance lane 62 only if performance of this process step were desired. If performance of this process step were not desired, then the prime mover 44 would not be activated and the container 15 would remain on the outer radius surface of the process lane 28 and move into the process step avoidance lane 64 upon movement of the disk 16. This construction favors performance of a set of determinations where performance of the relevant process step is required for a minority of the determinations to be performed.

If the set of determinations were to change such that performance of the relevant process step is required for a majority of the determinations to be performed, then it may be desirable to construct the bypass region 58A substantially similarly to the bypass regions 58B and 58C. At the bypass regions 58B and 58C, the process lane 28 enters the bypass regions 58B and 58C at its inner radial edge. Thus, if the prime mover 44 is not activated, then the container 15 would move under the influence of movement of the disk 16 into the process step performance lane 62 and the process step would be performed. The prime mover 44 would be activated only to move those containers 15 that did not require performance of this process step. Of course, this would represent a minority of the determinations to be performed with the process path 10.

Once a container 15 is in one of the bypass regions 58A, 58B or 58C, movement of the container 15 through the bypass region 58A, 58B or 58C is controlled by cooperation among the disk 16, edges of the process step performance and avoidance lanes 62 and 64 and the wall 60. The container 15 moves substantially tangentially through the process path 10 under the influence of rotation of the disk 16. The position of the container 15 radially within the radially inner-most one of the process step performance lane 62 (e.g. bypass region 58A) or the process step avoidance lane 64 (e.g. bypass region 58B) is maintained by an inner radial edge of the wall 60. A radius defining this inner radial edge of the wall 60 gradually increases along the wall 60 from a first end 70 to a second end 72 thereof. The container 15 is moved radially outward as the container 15 moves through the bypass region 58A, 58B or 58C. A radius defining an inner edge of the process step performance lane 62 (e.g. bypass region 58A) and the process step avoidance lane 64 (e.g. bypass region 58B) also increases from one end of the bypass region 58A, 58B or 58C adjacent the first end 70 of the wall 60 to an opposite end of the bypass region 58A, 58B or 58C adjacent the second end 72 of the wall 60. Thus, a portion of the container 15 adjacent its top surface 42 is maintained adjacent the wall 60, thereby maintaining intended positioning of the container 15 within the bypass regions 58A, 58B and 58C.

Figure 11:
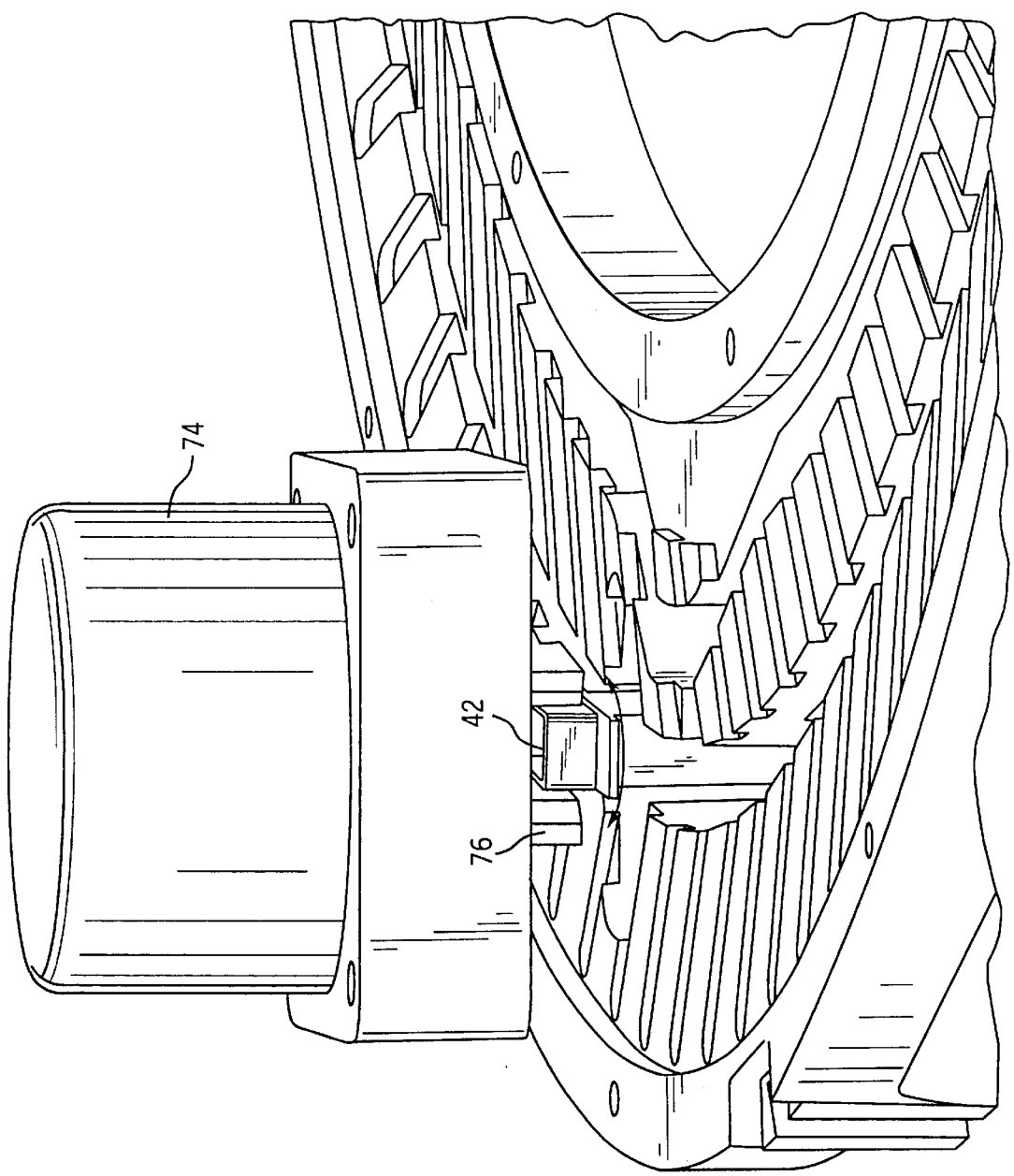
FIG. 11 is substantially similar to FIG. 10 but shows another portion of the component of FIG. 1.

Once the determination of an item of interest is complete, the relevant container 15 is removed from the process lane 28 and the process path 10 altogether. As shown in FIG. 11, a prime mover 74 is connected with the process path 10. The prime mover 74 drives a container 15 engaging surface 76 which acts on the container 15 adjacent the top surface 42 of the container 15. The prime mover 74, which may be a stepper motor and the like, drives the container engaging surface 76 to rotate the container 15 about 90 degrees with respect to the disk 16. This occurs at location 78 shown in FIG. 4. The process path 10 at the location 78 is configured to allow axial rotation of the container 15 and includes an aperture 80 having dimensions larger than corresponding dimensions of the container 15.

In an exemplary embodiment, the prime mover 74 may be a solenoid such as P/N 197855-001 BTA 2 DV 90° available from Lucas Control Systems Products of Vandalia, Ohio. The surface 76 may be made from 6061-T6 aluminum with a MIL-A-63576, Type I finish and moves approximately 90 degrees responsive to operation of the prime mover 74.

Once the container 15 has been rotated, the support surfaces 34A and 34B of the container 15 are no longer in engagement with the disk 16. Under the influence of gravity, the container 15 falls through the aperture 80 in the process path 10 into a waste receptacle (not shown). In some constructions, a chute may be provided to guide the container 15 from the process path 10 toward the waste container. In other constructions, liquid present in the container 15 may be removed from the container 15 prior to encountering the prime mover 74.

With the container 15 being removed from the process lane 28, another container 15 within the same slot 18 on the disk 16 can be moved from the loading lane 30 to the process lane 28 as soon as the relevant slot 18 reaches the location 48. In some instances, it may not be desirable to remove a container 15 from the process lane 28 once nat container 15 reaches location 78. In this case, the prime mover 74 will not be activated. Also, a container 15 disposed within the same slot 18 on the disk 16 but in the loading lane 30 Will not be moved from the loading lane 30 to the process lane 28 when the relevant slot 18 reaches location 48.

Figure 13:
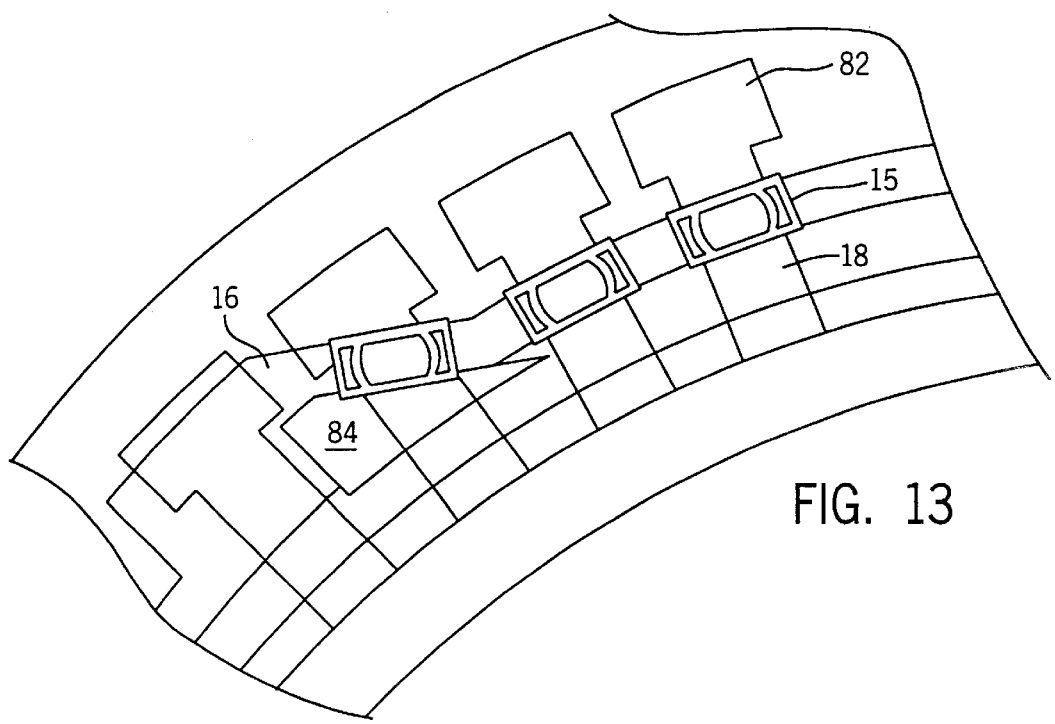
FIG. 13 is an enlarged sectional view of a section of another embodiment of the component shown in FIG. 1.

In an alternative embodiment shown in FIGS. 13 and 19, the disk 16 is constructed to facilitate removal of a container 15 from the process path 10. In this embodiment, the slots 18 on the disk 16 include an enlarged container 15 removal area 82. Also, a diverter 84 is disposed in the process lane 28 adjacent to the location 78. The diverter 84, along with movement of the disk 16, urges the container 15 radially outward with respect to the disk 16 toward the container removal area 82 of the slot 18. The container removal area 82 is wider than the remainder of the slot 18 such that, when the container 15 reaches the container removal area 82 of the slot 18, gravity causes the container 15 to fall from the disk 16 and the process path 10 through the aperture 80 and into the waste receptacle. However, this embodiment does not allow a container 15 to pass the location 78 and still remain with the disk 16. But, if it were desirable to allow the container 15 to remain with the disk 16 in this embodiment, then the diverter 84 may be replaced with a prime mover, similar to the prime mover 44, to move the container 15 within the slot 18 toward the container removal area 82.

Another construction of the disk 16, the slot 18 and the container removal area 82 is shown in FIG. 19. This construction functions in a manner substantially similar to that of FIG. 13. It is to be noted that, in the embodiment illustrated in FIG. 19, an, end of the process lane 28 is defined by the aperture 80.

Additional features may be incorporated into the process path 10 as desired. For example, liquid level sensing devices, such as radio frequency liquid level sense devices and the like, may be incorporated at positions along the process path 10 where liquid movement may occur. Also, any suitable structures, such as any of those disclosed in U.S. Pat. Nos. 5,358,691, 5,536,471 and 5,482,861 may be added, sometimes with appropriate modifications. Those patents are assigned to the assignee of the present case and the disclosures thereof are incorporated herein in their entirety by this reference.

It may also be desirable to construct the process lane 28 to reduce light in portions of the process lane 28. In one embodiment, the process lane 28 is constructed such that there is a radial divergence of that lane 28 prior to and following any position on the process path 10 where light, such as chemiluminescently generated light, measurements are performed. Such a radial divergence of the process lane 28 may increase the sensitivity of the light measurer by reducing introduction of stray or ambient light into the light measuring position of the process lane 28.

The process path 10 described above allows sequential automated performance of multiple determination of item of interest process steps. The motion of a container 15 along the process lane 28 may be executed in discrete steps, that is discrete with respect to time and with respect to position along the process lane 28. At regular time intervals, such as about 18 seconds, the disk 16 rotates a distance substantially equal to the angular distance between two adjacent slots 18. This rotation causes each container 15 to move to the position along the process path 10 previously occupied by the container 15 in the adjacent slot 18. The disk 16 and the container 15 remain stationary for a remainder of the regular time period prior to the next rotation or indexing of the disk 16. The process lane 28 may be considered as having a fixed number of process positions, positions at which a process step comprising the determination of an item of interest in a sample occur, equal to the number of slots 18 in the disk 16.

In the examples described here, there are 112 slots 18 in the disk 16, and consequently the process lane 28 may be considered as having 112 process positions. The total processing time of a container 15 and its contents may be thought of as integral multiples of the index period. For example, if the index period is 18 seconds, a container 15 in the 10th process position has undergone a total of 180 seconds of processing. Similarly, a process step that is performed over 20 process positions takes a total of 360 seconds of process time on an individual container 15.

An example of process steps that may be performed during determination of an item of interest in a sample may be described by specifying the process position at which each process step occurs, as is provided in the following examples. This example may be more easily understood with reference to FIG. 16. The dotted line 129 indicates a boundary of a support on which the process path 10 is mounted.

A reagent carousel 131 is located substantially concentrically with the process path 10 and is rotatable. The reagent carousel 131 may include one or more carousels and may provide for axial rotation of individual containers, i.e. magnetic microparticle containers, disposed thereon. In one embodiment, the reagent carousel 131 may include multiple substantially concentric carousels to provide simultaneous and/or shared access of multiple containers by multiple pipette assemblies, such as assemblies 128 and 134. Such an arrangement may facilitate performance of the Formats discussed later. The reagent carousel 131 may be constructed substantially similarly to the structure disclosed in GB 2,081,118 B issued on Sep. 7, 1983, with appropriate, well known bearings and gear trains being provided as and where needed (See FIG. 24B), as disclosed on Page 3, lines 86–91 of that patent. In an exemplary embodiment, the carousel 131 may be No. 77829-101 available from SPM/Portland of Hillsboro, Oreg., with appropriate motors available from Pacific Scientific, gears from Turnamatic of Richardson, Tex. and SPM/Portland and sensors from Aromat of Rolling Meadows, Ill.

Figure 25:
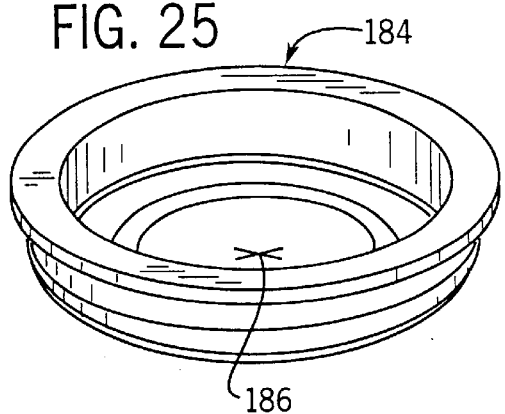
FIG. 25 is an isometric view of a seal which may be used with the containers of FIGS. 22, 23A, 23B and 23C.
Figure 29:
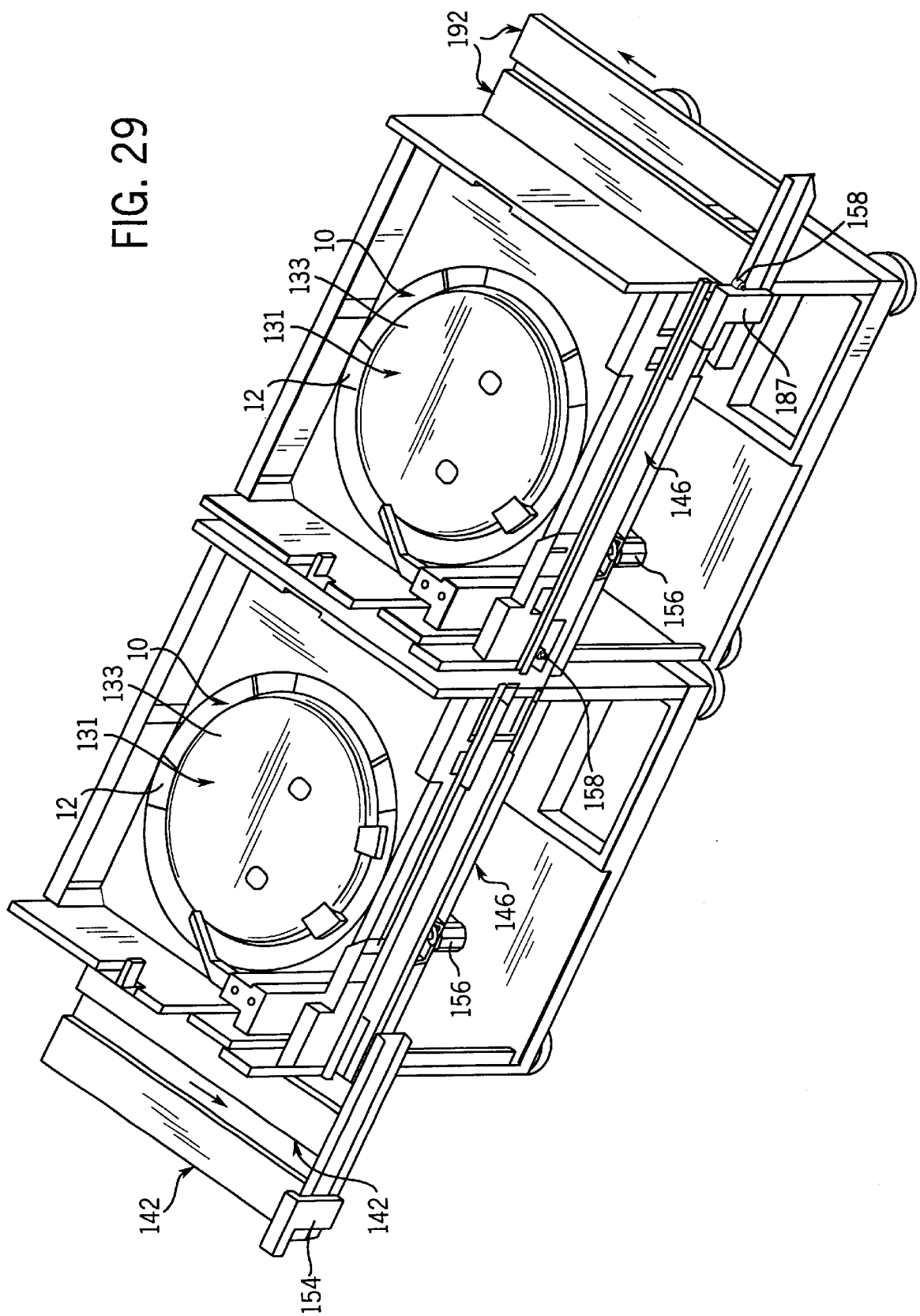
FIG. 29 is an illustration of two components of FIG. 1 joined together.

The reagent carousel may be maintained within a thermostaticly controlled environment. The thermostaticly controlled environment may be provided by an air cooling unit which provides forced cooled al to a housing 133 (FIGS. 29 and 30) containing the reagent carousel 131. In an exemplary embodiment, the housing 133 may be similar to No. 76848 available from General Pattern of Blaine, Minn. This may reduce evaporation of fluid from the containers held on the reagent carousel 131. To further reduce evaporation, open mouths of the containers may be fitted with a seal 184 as shown in FIG. 25. The seal 184 may be made of a polymeric material, such as an elastomer and the like, and may include a slit 186 for allowing a pipettor access to the interior of the container.

In one embodiment, the reagent carousel 131 supports a plurality of reagent containers. These containers may be of at least four types, such as microparticle, conjugate, determination specific diluent and pretreatment, dependent upon the type of reagent contained therein. FIGS. 22, 23A, 23B and 23C give two exemplary configurations of the containers. A bottom portion 174 of the containers 176 (FIG. 22) and 177 (FIGS. 23A, 23B and 23C) is constructed to fit with mating portions of the reagent carousel 131.

Figure 24A:
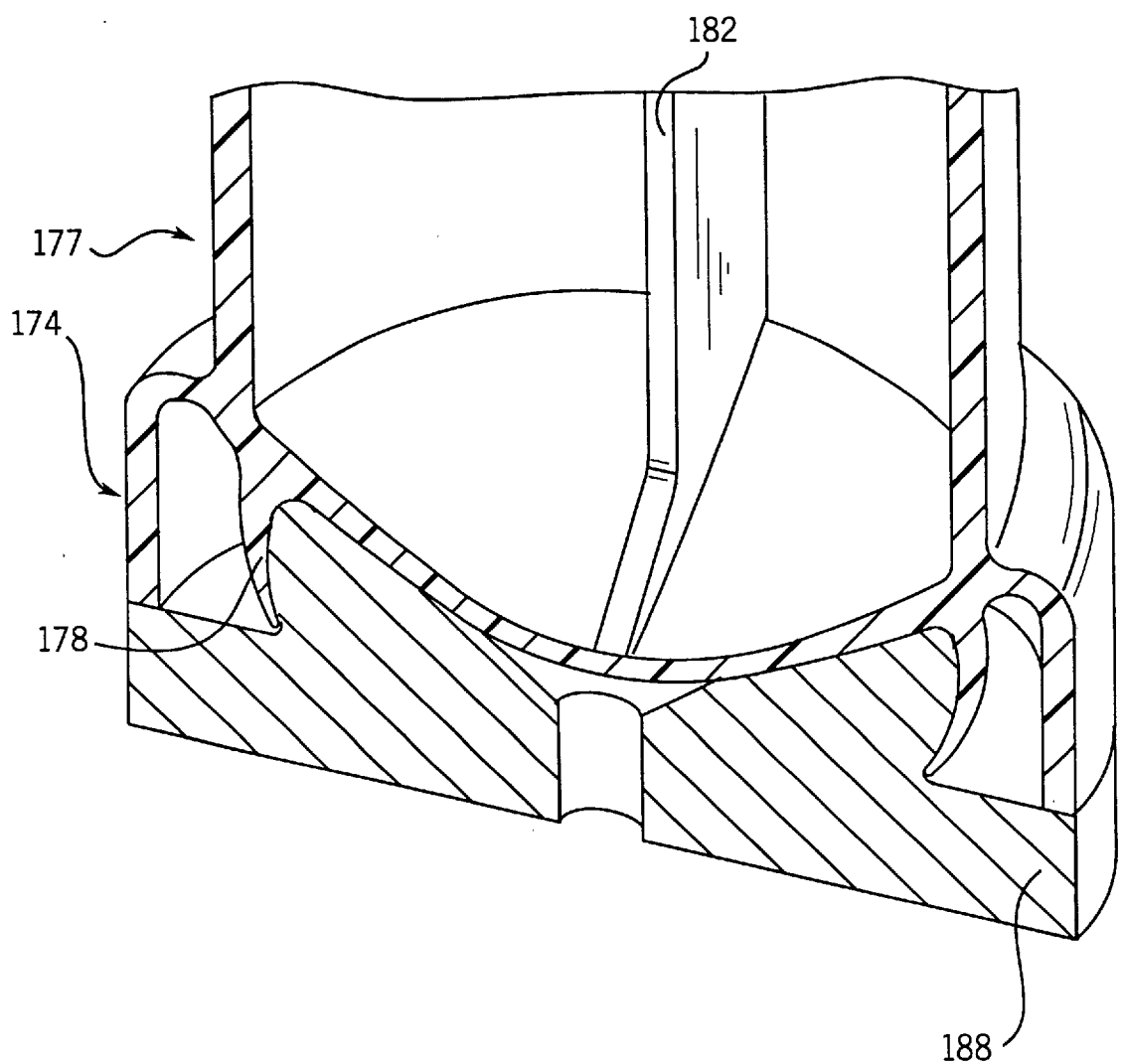
FIGS. 24A and 24B are enlarged sectional views of a portion of the container of FIGS. 23A, 23B and 23C operatively associated with a support.
Figure 24B:
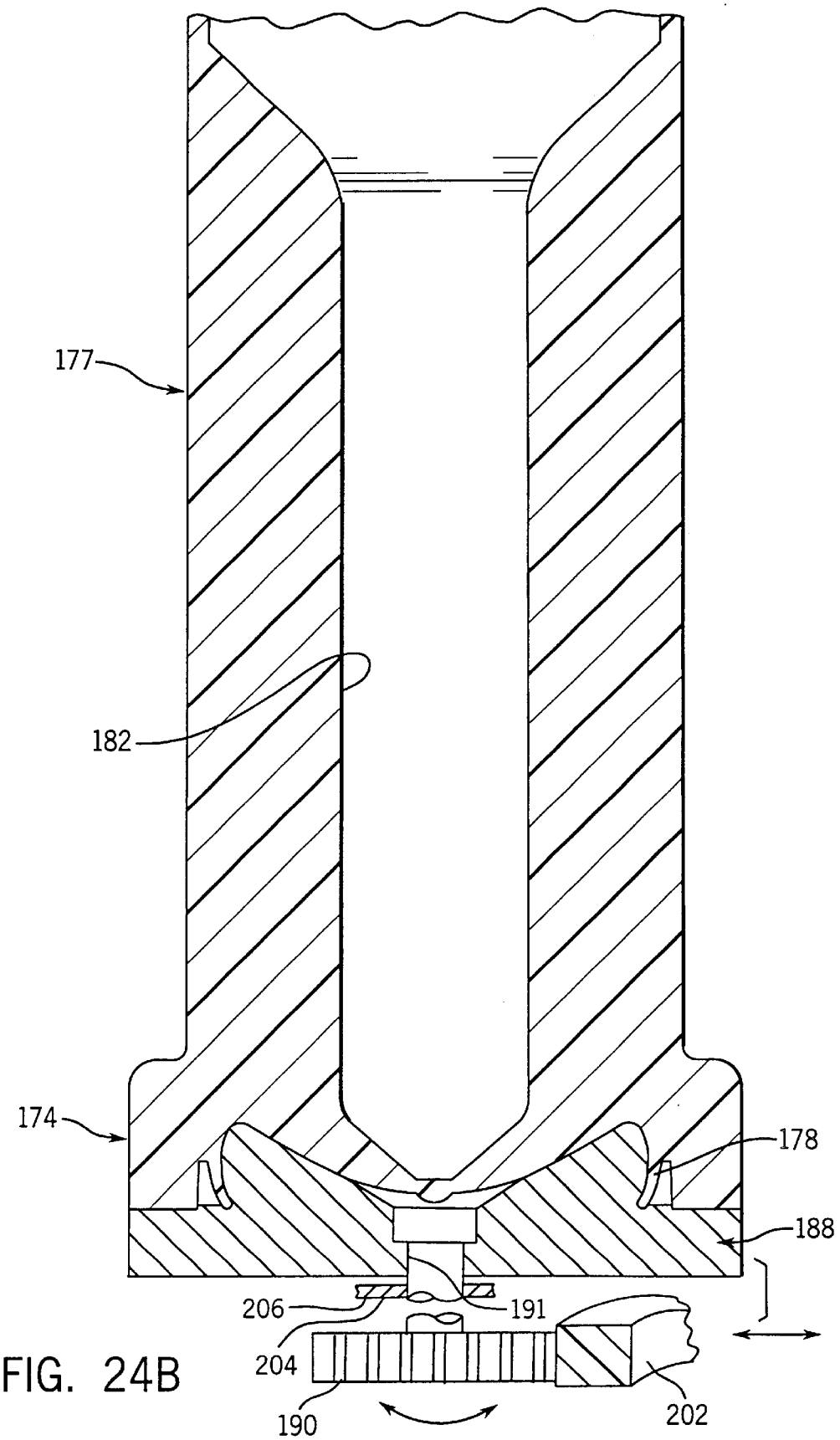

As shown more clearly in FIGS. 24A and 24B, the bottom portion 174 of the container 177 bears a projection 178 which engages a complementary portion 188 of the reagent carousel 131. The engagement between the projection 178 and the portion 188 of the reagent carousel 131 provides a user who is placing the container 177 on the reagent carousel 131 with positive feedback, i.e. tactile feel, indicative of proper positioning of the container 177 with respect to the carousel 131.

As shown in FIG. 24B, the portion 188 of the carousel 131 is operatively connected by a shaft 191 with a drive gear 190 which drivingly engages a gear 202 which is connected with a prime mover (not shown). The gear 202 engages all drive gears 190 associated with the carousel 131. Operation of the prime mover moves the gear 202 which, in turn, moves the gear 190. Movement of the gear 190 causes axial rotation, which may be bi-directional, of the portion 188 and the container 177. The shaft 191 also electrically contacts a plate 204 which is electrically connected with a conductor 206. In this manner, the plate 204 and the conductor 206, and possibly the portion 188 of the carousel 131, if it is electrically conductive, comprise a portion of a radio frequency liquid level sense mechanism with determines a fluid level inside the container 177.

To further facilitate manipulation of the container 177, a substantially annular rib 180 (FIGS. 23A, 23B and 23C) may be provided on an outer surface of the container 177. Also, if it were desirable to maintain the container contents in a substantially homogeneous state, i.e. magnetic particles substantially uniformly dispersed in a liquid medium, then at least one fin 182 (FIGS. 24A and 24B) may be provided on an interior, fluid facing surface of the container 177 to agitate container contents upon axial rotation, as discussed above, of the container 177.

Illustrating constructions of the containers and seals with specific examples, the containers may be made from DOW 30460M HDPE or Chevron 90512 HDPE with a finish of SPI A3. The fins 182 may have a finish of SPI C1. The seals may be made from Lexington Medical 3401005 EPDM. The containers may have a neck inner diameter measuring about 1.069 inches. The rib may have a thickness of about 0.025 inches, a width, from an inner wall of the container, measuring about 0.31 inches, a top geometry measuring about 45 degrees, and a bottom geometry tapering to a center at an angle of about 48 degrees. The seal may have a diameter of about 1.094 inches when installed with a container, a maximum thickness of about 0.070 inches at a centerline of the seal, and a reinforced hinge section measuring about 0.025 inches thick by about 0.062 inches deep from an underside of a pipettor contact area on the seal. The slit on the seal may comprise two slits having a length of about 0.5 inches through a center of the seal and offset about 90 degrees from each other.

Figure 21A:
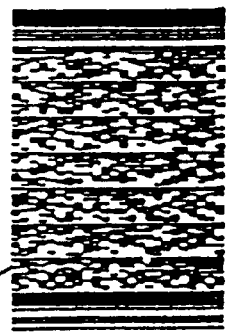
FIGS. 21A, 21B and 21C show an embodiment of a high density data carrier which may be used with the component of FIG. 1.
Figure 21B:
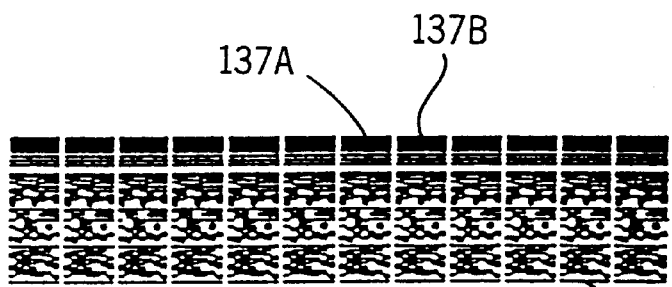
Figure 21C:
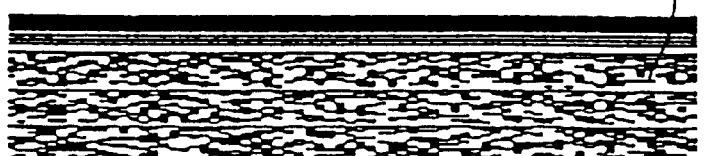
Figure 22:
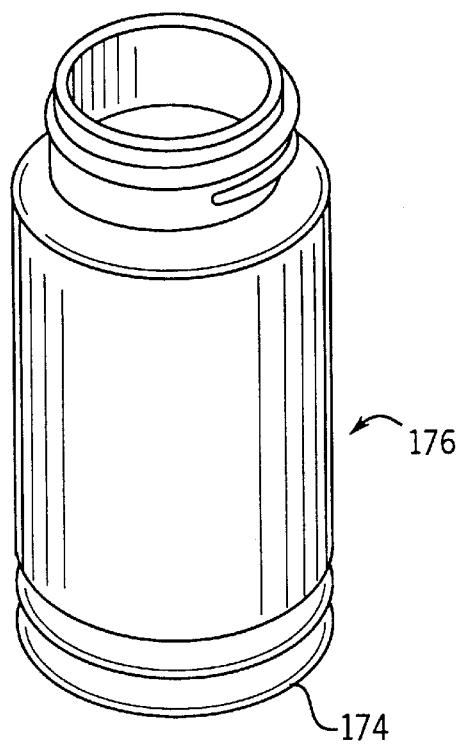
FIG. 22 is an isometric view of a container for use with the process path of FIG. 1.

To facilitate identification of the containers, at least some of the containers may bear a label 133A, 133B, or 133C, substantially similar to those shown in FIGS. 21A, 21B and 21C. The labels 133A, 133B and 133C include a high density data carrier 135A, 135B and 135C, respectively, which includes information to facilitate performance of the determinations.

In a specific embodiment, the high density data carrier 135A, 135B and 135C is a two dimensional bar code utilizing PDF 417 technology to provide desired data capacity. This technology allows for inclusion of more information than a common one dimensional bar code. Usage of such a high density data carrier 135A, 135B and 135C provides structural flexibility, i.e. individual containers for a given determination do not have to be physically joined together. The data carrier 135A, 135B and 135C contains information desirable for performance of a given determination. This information may include master lot number, container lot number, container contents, i.e. reagent, lot number and expiration date, calibration curve data, container contents type, etc. The information may also contain a serial number specific to the particular container to facilitate tracking of process path 10 resources.

In the illustrated embodiment, the data carrier 135A is used with magnetic microparticle containers and holds approximately 185 characters of information. The data carrier 135A is approximately 1.5 inches tall and about 0.75 inches wide, as viewed by the bar code reader. Because the microparticle container is rotated as discussed above, this rotation may be utilized while reading the data carrier 135A. In this case, the orientation of the data carrier 135A with respect to the bar code reader may not be important.

The data carriers 135B and 135C of the illustrated embodiment comprise two dimensional bar codes containing about 15 characters of information each. The data density of the carrier 135B and 135C is adjusted to allow the carrier 135B and 135C to be about 0.7 inches high.

Furthermore, the data carrier 135B and 135C is printed with error correction, X bar, Y bar and a column count that allows the carrier 135B and 135C to be about 3.125 inches wide. In this manner, the data carrier 135B and 135C can be disposed along an outer circumference of a container such that the carrier 135B and 135C is accessible to the bar code reader through approximately 220 to approximately 270 degrees of visibility, depending on container size. Alternatively, instead of the carrier 135B which includes only one bar code, the data carrier 135C includes a plurality of repetitions of a similar, but narrower in form bar code with gaps between adjacent code repetitions. Additionally, various modifications of the data carriers 135A, 135B and 135C are also possible. For instance, one dimensional bar codes could be used, but the surface area of the one dimensional bar code would have to be sufficient for the amount of data contained in the two dimensional bar code.

EXAMPLE

Determining an Item of Interest in a Sample

The process path 10 illustrated in FIG. 1 is utilized to perform a sequence of process steps, executed with a index period of about 18 seconds. Each index step comprises about 1 second of rotation of the disk 16 (and consequent motion of the containers 15 disposed within the disk 16) and about 17 seconds during which the containers 15 are stationary at their respective process positions. The process step performed at each process position is as follows:

| Process Position | Process Step | Description |
|---|---|---|
| 1 | Container 15 load | Container 15 moved from loading lane 30 to process lane 28 as required |
| 1 | Sample Pipettor | Sample deposited into container 15 by pipetting system 128. The sample may be obtained from position 130A or 130B which are located on appropriate conveyors sample handlers or structures associated with a laboratory automation system |
| 2 | Reagent Pipettor 1 | Reagent obtained from reagent carousel 131 deposited into container 15 by pipetting system 132. Liquid present in the pipetting system 132 may also be added to the container 15. |
| 3 | Mixer | Contents of container 15 are mixed by a device 86 imparting motion to the container 15 |
| 4–23 | Incubation | Contents of container 15 are incubated at a controlled temperature, about 37 degrees Celsius |
| 24 | Sample Pipettor | Sample may be aspirated from container contents 15 by pipetting system 128 for deposition into a second container 15 at position 1 |
| 25–39 | Incubation | Contents of container 15 are incubated at a controlled temperature |
| 40 | Bypass region 58A start | Container 15 is selectively positioned at entry to performance lane 62 or avoidance lane 64 of bypass region 58A |
| 41 | Wash zone 1 | Container 15 in performance lane 62 undergoes magnetic separation and fluid addition |
| 42 | Wash zone 1 | Container 15 in performance lane 62 undergoes magnetic separation, container 15 contents aspiration and fluid addition |
| 43 | Wash zone 1 | Container 15 in performance lane 62 undergoes magnetic separation, container 15 contents aspiration and fluid addition |
| 44 | Wash zone 1 | Container 15 in performance lane 62 undergoes magnetic separation and container 15 contents aspiration |
| 45.5 | Bypass region 58A end | Performance lane 62 and avoidance lane 64 of bypass region 58A merge (midway between positions 45 and 46) |
| 46 | Container 15 load into loading lane 30 | New containers 15 are loaded into loading lane 30 |
| 48 | Reagent Pipettor 2 | Reagent selectively deposited into container 15 by pipetting system 134 |
| 49 | Mixer | Contents of container 15 are mixed by a device 86 imparting motion to the container 15 |
| 50–62 | Incubation | Contents of container 15 are incubated at a controlled temperature |
| 63 | Bypass region 58B | Container 15 is selectively positioned at entry to performance lane 62 or avoidance lane 64 of bypass region 58B |
| 64 | Wash zone 2 | Container 15 in performance lane 62 undergoes magnetic separation and fluid addition |
| 65 | Wash zone 2 | Container 15 in performance lane 62 undergoes magnetic separation, container 15 contents aspiration and fluid addition |
| 66 | Wash zone 2 | Container 15 in performance lane 62 undergoes magnetic separation, container 15 contents aspiration and fluid addition |
| 67 | Wash zone 2 | Container 15 in performance lane 62 undergoes magnetic separation and container 15 contents aspiration |
| 68 | Bypass region 58B end | Performance and avoidance lanes 62 and 64 of bypass region 58B merge |
| 69–70 | Incubation | Contents of container 15 are incubated at a controlled temperature |
| 71 | Reagent Pipettor 2 | Reagent selectively deposited into container 15 by pipetting system 134 |
| 72 | Mixer | Contents of container 15 are selectively mixed by a device 86 imparting motion to the container 15 |
| 73–86 | Incubation | Contents of the container 15 are incubated at a controlled temperature |
| 75 | Motor/Encoder | Gear 22 on prime mover 24 engages teeth 20 on disk 16 at this position |
| 77.5 | Home Sensor | Electrical, magnetic, optical, or other sensor 136 is present to generate signal corresponding to the position of the disk 16 |
| 86 | Bypass region 58C | Container 15 is selectively positioned at entry to performance lane 62 or avoidance lane 64 of bypass region 58C |
| 87 | Wash zone 3 | Container 15 in performance lane 62 undergoes magnetic separation and fluid addition |

-continued

| Process Position | Process Step | Description |
|---|---|---|
| 88 | Wash zone 3 | Container 15 in performance lane 62 undergoes magnetic separation, container 15 contents aspiration and fluid addition |
| 89 | Wash zone 3 | Container 15 in performance lane 62 undergoes magnetic separation, container 15 contents aspiration and fluid addition |
| 90 | Wash zone 3 | Container 15 in performance lane 62 undergoes magnetic separation, and container 15 contents aspiration |
| 91 | Bypass region 58C end | Performance and avoidance lanes 62 and 64 of bypass region 58C merge |
| 91–93 | Incubation | Contents of container 15 are incubated at controlled temperature |
| 94 | Pre-Trigger and Mixer | Reagent added to container 15 and mechanically mixed |
| 95–97 | Incubation | Contents of container 15 are incubated at controlled temperature |
| 98 | Shutter, reader, and trigger | Indicator reaction (such as chemiluminescent reaction) triggered and read with magnetic particles pulled out of solution with magnet. Shutter blocks light. |
| 99 | Magnet | Magnetic particles are held at a wall of the container 15 |
| 100 | Liquid Waste Aspirate | Magnetic particles are held at a wall of the container 15 and all liquid in container 15 is aspirated and discarded |
| 109 | Container 15 unload | Container 15 selectively removed from process lane 28 |
| 111 | Container 15 unload sensor | System optically verifies that slot 18 in process lane 28 is vacant prior to loading of second container 15 |

Figure 16:
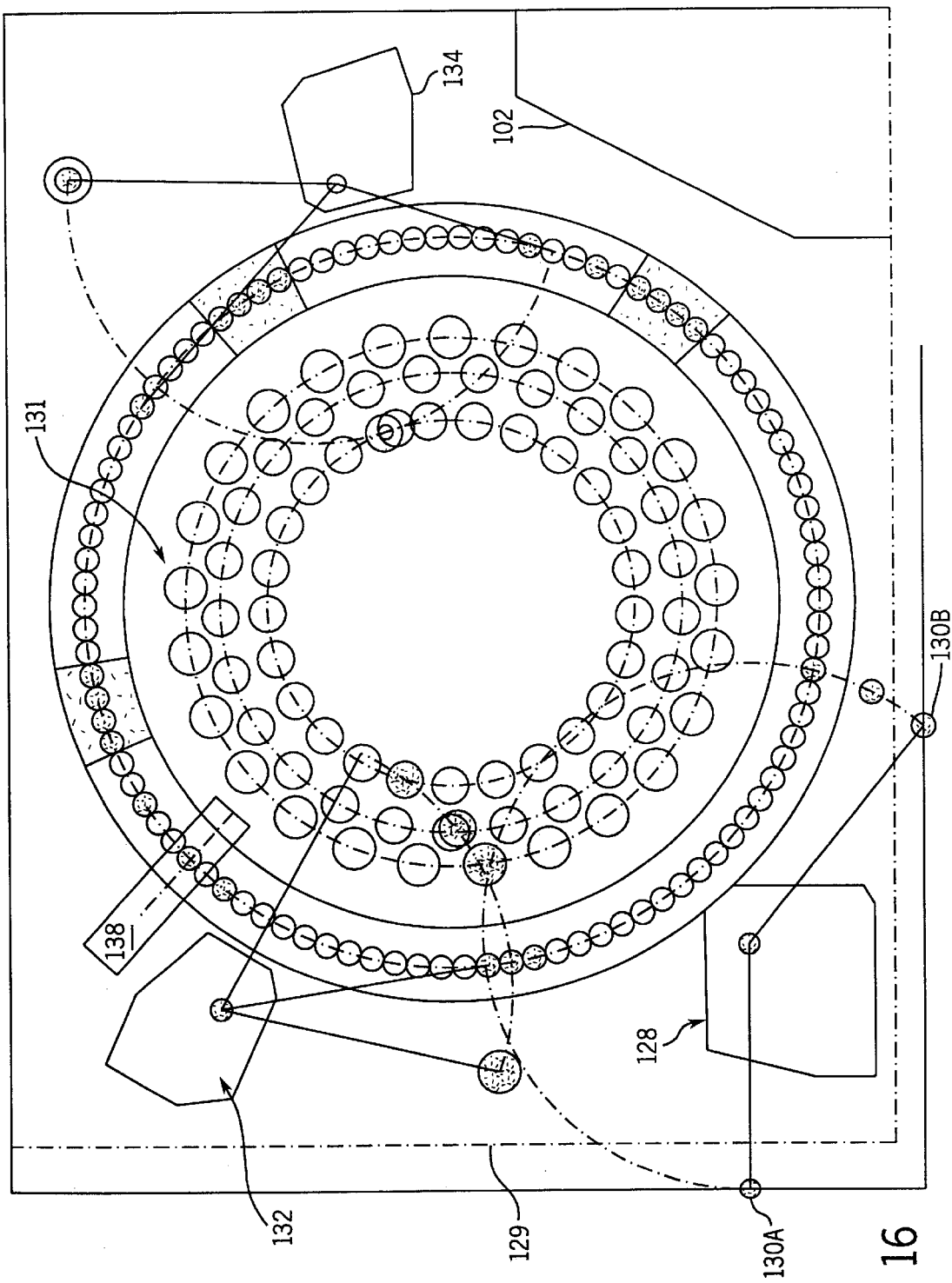
FIG. 16 is a generic view of the component of FIG. 1 cooperating with other portions of an analyzer.

Adding more specificity to the example, in a particular embodiment, the determination of an item of interest in a sample is an immunoassay. When the process path 10 is used to perform an immunoassay, the container 15 is moved into the process lane 28 at position 1. Also at position 1, a known quantity of sample (for example, 50 μl of blood) is deposited into the container 15 by a pipetting system 128. The pipetting system 128 comprises a pipettor, which may be substantially similar to the pipettors 116A, 116B and 116C, mounted on an arm for movement up and down and angularly, as shown in FIG. 16.

After indexing the container 15 to position 2, a known quantity of a first reagent, possibly along with an amount of fluid present in the pipetting system 132, is deposited into the container 15 by a second pipetting system 132. The first reagent may contain magnetically responsive microparticles coated with antibodies or other binding substances that specifically bind to the item of interest in the sample. The first reagent may be added with an assay specific diluent. In some cases, the first reagent and a conjugate, possibly along with an amount of fluid present in the pipetting system 132, may be added at position 2.

Figure 12:
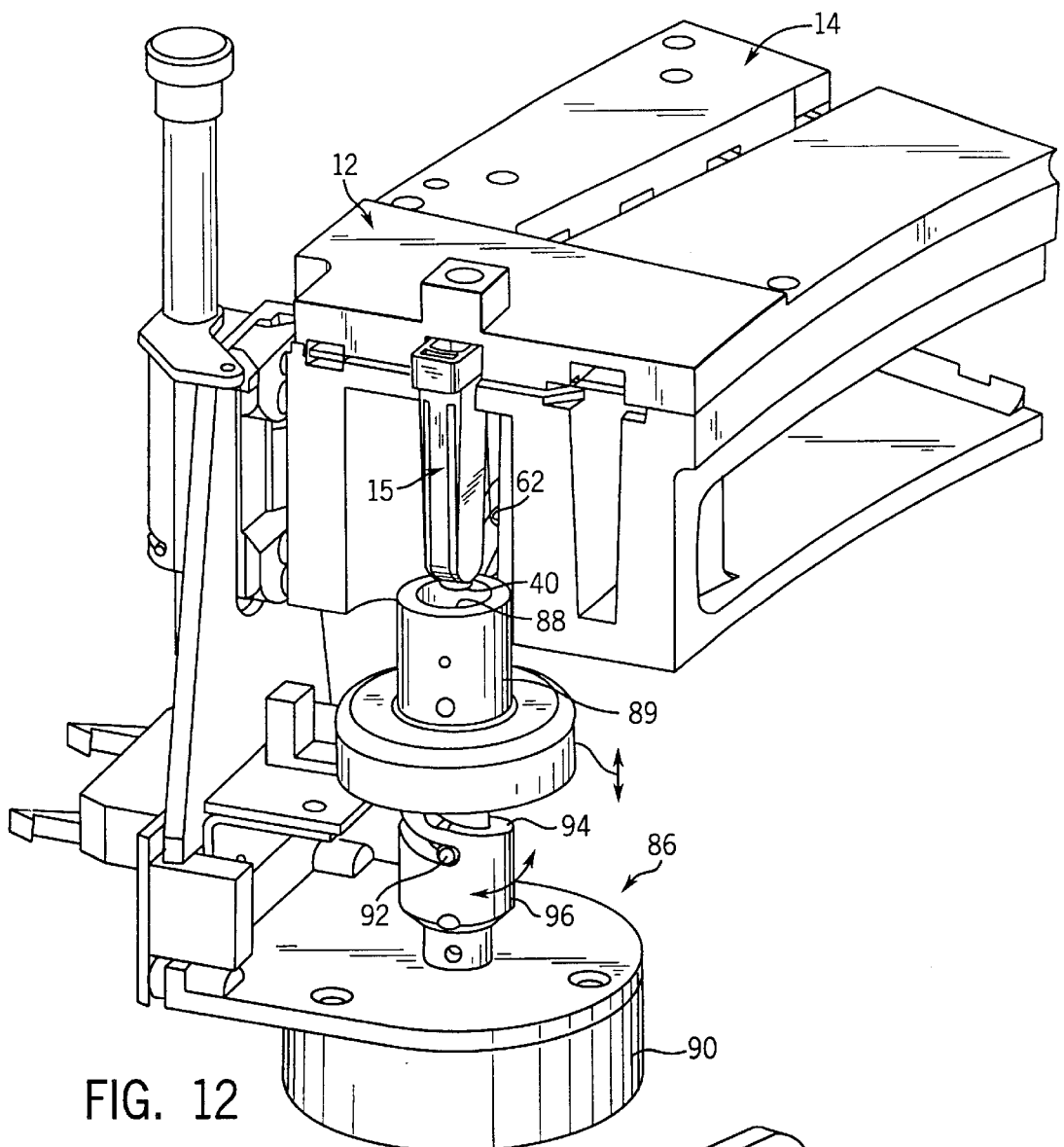
FIG. 12 is a perspective view of an element of the component of FIG. 1.

At position 3, a mechanical device 86 (illustrated in FIG. 12) is provided to mechanically move the container 15 and cause mixing of the contents of the container 15. The mechanical mixing device 86 includes a bore 88 formed within a body 89, which is eccentrically formed in the illustrated embodiment, that moves axially and rotatably under the influence of a prime mover 90 connected with the body 89. When the prime mover 90 is activated, the body 89 rotates clockwise, and a protrusion 92 connected with the prime mover 90 moves within a slot 94 in a second body 96. The second body 96 rotates freely about a drive shaft of the prime mover 90.

As the protrusion 92 moves within the slot 94, the body 89 and the bore 88 move toward the bottom 40 of the receptacle 15 as the body 89 rotates. When the body 89 and the bore 88 move toward the container 15, the bore 88 engages the bottom 40 of the container 15 and imparts an orbital (but not rotational) motion to the bottom 40 of the container 15. The portions of the container 15 adjacent the top surface 42 remain relatively stationary within the slot 18 in the disk 16.

The mechanical motion imparted to the container 15 mixes the sample with the first reagent. After the contents of the container 15 have been mixed for a predetermined time period, the prime mover 90 rotates its drive shaft counterclockwise, causing the protrusion 92 to move in an opposite direction within the slot 94, thereby moving the first body 89, the bore 88 and the second body 96 away from the bottom 40 of the container 15.

Illustrating further with a specific example, in one embodiment, the body 89 is made of PEEK with a black finish, the protrusion 92 is made of AISI 301 stainless steel with a #10 passivated finish, the second body 96 is made of Acetron GP with a white finish and the slot 94 has a #32 finish. The bore 88 in the body 89 is offset from an axis of the body 89 and has a radius of about 0.020 inches. An interface between the body 89 and the container 15 provides a minimum of about 0.05 inches of eccentric rotation of the container 15. The slot 94 provides a rise of about 0.315 inches over a rotation of the second body 96 of about 226.8 degrees. The prime mover 90 is a 3 phase, 8 pole, Y connected DC brushless motor P/N DR538-504 available from Shinano Kenshi of California. The prime mover 90 is supplied with a 36 Volt potential and operates substantially within the range of about 500 to about 5500 rpm's with a torque constant of about 620 g·cm/A.

The container 15 is freed from the bore 88 and processing of the container 15 contents continues. Subsequently, the container 15 contents is incubated for a predetermined time period.

At position 24, depending upon he particular item of interest in the sample to be determined, the first pipetting system 128 may withdraw a portion of the contents of the container 15 for deposition into another container 15 located at position 1. This may be appropriate when a particular determination requires pretreatment, such as pre-heating, heated incubation with a first reagent prior to second reagent introduction, and the like, prior to introduction of magnetically responsive microparticles comprising the first reagent.

Figure 15:
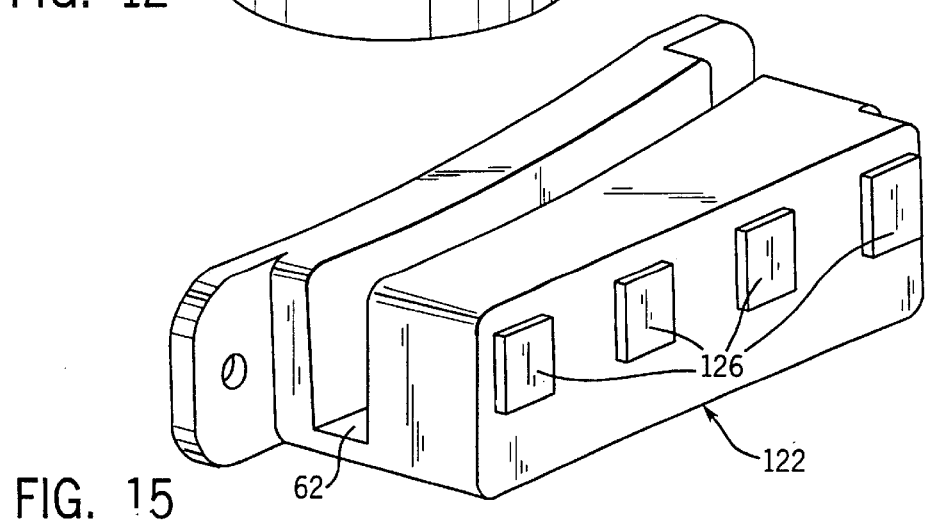
FIG. 15 is a perspective view of an element of the component of FIG. 1.
Figure 14:
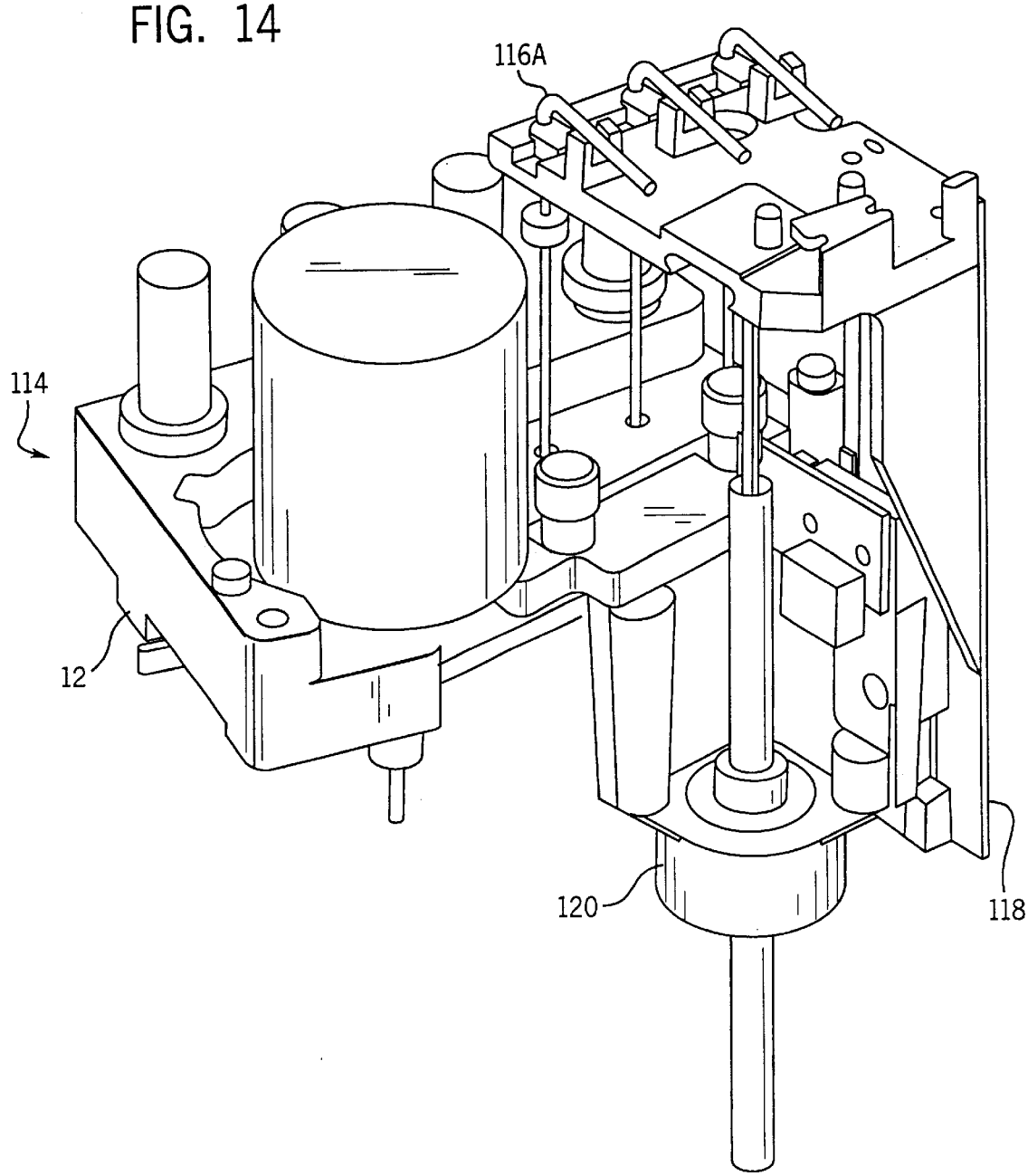
FIG. 14 is a perspective view of an element of the component of FIG. 1.

At position 37, the process path 10 selectively positions the container 15 for performing or avoiding a series of magnetic separation and wash steps. Structures for performing the wash and separation comprise a wash station 114, shown in FIGS. 14 and 15.

Each wash station 114 includes a plurality, 3 in the illustrated embodiment, of movable pipettors 116A, 116B and 116C and at least one stationary nozzle (not shown) for moving fluids at least one of into and out of the container 15. In some embodiments, the movable pipettors 116A, 116B and 116C may be used to move fluids out of the container 15 while the at least one stationary nozzle moves fluid into the container 15. Sensors, such as thermistors and the like, may be operatively associated with the pipettors 116A, 116B and 116C to verify fluid movements.

The pipettors 116A, 116B and 116C move liquids both into and out of the container 15 whereas the nozzle only moves liquid into the container 15. The movable pipettors 116A, 116B and 116C are connected to a common base plate 118 which moves with respect to the cover 12 under the influence of a prime mover 120, such as a stepper motor and tile like. Responsive to the prime mover 120, the pipettors 116A, 116B and 116C move into and out of the container 15. Suitable fluid delivery conduits, not shown, are connected with the pipettors 116A, 116B and 116C and the nozzle. The pipettors 116A, 116B and 116C are spring-loaded to facilitate their replacement and to cushion any contact between the pipettors 116A, 116B and 116C and another surface, such as the bottom 40 of the container 15 and the like.

The pipettors 116A, 116B and 116C are movable to remove fluid from the container 15. Because the item of interest is connected with the magnetic particles, a magnet assembly 122 is also included a the wash station 114. The magnet assembly 122 is disposed in a receptacle 124 in the base 14. The magnet assembly 122 includes a portion of the performance lane 62 and holds a plurality of permanent magnets 126. In an exemplary embodiment, the assembly 122 is made from 6061 T6 aluminum with a finish of MIL-A-63576 Type I and the magnets 126 are neodymium Iron Boron (NdFeB) magnets with a residual flux density (Br) substantially within the range of about 12.1 to about 13.2 KG, a coercive force (Hc) substantially within the range of about 11.0 to about 12.0 KOe, an intrinsic coercive force (Hci) substantially within the range of about 17.0 to about 19.0 KOe and a total energy product (BHmax) substantially within the range of about 34.0 to about 41.0 MGOe. The field intensity of the magnets 126 at a distance of about 0.030 inches from the container 15 is about 4470 Gauss and at a distance of about 0.176 inches from the container 15 is about 1570 Gauss.

At the wash station 126, the magnets 126 hold the magnetic particles, and thereby the item of interest, against a side wall 36A or 36B of the container 15. This allows removal of contents of the container 15 other than the magnetic particles and the item of interest bound to the magnetic particles. In some constructions, the pipettors 116A, 116B and 116C may be positioned such that the pipettors 116A, 116B and 116C move substantially along a central axis of elongation of the container 15, may be biased away from a side wall 36A or 36B against with the magnetic particles are held, or otherwise constructed to reduce the chances of the pipettors 116A, 116B and 116C removing magnetic particles and the item of interest bound to the magnetic particles from the container 15.

In an exemplary embodiment, the pipettors 116A, 116B and 116C are made from Inconel. The pipettors 116A, 116B and 116C are disposed such that lnongitudinal center lines of the pipettors 116A, 116B and 116C are offset a distance measuring about 0.029 inches from a center line of the containers 15 into which the pipettors 116A, 116B and 116C are inserted. This offset distances the pipettors 116A, 116B and 116C from magnetic particles within the containers 15. When the pLpettors 116A, 116B and 116C dispense fluid into the containers 15, the pipettors 116A, 116B and 116C are located a distance measuring about 0.342 inches from a side wall of the containers 15 adjacent the magnets 126. The pipettors 116A, 116B and 116C are mounted with springs so as to absorb up to 0.1 inches of overdrive. The pipettors 116A, 116B and 116C are fluidly connected with a valve which allows for bubble flushing without use of a container 15. The stationary nozzle is made of 0.031 inch inner diameter PEEK tubing. The base plate 118 is a two piece, thermally bonded assembly of acrylic with a clear Iridite finish on top and an opaque finish on the bottom to allow fluid visibility and light protection for a chemiluminescence reader.

If, for a particular determination, magnetic separation and washing is required at position 37, the container 15 is moved to the performance lane 62. Containers 15 in the performance lane 62 undergo, at each processing position between 41 and 44, magnetic separation (effected by permanent magnets 126 at fixed locations adjacent to the performance lane 62), fluid asorration, and fluid dispensing, performed by fluid handling devices introduced through an opening 93 (FIG. 1) in the cover 12. In one embodiment, one of these wash stations (position 41) includes only a magnetic separation and fluid dispensing step that introduces a wash buffer to the container 15. In some cases, wash buffer or other fluid is added such that the amount of fuild present within the container 15 facilitates separation (magnetic) of the particles from the fluid in the container 15. At positions 42 and 43, separation, fluid aspiration, and fluid dispensing occur. In position 44, the magnetic particles are separated from the fluid in the container 15 by magnets 126 and fluid is aspirated. In this example, these steps would remove substantially all substances within the container 15 that have not bound to binding conjugate elements on the magnetic particles deposited as the first reagent. Containers 15 within the avoidance lane 64 are undisturbed and continue incubation. The performance and avoidance lanes 62 and 64 merge between positions 45 and 46.

A second reagent may be deposited into the container 15 at location 48 (FIG. 4) by a third pipetting system 134, again followed by a mechanical device 86 at position 49 to mix the container 15 contents. The second reagent may include an indicator substance, such as a chemiluminescent substance, linked to binding elements that also bind to the item of interest (remaining occurrences of which are bound to the magnetic particles of the first reagent). The contents of the container 15 are incubated at positions 50–59.

The second bypass region 58B begins at position 60, where the container 15 may selectively automatically undergo a set of magnetic separations, fluid aspirations, and fluid dispensing steps.

The third pipetting system 134 may deposit a third reagent into the container 15 at position 71, with subsequent mixing at position 72 and incubation between positions 73 and 86.

The third bypass region 58C begins at position 86, where the container 15 may selectively automatically undergo a set of magnetic separations, fluid aspirations and fluid dispensing steps.

In one embodiment, where it is assumed that substantially a majority of the containers 15 will undergo magnetic separation, fluid aspiration, and fluid dispensing at positions 87–90, no bypass region 58C may be provided at these locations. For example, these step would cause the removal of substantially all indicator (chemiluminescent) substances that are not bound to the magnetic particles (via the analyte of interest), yielding a container 15 holding indicator substance in an amount indicative of the amount of the item of interest in the initial sample deposition. However, in some determinations, it is desirable to avoid those process steps.

A pretrigger reagent may be deposited by a fluid dispensing device at position 94.

A fluid dispensing device will deposit a triggering agent at position 98, which causes the indicator reaction to occur. For example, a chemiluminescent substance releasing reagent may be deposited at position 94, which causes the release of the indicator (chemiluminescent) substance from the magnetic particles.

The contents of the container 15 are incubated between positions 95 and 97, inclusive.

Position 98 may also include a magnet, which separates or removes substantially all of the magnetic particles from the fluid within the container 15. The magnet holds substantially all of the magnetic particles against a side wall 36A or 36B of the container 15 prior to reading of light from the chemiluminescent substance. Preferably, all of the magnetic particles are removed from a path of chemiluminescent photons from the chemiluminescent substance, which remains in solution in the fluid in the container 15, to a light detection apparatus 138. This read step is substantially similar to that described in EP 0 371 265 B1 issued Jan. 1, 1994. The introduction of the triggering reagent would initiate a chemiluminescent reaction which would be detected and quantified by an optical detection system (not shown) such as a photomultiplier tube or photon counting system.

In an exemplary embodiment, the apparatus 138 may comprise a reader assembly such as No. 73202 available from Thorn EMI of Rockaway, N.J., a photomultiplier tube such as No. 78252-101 available from Hammamatsu of Middlesex, N.J. and a substantially light-tight shutter operable by a plunger such as No. 78200-101 available from Ironwood Industries of Libertyvile, Ill. and a motor such as No. 78851-101 available from Haydon Switch & Instrument of Waterbury, Conn.

The embodiment described in the following examples demonstrates its utility in processing multiple assays of different formats and timing requirements within a common process path 10. In these examples, the embodiment described enables the execution of at least the following four assay formats, the first three of which may be executed simultaneously with no degradation in processing capacity.

| Format A | |
|---|---|
| Step | Position |
| Sample introduction | 1 |
| First reagent introduction and mixing | 2–3 |
| First incubation (18 minutes) | 4–63 |
| Separation and wash | 64–67 |
| Second reagent Introduction and mixing | 71–72 |
| Second incubation (4 minutes) | 73–86 |
| Separation and wash | 87–90 |
| Pretrigger introduction and mixing | 94 |
| Third incubation (1 minute) | 95–97 |
| Trigger and read | 98 |

As an example, Format A may be used to determine at least the following items of interest: antibodies to HCV, antibodies to HIV 1/HIV 2, antibodies to hepatitis B core antigen (HBcAb), carcinoembryonic antigen (CEA), cancer antigen 19-9 (CA19-9), Hepatitis B Surface Antigen (HBsAg), antibodies to Hepatitis B Surface antigen (HBsAb), alpha-fetoprotein (AFP), Total prostate specific antigen (Total PSA), Free PSA, Thyroid stimulating Hormone (TSH), luteinizing hormone (LH), follicle stimulating hormone (FSH), beta human chorionic gonadotropin (B-hCG), Free Thyroxine (Free T4), Free triiodothyronine (Free T3), Total T4, Total T3, Prolactin an Ferritin. It is to be noted that almost any item of interest discussed herein may be determined by properly using his format. For instance, this format may also be used to determine beta human chorionic gonadotropin (B-hCG), prolactin and ferritin.

| Format B | |
|---|---|
| Step | Position |
| Sample Introduction | 1 |
| First reagent introduction and mixing | 2–3 |
| First incubation (11 minutes) | 4–40 |
| Separation and wash | 41–44 |
| Second reagent introduction and mixing | 48–49 |
| Second incubation (11 minutes) | 50–86 |
| Separation and wash | 87–90 |
| Pretrigger introduction and mixing | 94 |
| Third incubation (1 minute) | 95–97 |
| Trigger and read | 98 |

As an example, Format B may be used to determine an item of interest in a sample where a relatively increased degree of sensitivity, as compared with some other formats, is desired. It is to be noted that almost any item of interest discussed herein may be determined by properly using this format.

| Format C | |
|---|---|
| Step | Position |
| Sample introduction | 1 |
| First reagent introduction and mixing | 2–3 |
| First incubation (11 minutes) | 4–40 |
| Separation and wash | 41–44 |
| Second reagent introduction and mixing | 48–49 |
| Second incubation (4 minutes) | 50–63 |
| Separation and wash | 64–67 |
| Third reagent introduction and mixing | 71–72 |
| Third incubation (4 minutes) | 73–86 |
| Separation and wash | 87–90 |
| Pretrigger introduction and mixing | 94 |
| Fourth incubation (1 minute) | 95–97 |
| Trigger and read | 98 |

As an example, Format C may be used when the item of interest relates to hepatitis, such as determinations for anti-M, HBcAb-M and HAVAb-M.

| Format D | |
|---|---|
| Step | Position |
| Sample introduction | 1 |
| First reagent introduction and mixing | 2–3 |
| First incubation (7 minutes) | 4–23 |
| Transfer to second container 15 in position 1 | 24 |
| Second reagent introduction and mixing | 2–3 |
| Second incubation (11 minutes) | 4–40 |
| Separation and wash | 41–44 |
| Third reagent introduction and mixing | 48–49 |
| Third incubation (4 minutes) | 50–63 |
| Separation and wash | 64–67 |
| Fourth reagent introduction and mixing | 71–72 |

Format D -continued

| Step | Position |
|---|---|
| Fourth incubation (4 minutes) | 73–86 |
| Separation and wash | 87–90 |
| Pretrigger introduction and mixing | 94 |
| Fifth incubation | 95–97 |
| Trigger and read | 98 |

Format E

| Step | Position |
|---|---|
| Sample introduction | 1 |
| First reagent introduction and mixing | 2–3 |
| First incubation (7 minutes) | 4–23 |
| Transfer portion of container 15 contents to second container 15, remainder of container 15 continues on process lane 28 | 24 |
| First container 15 contents continues first incubation (11 minutes) | 24–63 |
| Second reagent introduction and mixing with second container 15 contents | 2–3 |
| First container 15 passes through bypass region 58B | 64–67 |
| Second container 15 first incubation (18 minutes) | 4–63 |
| Introduction of fourth reagent into first container 15 and mixing (optional, enhances total Hb chemiluminescent signal) | 71–72 |
| Second container separation and wash | 64–67 |
| Fourth incubation (4 minutes — optional) of first container 15 | 73–86 |
| Third reagent introduction into second container 15 and mixing | 71–72 |
| First container 15 passes through bypass region 58C | 87–90 |
| Third incubation (4 minutes) of second container 15 | 73–86 |
| Pretrigger introduction into first container 15 and mixing | 94 |
| Separation and wash of second container 15 | 87–90 |
| Trigger and read value 1 (Total Hb) from first container 15 | 98 |
| Pretrigger introduction into second container 15 and mixing | 94 |
| Trigger and read value 2 (GlyHb) | 98 |

$$\text{Reported result} = \frac{\text{value 2}}{\text{value 1}} \times 100$$

For example, in Format E, it is possible to modify the format by disregarding the first container 15 after the portion of the container 15 contents has been transferred (Position 24) to the second container 15. In that case, Format may be used to determine, for example, folate and vitamin B12.

Format F

| Step | Position |
|---|---|
| Sample introduction | 1 |
| First reagent introduction and mixing | 2–3 |
| First incubation (7 minutes) | 4–23 |
| Transfer portion of container 15 contents to second container 15, remainder of container 15 continues on process lane 28 | 24 |
| First container 15 contents continues first incubation (11 minutes) | 24–63 |
| Second reagent introduction and mixing with second container 15 contents | 2–3 |
| First container 15 passes through bypass region 58B | 64–67 |
| Second container 15 first incubation (11 minutes) | 4–40 |
| Introduction of fourth reagent into first container 15 and mixing (optional, enhances total Hb chemiluminescent signal) | 71–72 |
| Second container separation and wash | 41–44 |
| Fourth incubation (4 minutes — optional) of first container 15 | 73–86 |
| Third reagent introduction into second container 15 and mixing | 48–49 |
| First container 15 passes through bypass region 58C | 87–90 |
| Third incubation (11 minutes) of second container 15 | 50–86 |
| Pretrigger introduction into first container 15 and mixing | 94 |
| Separation and wash of second container 15 | 87–90 |
| Trigger and read value 1 (Total Hb) from first container 15 | 98 |
| Pretrigger introduction into second container 15 and mixing | 94 |
| Trigger and read value 2 (GlyHb) | 98 |

$$\text{Reported result} = \frac{\text{value 2}}{\text{value 1}} \times 100$$

This format may be used, for example, to determine at least one of total and and glycated hemoglobin. Also, this format may be modified by disregarding the first container 15 as in Format E.

| Format G | |
|---|---|
| Step | Position |
| Sample introduction | 1 |
| First reagent introduction and mixing | 2–3 |
| First incubation (7 minutes) | 4–23 |
| Transfer portion of container 15 contents to second container 15, remainder of container 15 continues on process lane 28 | 24 |
| First container 15 contents continues first incubation (11 minutes) | 24–63 |
| Second reagent introduction and mixing with second container 15 contents | 2–3 |
| First container 15 separation and wash | 64–67 |
| Second container 15 first incubation (18 minutes) | 4–63 |
| Introduction of fourth reagent into first container 15 and mixing (optional, enhances total Hb chemiluminescent signal) | 71–72 |
| Second container separation and wash | 64–67 |
| Fourth incubation (4 minutes — optional) of first container 15 | 73–86 |
| Third reagent introduction into second container 15 and mixing | 71–72 |
| First container 15 separation and wash | 87–90 |
| Third incubation (4 minutes) of second container 15 | 73–86 |
| Pretrigger introduction into first container 15 and mixing | 94 |
| Separation and wash of second container 15 | 87–90 |
| Trigger and read value 1 (Total Hb) from first container 15 | 98 |
| Pretrigger introduction into second container 15 and mixing | 94 |
| Trigger and read value 2 (GlyHb) | 98 |

$$\text{Reported result} = \frac{\text{value 2}}{\text{value 1}} \times 100$$

As an example, this format may also be modified as may be done with Format F. With that modification, this Format may be used to determine progesterone, testosterone and estradiol.

| Format H | |
|---|---|
| Step | Position |
| Sample introduction | 1 |
| First reagent introduction and mixing | 2–3 |
| First incubation | 4–86 |
| Separation and wash | 87–90 |
| Pretrigger introduction and mixing | 94 |
| Second incubation | 95–97 |
| Trigger and read | 98 |

As an example, this format may be used to determine, among other things, beta human chorionic gonadotropin (B-hCG), prolactin, progesterone, testosterone, estradiol and ferritin. It is to be noted that almost any item of interest discussed herein may be determined by properly using this format.

| Format I | |
|---|---|
| Step | Position |
| Sample introduction into first container 15, possibly with diluent fluid | 1 |
| First reagent introduction into first container 15, portion of first container 15 contents moved into pipettor, remainder of container continues on process lane 28, bypassing all wash stations, to Position 71 | 2 |
| First reagent introduction into second container 15 and mixing | 2–3 |
| First incubation of second container 15 | 4–23 |
| Second container 15 first incubation (18 minutes) | 24–63 |
| Introduction of second reagent into first container 15 and mixing (optional, enhances total Hb chemiluminescent signal) | 71–72 |
| Second container separation and wash | 64–67 |
| Fourth incubation (4 minutes — optional) of first container 15 | 73–86 |
| Third reagent introduction into second container 15 and mixing | 71–72 |
| First container 15 passes through bypass region 58C | 87–90 |
| Third incubation (4 minutes) of second container 15 | 73–86 |
| Pretrigger introduction into first container 15 and mixing | 94 |
| Separation and wash of second container 15 | 87–90 |
| Trigger and read value 1 (Total Hb) from first container 15 | 98 |
| Pretrigger introduction into second container 15 and mixing | 94 |

-continued

Format I

| Step | Position |
|---|---|
| Trigger and read value 2 (GlyHb) | 98 |

$$\text{Reported result} = \frac{\text{value 2}}{\text{value 1}} \times 100$$

As an example, in Format I, it is possible to modify the format by disregarding the first container 15 after the portion of the container 15 contents has been transferred (Position 24) to the second container 15. In that case, Format I may be used to determine, for example, folate and vitamin B12.

Format J

| Step | Position |
|---|---|
| Sample introduction into container 15, possibly with diluent fluid | 1 |
| First reagent introduction and mixing | 2–3 |
| First incubation (27 minutes) | 4–93 |
| Pretrigger introduction and mixing | 94 |
| Second incubation (1 minute) | 95–97 |
| Trigger and read | 98 |

As an example, Format J may be used to determine, among other things, total hemoglobin.

The embodiments described herein also allow for sample pretreatment which may be performed in at least two ways, indicated as Formats K and L. During performance of sample pretreatment, fluid present in the containers 15 indicated may be processed, after they are no longer significant in the pretreatment steps, in any appropriate manner, such as any of the Formats discussed above. Also, as will become clear later on, both Formats K and L are substantially similarly applicable to the other embodiments of the process path 10 discussed below.

Format K

| Step | Position |
|---|---|
| Sample introduction into first container 15, possibly with diluent fluid | 1 |
| First reagent introduction and mixing | 2–3 |
| First incubation (7 minutes) | 4–23 |
| Transfer portion of contents of first container 15 to second container 15 in Position 1 | 24 |
| Second reagent introduction to second container 15 and mixing | 2–3 |

-continued

Format K

| Step | Position |
|---|---|
| (optional) Transfer portion of contents of second container 15 to third container 15 in Position 1 | 24 |
| Third reagent introduction to third container and mixing (optional) | 2–3 |

As an example, the third container 15 may be processed according to at least one of Formats A to determine, among other things, folace), B, C, H and J.

Format L

| Step | Position |
|---|---|
| Sample introduction into first container 15, possibly with diluent fluid | 1 |
| First reagent introduction and mixing | 2–3 |
| First incubation (7 minutes) | 4–23 |
| Transfer portion of contents of first container 15 to second container 15 in Position 1 | 24 |
| Second reagent introduction to second container 15 and mixing (optional) | 2–3 |

As an example, the second container 15 may be processed according to at least one of Formats A (to determine, among other things, folate, vitamin B12, confirm HBsAg), B, C, H and J.

In each of the formats discussed above, it is possible to move contents of a first container 15 at Position 2 or 24 into a second container 15 at Position 1. Thereafter, the first container 15 may or may not be ignored.

It is to be remembered, as pointed out earlier, that the steps of one format may be mixed with steps of another format to arrive at yet further formats. Also, it is to be remembered that the construction of the process path 10, and its elements and supporting components, allow for selective automated performance (i.e. a particular step may or may not be performed, as desired) of the above-described steps.

These examples demonstrate usefulness of the described embodiments in controlled processing of determinations of items of interest in a sample within a common process path 10.

As discussed earlier, multiple process paths 10 may be connected to meet specific needs. If the process path 10 were to perform approximately 200 determinations per hour, and if an analyzer (FIG. 29) that performed 400 determinations per hour were needed, then two process paths 10 could be connected. One way of doing is described with reference to FIGS. 17, 29 and 30.

Figure 17:
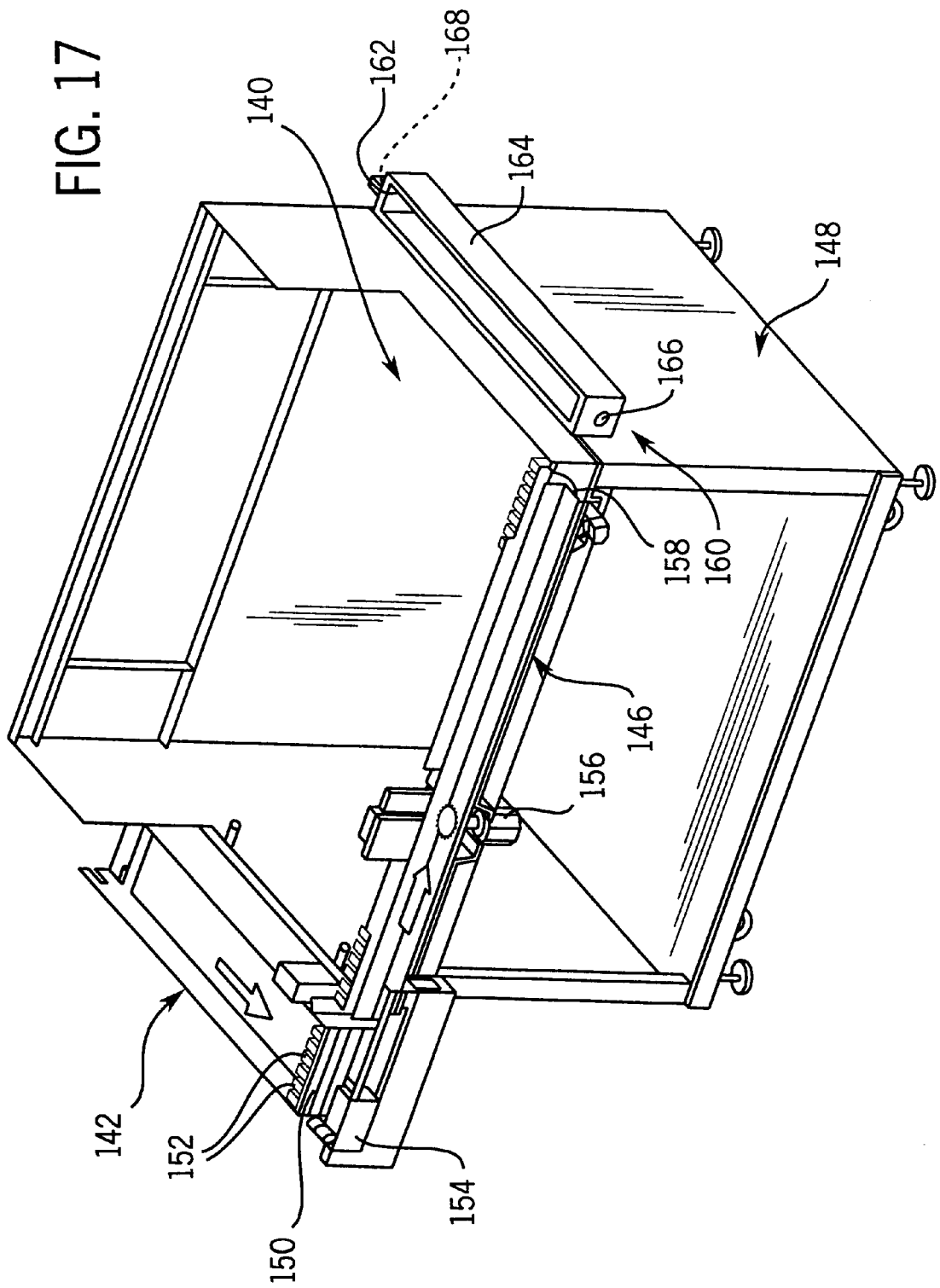
FIG. 17 is a perspective view of a frame for the structures shown in FIG. 16.
Figure 30:
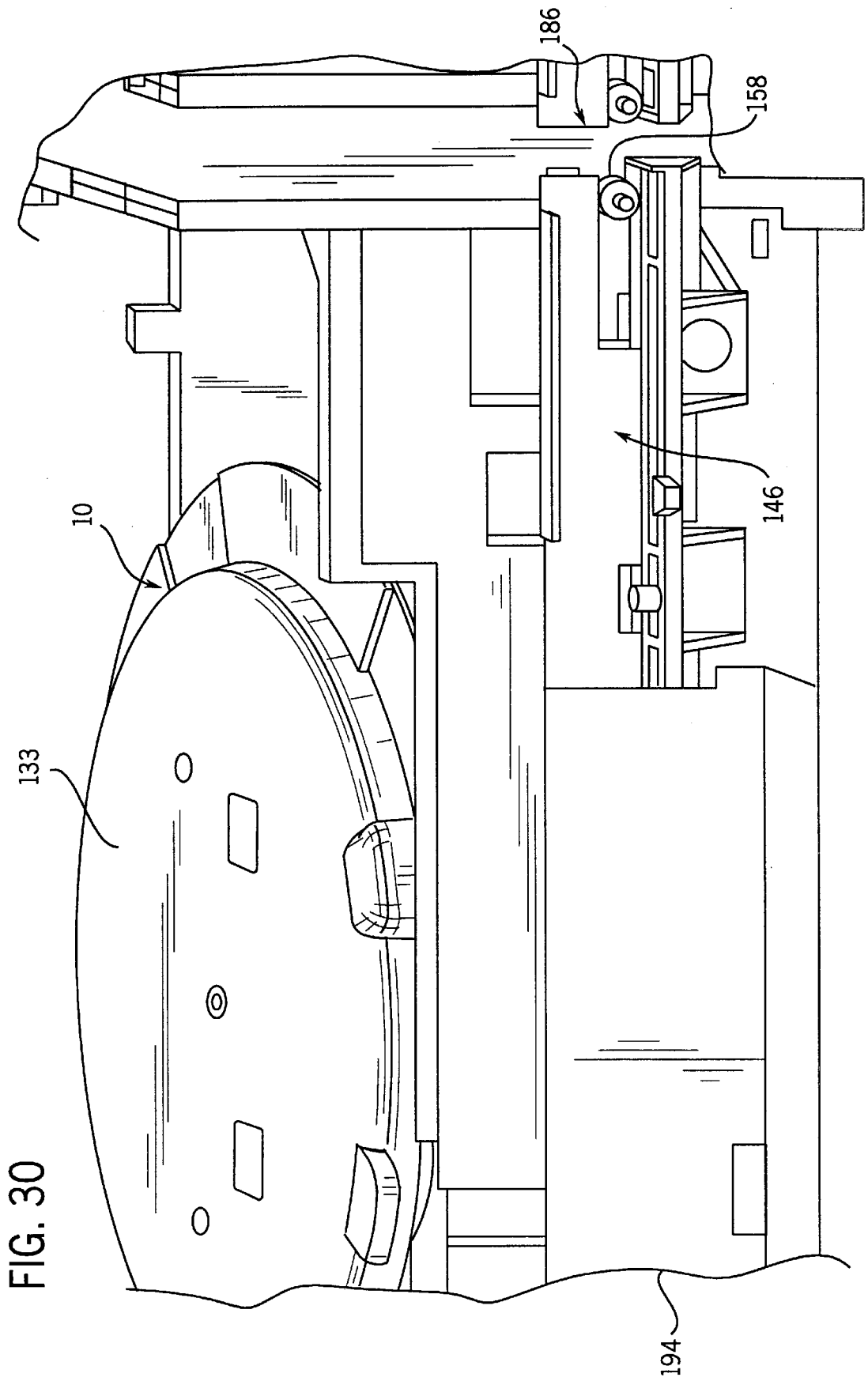
FIG. 30 is an enlarged view of a portion of FIG. 29.

As FIG. 17 illustrates, the process path 10 would be located an space 140. No supply samples to the process path 10, a load track 142 and a conveyor 146 are provided connected to a frame 148 defining the space 140. In some embodiments, at least one of the load track 142, the conveyor 146 and an unload track 192 may be provided with a cover 194 (FIG. 30). A carrier 150 supporting multiple sample tubes 152, which may be any suitable tubes, rides along both the load track 142 and the conveyor 146. Both the load track 142 and he conveyor 146 move the carrier 150 as indicated by the arrows. A transfer mechanism 154, such as a solenoid (e.g. linear actuation, driven arm and the like, shifts carrier 150 from the load track 142 to the conveyor 146.

The carrier 150 moves along the conveyor 146 until the carrier 150 is stopped by a retention member 156, which is, in the illustrated embodiment, a stepper motor driving a star wheel which mates with the carrier 150. The pipetting system 128 accesses sample at the position 130B and supplies that sample to a contiainer 15 on the process path 10. Of course, suitable identification structures, such as bar codes cn the sample tubes 152 and a bar code reader, can be provided. When the pipetting system 128, or any of the pipetting systems 128, 132 or 134 access a fluid, pipetting system pressure can be monitored as described in commonly owned U.S. patent application, Ser. No. 08/572,835 filed on Dec. 14, 1995. The disclosure of that application is Incorporated herein in its entirety. Appropriate liquid level sense devices, such as radio frequency based devices and the like, may also be located in suitable positions.

In an exemplary embodiment, the load track 142 may be No. 77325-101 and the conveyor 146 may be No. 77425-101 both available from Dorner Manufacturing of Hartland, Wis. The unload track 192 may be No. 77525-101 available from SPM/Portland of Hillsboro, Oreg. The retention member 156 may be No. 77476-101 available from Pacific Scientific of Elgin, Ill. The transfer mechanism 154 may comprise a solenoid such as No. 77952 available from Lucas/Ledex of Vandalia, Ohio, a belt such as No. 6R25-M225090 and a pulley such as No. A 6725-020DF0908 both available from Stock Drive Parts of New Hyde Park, N.Y., and a stepper motor such as No. P21NSXS-LSS-NS-07 available from Pacific Scientific of Elgin, Ill.

Figure 31A:
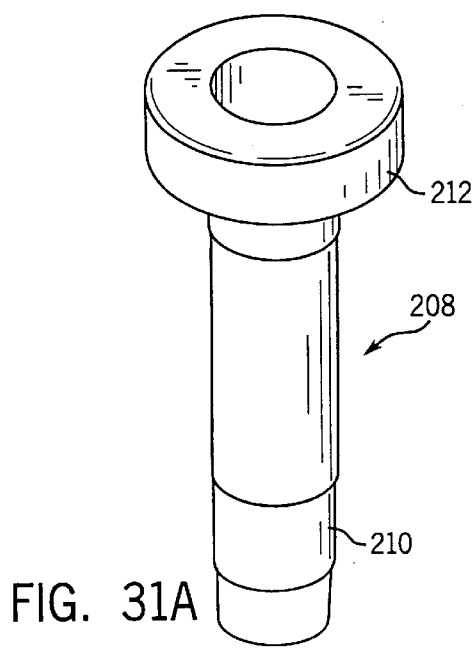
FIGS. 31A, 31B and 31C show another container for use with the process path of FIG. 1.
Figure 31B:
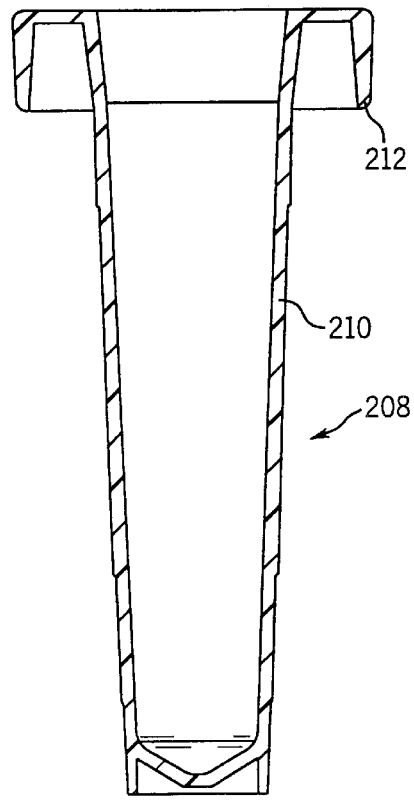
Figure 31C:
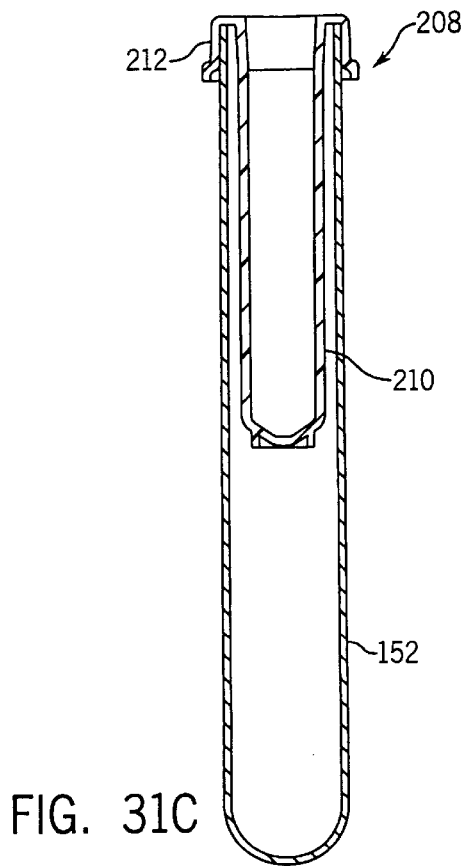

In some cases, a level of sample in a sample tube 152 may be insufficient for access by the pipetting system 128. In these cases, the sample within the sample tube 152 may be moved by an operator into another container 208 shown in FIGS. 31A, 31B and 31C. The container 208 comprises a barrel 210 and a flange 212. The barrel 210 is dimensioned to fit within the sample tube 152 as shown in FIG. 31C. The flange 212 is offset from an outer diameter surface of the barrel 210 by a distance sufficient to accommodate any suitable sample tubes 152. In this way, sample can be moved from the sample tube 152 into the container 203 and the container 208 can be placed within the sample tube 152. The sample tube 152 bearing the container 203 may then be placed into the carrier 150. Because the sample is now in the container 208, the level of the sample is elevated with respect to the level of the sample in the sample tube 152, thereby facilitating sample access by the pipetting system 128.

In an exemplary embodiment, the container 208 may be made from DOW 666 polystyrene and is dimensioned to fit within sample tubes having outer diameters substantially within the range of about 0.4 inches through about 0.7 inches. The barrel 210 has an outer diameter measuring about 0.4 inches and a length of about 1.964 inches. The flange 212 has an outer diameter measuring about 0.776 inches, depends from an open end of the container 208 by a distance of about 0.216 inches and is offset from the outer diameter surface of the barrel 210 by a distance of about 0.258 inches.

Figure 26:
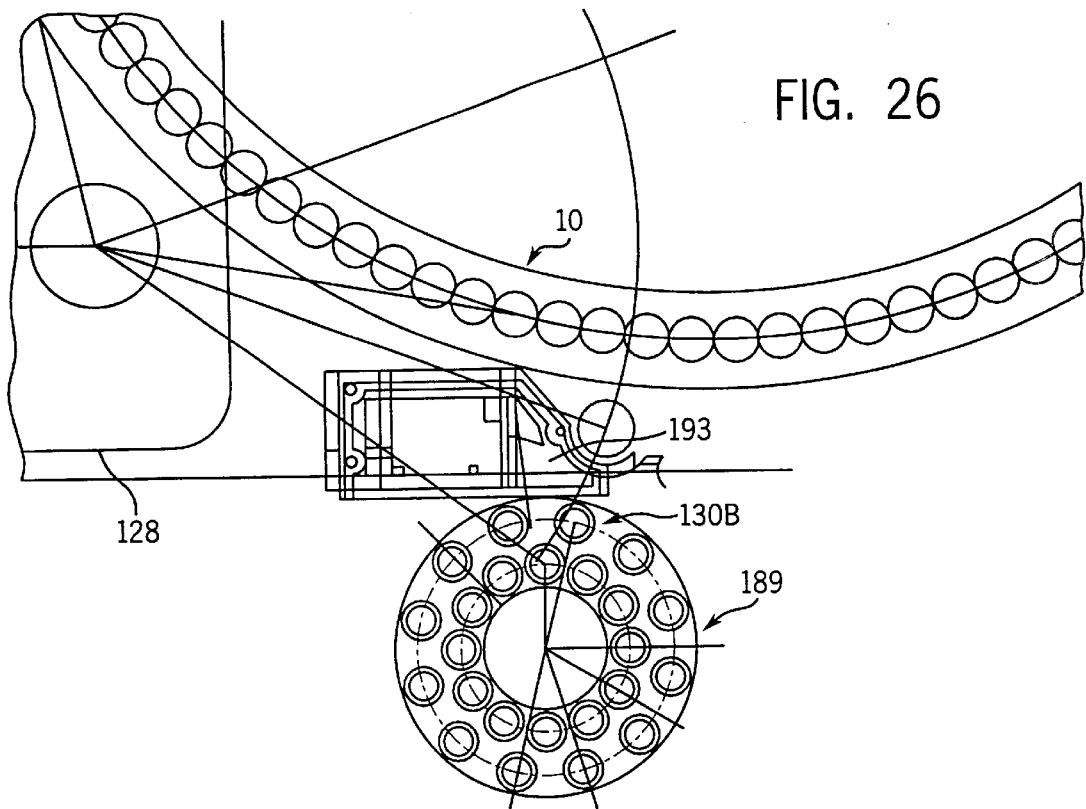
FIG. 26 is an enlarged section of another application of the process path of FIG. 1.
Figure 27:
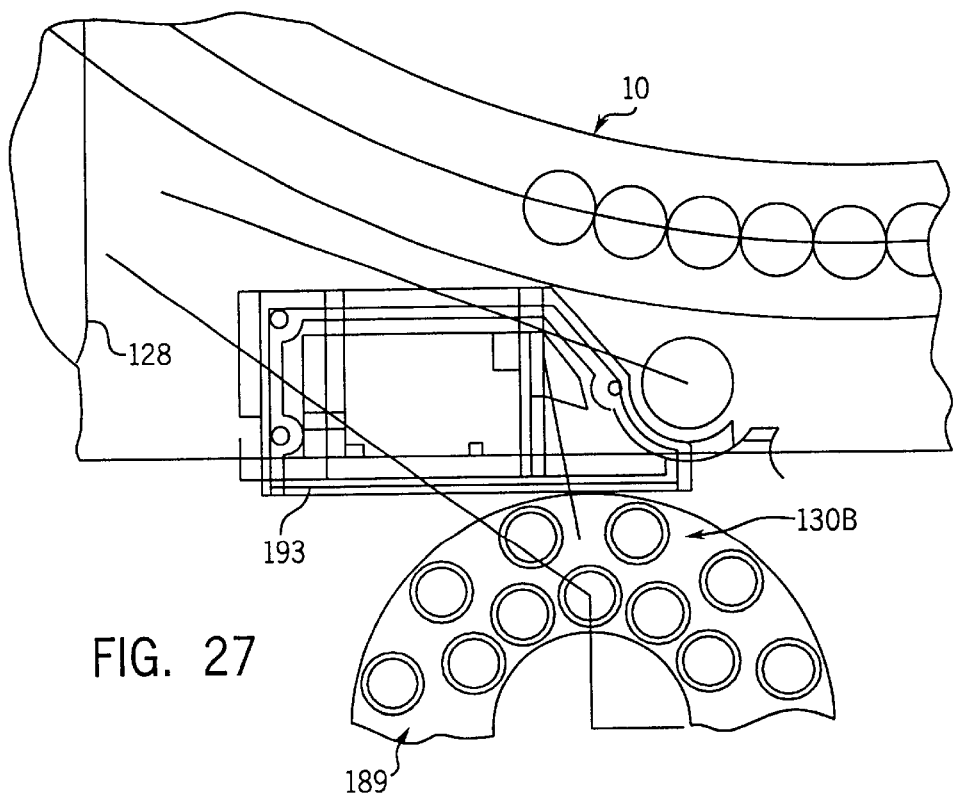
FIG. 27 is an enlargement of a portion of FIG. 27.
Figure 28:
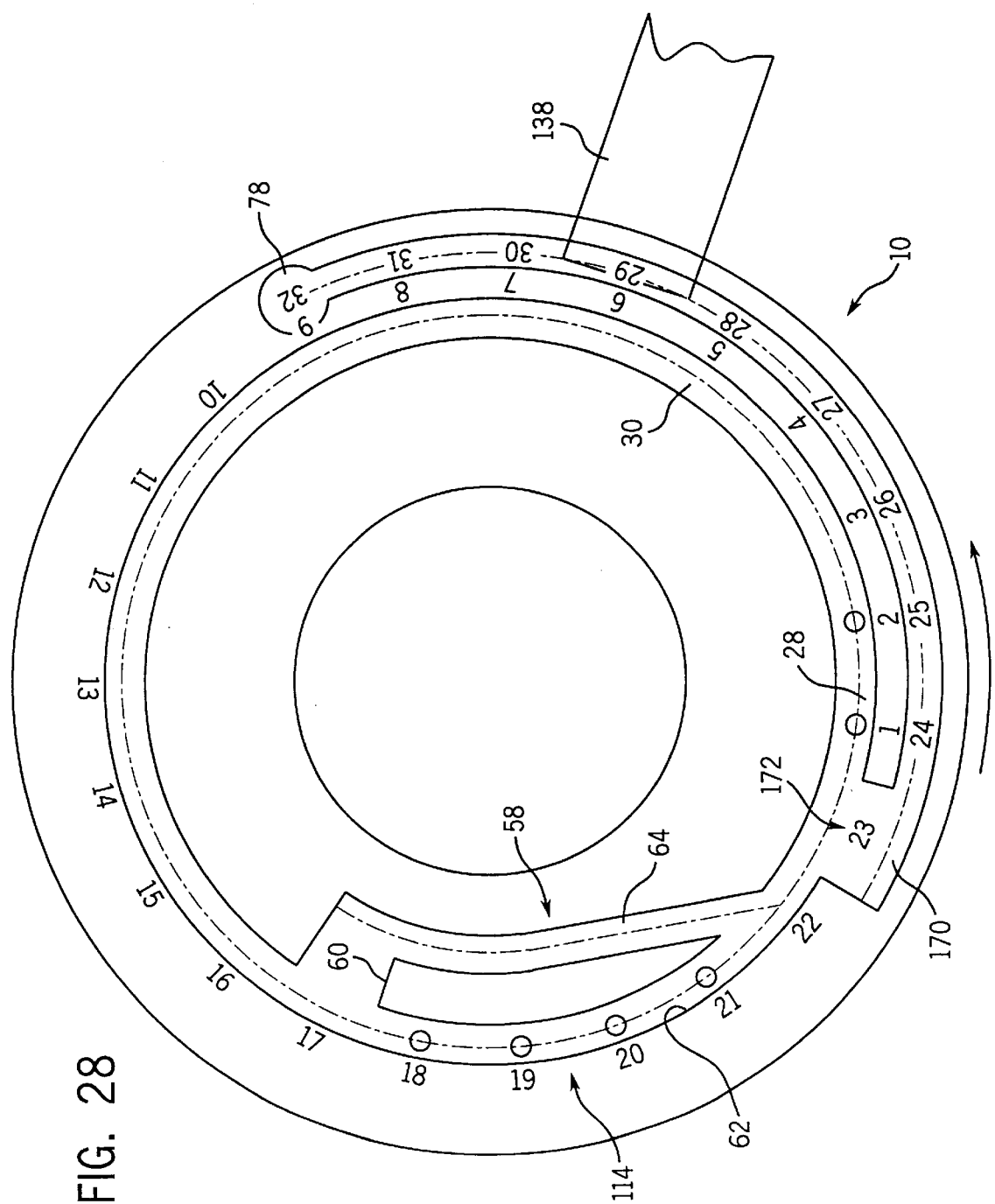
FIG. 28 is a generic view of another related analyzer having a component substantially similar to the component of FIG. 1.

In some embodiments, the load track 142 is removed and replaced by a sample supply conveyor having a similar retention member 156. If this were done, then the pipetting system 128 would access sample at position 130A. If this case, then, in additional embodiments, a carousel 139 may be operatively connected with the frame 148 by a connection member 193 as shown in FIGS. 26 and 27. The connection member 193 locates the carousel 189 with respect to the process path 10 such that the pipetting system 128 can also access containers on the carousel 189 at position 130B. The carousel 189 may be used, for instance, to house determination calibrators and controls and certain samples, such as emergency samples that need to be processed immediately. In an exemplary embodiment, the carousel 189 may be a 2 or 3 part injection molded polymeric (ABS, GE-Cycca or the like) article constructed substantially similar to a TDx® unit dose carousel, an IMx Select® carousel (Abbott Laboratories, Abbott Park, Ill.) and the like.

In some instances, the retention member 156 may not retain the carrier 150 for sample access, but may allow the carrier 150 to move toward an end 158 of the conveyor 146 towards another process path 10. In this case, the frame 148 includes a connecting structure 160 for operatively coupling one process path 10 to another, or more specifically, one frame 148 holding one process path 10 to another frame 148 holding another process path 10. In an exemplary embodiment, the connecting structure 160 may be constructed such that two adjacent frames 148 are offset by a distance substantially within the range of about 0.25 inches to about 1.5 inches.

The connecting structure 160 comprises a first bracket 162 and a second bracket 164. The first bracket 162 is connected with one frame 148 and the second bracket 164 is connected with the another frame 148. To connect the frames 148, a fastener, such as a bolt and the like, is placed between aligned apertures 166 in the first and second brackets 162 and 164. Another fastener is inserted into slots 168 disposed on opposite ends of the brackets 162 and 164. The conveyors 146 supported by both frames 148 have sufficient tolerance such that more precise alignment of the frames 148 is not required. As a carrier 150 leaves an end 158 of one conveyor 146, the carrier 150 is supported by an opposing end 196 of an the adjacent conveyor 146. Once the carrier 150 reaches the end 158 of the last conveyor 146, the carrier 150 is moved to an unload track 192 (FIG. 29), constructed and operated substantially similarly to the load track 142, by another transfer mechanism 197, which may be substantially similar to the transfer mechanism 154.

The construction of the process path 10 is also adaptable in other ways to meet other requirements. For example, it may be desirable to provide a process path 10 that performs 100, 50 or any desired number of determination per hour. Viewing this requirement in another way, it may be desirable to provide a process path 10 that fits within a certain physical space, such as a table surface. To meet such requirements, the process path 10 may be scaled, i.e. altered in size or determinations per hour while still including elements discussed above, such as a bypass region, a mixing device, a pipetting system, a wash station and a reader.

Figure 20A:
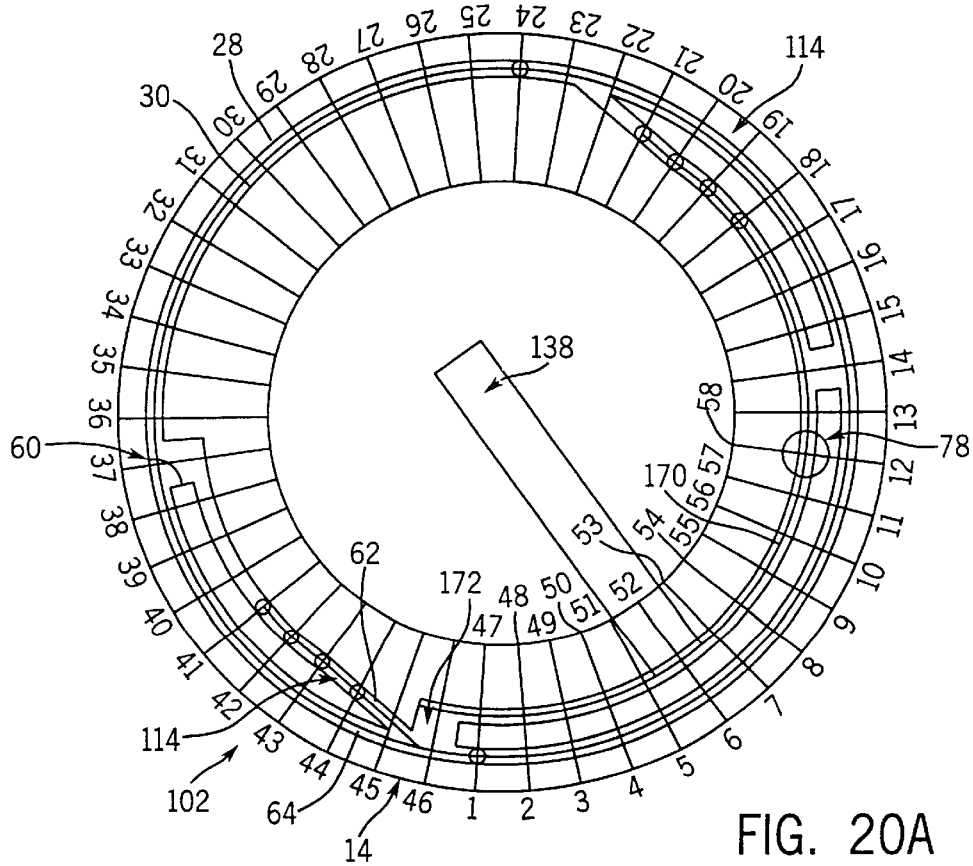
FIGS. 20A and 20B are generic views of other related analyzers having oppositely directed components substantially similar to the component of FIG. 1.
Figure 23A:
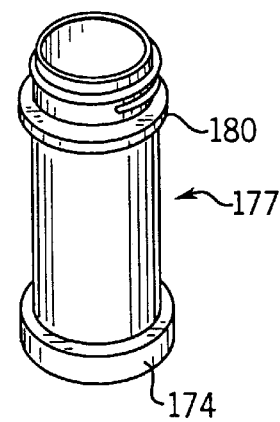
FIGS. 23A, 23B and 23C show another container for use with the process path of FIG. 1.
Figure 23B:
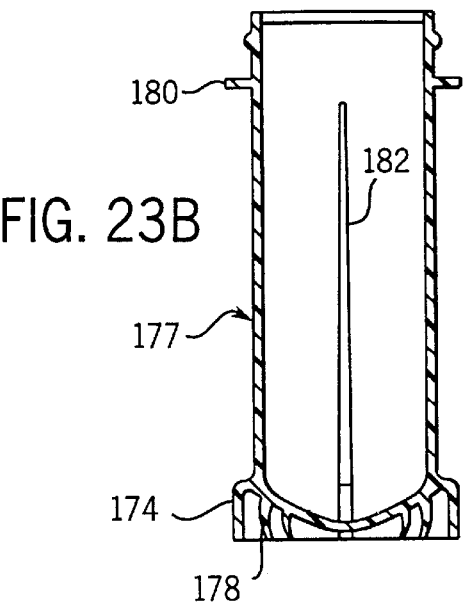
Figure 23C:
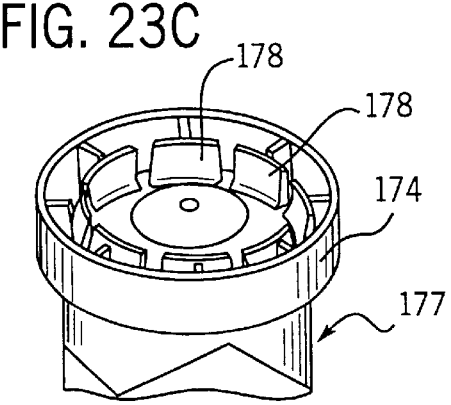

Another embodiment is a process path 10-~, constructed to perform 100 determinations per hour, and is illustrated in FIGS. 20A and 23B. This embodiment utilizes elements substantially similar to those described above, hence the like reference characters. The same index period and assay formats are used, thereby allowing the same reagents to be used. Because of the reduced number of determinations per hour, it is possible to reduce correspondingly the physical dimensions of the embodiment. For instance, whereas the process path 10 of the previous Figures comprises 112 positions, the process path 10-~ comprises about 55 positions. In another embodiment, which performs 50 determinations per hour, the corresponding process path comprises approximately 32 positions.

Whereas the determinations performed with the process path 10 are completed without a container 15 passing the same location along the process lane 28 more than once, the containers 15 used with the process path 10-~ may pass the same location along the process lane 28 more than once. Depending upon the particular needs to be addressed, the process path may be modified such that a container 15 passes the same location along the process path any appropriate number or times. Of course, depending upon the particular employment, a given container 15 may be positioned in a different one of a performance lane 62 and an avoidance lane 64 of a given bypass region 58 at different times passing through the same bypass region 53 during a given determination.

Illustrating further by example, the following describes the procedures performed at each location along the process path 10-~ which performs 100 determinations in an hour. As noted above, a particular container 15 may pass a given location along the process path 10-~ more than once. Therefore, Process Position 1 indicates the first time the container 15 encounters Process Position 1, while Process Position 1' indicates the second time the container 15 encounters Process Position 1. Also, in similar fashion, Process Position 1" indicates the third time the container 15 encounters Process Position 1. Furthermore, the process path 10-~ is constructed such that once a container 15 reaches Process Position 46 a first time, the next Process Position reached by the container 15 may be Process Position 1', i.e. the container 15 moves from one end of the process path 10-~ to an opposite end of the process path 10-~.

In the illustrated embodiment of the process path 10-~, a second processing lane 170 is included. The second processing lane 170 may be located in any suitable position with respect to the processing lane 28 so that a container 15 can move between the process lane 28 and the process lane 170. In some embodiments, the position of the process lane 170 may be chosen to maintain the process path 10-~ within specified physical dimensions.

A prime mover, which may be substantially similar to the prime movers discussed earlier, is located, in an exemplary embodiment, adjacent position 46 along the process lane 28. This prime mover is operable to move a container 15 from the process lane 28 to the process lane 170 when desired, viz. for reading a determination reaction, removal of a container 15 from the process path 10-~, etc. The process lane 28 may be joined to the process lane 170 by suitable connection structures 172, such as those associated with a bypass region. In this manner, a container 15 may be selectively automatically moved between the process lane 28 and the process lane 170. Thus, upon reaching Process Position 46, a container 15 may move to Process Position 1 of the process lane 28, or, alternatively, may move from Process Position 46 of the process lane 28 to Process Positions 47 through 55 of the process lane 170. Once in the process lane 170, process steps detailed in the example below are performed. Of course, structures, similar to those discussed above, that perform those process steps are disposed along the process lane 170 which has sufficient dimensions to accommodate these structures.

| Process Position | Process Step | Description |
|---|---|---|
| 1 | Container 15 load | Container 15 moved from loading lane 30, if present, to process lane 28 as required |
| 1 | Sample Pipettor | Sample deposited into container 15 by pipetting system 128. The sample may be obtained from position 130A or 130B which are located on appropriate conveyors |
| 2 | Reagent Pipettor 1 | Reagent obtained from reagent carousel 131 deposited into container 15 by pipetting system 132 |
| 3 | Mixer | Contents of container 15 are mixed by a device 86 imparting motion to the container 15 |
| 4–16 | Incubation | Contents of container 15 are incubated at a controlled temperature, about 37 degrees Celsius |
| 17 | Bypass region start | Container 15 is selectively positioned at entry to performance lane 62 or avoidance lane 64 of bypass region |
| 18 | Wash zone 1 | Container 15 in performance lane 62 undergoes magnetic separation and fluid addition |
| 19 | Wash zone 1 | Container 15 in performance lane 62 undergoes magnetic separation, container 15 contents aspiration and fluid addition |
| 20 | Wash zone 1 | Container 15 in performance lane 62 undergoes magnetic separation, container 15 contents aspiration and fluid addition |
| 21 | Wash zone 1 | Container 15 in performance lane 62 undergoes magnetic separation, and container 15 contents aspiration |
| 22 | Bypass region end | Performance and avoidance lanes 62 and 64 of bypass region merge |
| 23–24 | Incubation | Contents of container 15 are incubated at a controlled temperature |
| 24 | Sample Pipettor | Sample may be aspirated from container 15 by pipetting system 128 for deposition into a second container 15 at position 1 |
| 25 | Reagent Pipettor 2 | Reagent obtained from reagent carousel 131 may be deposited into container by pipetting system 132 |
| 26 | Mixer | Contents of container 15 are mixed by a device 86 imparting motion to the container 15 |
| 27–39 | Incubation | Contents of container 15 are incubated at a controlled temperature |
| 40 | Bypass region start | Container 15 is selectively positioned at entry to performance lane 62 or avoidance lane 64 of bypass region |
| 41 | Wash zone 2 | Container 15 in performance lane 62 undergoes magnetic separation and fluid addition |
| 42 | Wash zone 2 | Container 15 in performance lane 62 undergoes magnetic separation, container 15 contents aspiration and fluid addition |
| 43 | Wash zone 2 | Container 15 in performance lane 62 undergoes magnetic separation, container 15 aspiration and fluid addition |

-continued

| Process Position | Process Step | Description |
|---|---|---|
| 44 | Wash zone 2 | Container 15 in performance lane 62 undergoes magnetic separation and container 15 contents aspiration |
| 45.5 | Bypass region end | Performance lane 62 and avoidance lane 64 of bypass region merge (midway between positions 45 and 46) |
| 46 | Process lane transfer | Container moves from Process Position 46' of process lane 28 to Process Position 46 of process lane 170 |
| 46–47 | Incubation | Contents of container 15 are incubated at a controlled temperature |
| 48 | Pre-Trigger and Mixer | Reagent added to container 15 and mechanically mixed |
| 49–53 | Incubation | Contents of container 15 are incubated at controlled temperature |
| 52 | Shutter, reader, and trigger | Indicator reaction (such as chemiluminescent reaction) triggered and read with magnetic particles pulled out of solution with magnet. Shutter blocks light. |
| 54 | Liquid Waste Aspirate | Magnetic particles are held at a wall of the container 15 and all liquid in container 15 is aspirated and discarded |
| 55 | Container 15 unload | Container 15 removed from process lane 28 |

Given these modifications, it is possible to utilize determination formats that are substantially similar to those discussed previously. For the sake of clarity, those formats, as performed by the process path 10--~, are listed below.

| Format A | |
|---|---|
| Step | Position |
| Sample introduction | 1 |
| First reagent introduction and mixing | 2–3 |
| First incubation (18 minutes) | 4–17 |
| Container 15 passes through bypass region, first incubation continues | 18–21 |
| First incubation continues | 22–40 |
| Container 15 passes through bypass region, first incubation continues | 41–44 |
| First incubation continues | 45–17' |
| Separation and wash | 18'–21' |
| Second reagent introduction and mixing | 25'–26' |
| Second incubation (4 minutes) | 27'–40' |
| Separation and wash | 41'–44' |
| Container 15 transferred from process lane 28 to process lane 170 | 46' of 28 to 46 of 170 |
| Pretrigger in introduction and mixing | 48 |
| Third incubation (1 minute) | 49–51 |
| Trigger and read | 52 |
| Container 15 evacuate | 54 |
| Container 15 removal | 55 |

As an example, Format A may be used to Determine at least the following items of interest: antibodies to HCV, antibodies to HIV 1/HIV 2, antibodies to hepatitis B core antigen (HBcAb), carcinoembryonic antigen (CEA), cancer antigen 19-9 (CA19-9), Hepatitis B Surface Antigen (HBsAg), antibodies to Hepatitis B Surface antigen (HBsAb), alpha-fetoprotein (AFP), Total prostate specific antigen, (Total PSA), Free PSA, Thyroid stimulating Hormone (TSH), luteinizing hormone (LH), follicle stimulating hormone (FSH), beta human chorionic gonadotropin (B-hCG), Free Thyroxine (Free T4), Free triiodothyronine (Free T3), Total T4, Total T3, Prolactin and Ferritin. It is to be noted that almost any item of interest discussed herein ray be determined by properly using this format. For instance, this format may also be used to determine beta human chorionic gonadotropin (B-hCG), prolactin and ferritin.

| Format B | |
|---|---|
| Step | Position |
| Sample introduction | 1 |
| First reagent introduction and mixing | 2–3 |
| First incubation (11 minutes) | 4–40 |
| Separation and wash | 41–44 |
| Second reagent introduction and mixing | 2'–3' |
| Second incubation (11 minutes) | 4'–40' |
| Separation and wash | 41'–44' |
| Container 15 transferred from process lane 28 to process lane 170 | 46' of 28 to 46 of 170 |
| Pretrigger introduction and mixing | 48 |
| Third incubation (1 minute) | 49–51 |
| Trigger and read | 52 |
| Container 15 evacuate | 54 |
| Container 15 removal | 55 |

As an example, Format B may be used to determine an item of interest in a sample where a relatively increased degree of sensitivity, as compared wish some other formats, is desired. It is to be noted that almost any item of interest discussed herein may be determined by properly using this format.

| Format C | |
|---|---|
| Step | Position |
| Sample introduction | 1 |
| First reagent introduction and mixing | 2–3 |
| First incubation (11 minutes) | 4–40 |
| Separation and wash | 41–44 |
| Second reagent introduction and mixing | 2'–3' |
| Second incubation (4 minutes) | 4'–17' |
| Separation and wash | 18'–21' |
| Third reagent introduction and mixing | 25'–26' |
| Third incubation (4 minutes) | 27'–40' |
| Separation and wash | 41'–44' |
| Container 15 transferred from process lane 28 to process lane 170 | 46' of 28 to 46 of 170 |
| Pretrigger introduction and mixing | 48 |
| Fourth incubation (1 minute) | 49–51 |
| Trigger and read | 52 |
| Container 15 evacuate | 54 |
| Container 15 removal | 55 |

As an example, Format C may be used when the item of interest relates to hepatitis, such as determinations for anti-M, HBcAb-M and HAVAb-M.

Format D

| Step | Position |
|---|---|
| Sample introduction | 1 |
| First reagent introduction and mixing | 2–3 |
| First incubation (6 minutes) | 4–17 |
| Transfer to second container 15 in position 1 | 24 |
| Second reagent introduction and mixing | 2–3 |
| Second incubation (11 minutes) | 4–40 |
| Separation and wash | 41–44 |
| Third reagent introduction and mixing | 2'–3' |
| Third incubation (4 minutes) | 4'–17' |
| Separation and wash | 18'–21' |
| Fourth reagent introduction and mixing | 24'–25' |
| Fourth incubation (4 minutes) | 27'–40' |
| Separation and wash | 41'–44' |
| Container transferred from process lane 28 to process lane 170 | 46' of 28 to 46 of 170 |
| Pretrigger introduction and mixing | 48 |
| Fifth incubation (1 minute) | 49–51 |
| Trigger and read | 52 |
| Container 15 evacuate | 54 |
| Container 15 removal | 55 |

Format E

| Step | Position |
|---|---|
| Sample introduction | 1 |
| First reagent introduction and mixing | 2–3 |
| First incubation (7 minutes) | 4–23 |
| Transfer portion of container 15 contents to second container 15, remainder of container 15 continues on process lane 28 | 24 |
| First container 15 contents continues first incubation (11 minutes) | 25–17' |
| Second reagent introduction and mixing with second container 15 contents | 2–3' |
| First container 15 passes through bypass region 58B | 18'–21' |
| Second container 15 first incubation (18 minutes) | 4–17 |
| Introduction of fourth reagent into first container 15 and mixing (optional, enhances total Hb chemiluminescent signal) | 24'–25' |
| Second container separation and wash | 18'–21' |
| Fourth incubation (4 minutes — optional) of first container 15 | 26'–40' |
| Third reagent introduction into second | 24'–25' |

Format E -continued

| Step | Position |
|---|---|
| container 15 and mixing | |
| First container 15 passes through bypass region | 41'–44' |
| Third incubation (4 minutes) of second container 15 | 26'–40' |
| First container 15 transferred from process lane 28 to process lane 170 | 46' of 28 to 46 of 170 |
| Pretrigger introduction into first container 15 and mixing | 48 |
| Separation and wash of second container 15 | 41'–44' |
| Second container 15 transferred from process lane 28 to process lane 170 | 46' of 28 to 46 of 170 |
| Trigger and read value 1 (Total Hb) from first container 15 | 52 |
| Pretrigger introduction into second container 15 and mixing | 48 |
| Trigger and read value 2 (GlyHb) | 52 |

$$\text{Reported result} = \frac{\text{value 2}}{\text{value 1}} \times 100$$

For example, in Format E, it is possible to modify the format by disregarding the first container 15 after the portion of the container 15 contents has been transferred (Position 24) to the second container 15. In that case, Format E may be used to (determine, for example, folate and vitamin B12.

Format F

| Step | Position |
|---|---|
| Sample introduction | 1 |
| First reagent introduction and mixing | 2–3 |
| First incubation (7 minutes) | 4–24 |
| Transfer portion of container 15 contents to second container 15, remainder of container 15 continues on process lane 28 | 24 |
| First container 15 contents continues first incubation (11 minutes) | 25–17' |
| Second reagent introduction and mixing with second container 15 contents | 2–3 |
| First container 15 passes through bypass region 58B | 18'–21' |
| Second container 15 first incubation (11 minutes) | 4–40 |
| Introduction of fourth reagent into first container 15 and mixing (optional, enhances total Hb chemiluminescent | 24'–25' |

| Format F (continued) | |
|---|---|
| Step | Position |
| signal) Second container separation and wash | 41–44 |
| Fourth incubation (4 minutes - optional) of first container 15 | 26'–40' |
| Third reagent introduction into second container 15 and mixing | 2'–3' |
| First container 15 passes through bypass region | 41'–44' |
| Third incubation (11 minutes) of second container 15 | 4'–40' |
| First container 15 transferred from process lane 28 to process lane 170 | 46' of 28 to 46 of 170 |
| Pretrigger introduction into first container 15 and mixing | 48 |
| Separation and wash of second container 15 | 41'–44' |
| Trigger and read value 1 (Total Hb) from first container 15 | 52 |
| Second container 15 transferred from process lane 23 to process lane 170 | 46' of 28 to 46 of 170 |
| Pretrigger introduction into second container 15 | 48 |
| Trigger and read value 2 (GlyHb) | 52 |

Reported result = $\frac{\text{value 2}}{\text{value 1}} \times 100$

This format may be used, for example, to determine at least one of total and glycated hemoglobin. Also, this format may be modified by disregarding the first container 15 as in Format E.

| Format G | |
|---|---|
| Step | Position |
| Sample introduction | 1 |
| First reagent introduction and mixing | 2–3 |
| First incubation (6 minutes) | 4–23 |
| Transfer portion of container 15 contents to second container 15, remainder of container 15 continues on process lane 28 | 23 |
| First container 15 contents continues first incubation (12 minutes) | 25–17' |
| Second reagent introduction and mixing with second container 15 contents | 2–3 |
| First container 15 separation and wash | 18'–21' |
| Second container 15 first incubation (18 minutes) | 4–17' |
| Introduction of fourth | 24'–25' |

| Format G (continued) | |
|---|---|
| Step | Position |
| reagent into first container 15 and mixing (optional, enhances total Hb chemiluminescent signal) | |
| Second container separation and wash | 18'–21' |
| Fourth Incubation (4 minutes - optional) of first container 15 | 27'–40' |
| Third reagent introduction into second container 15 and mixing | 24'–26' |
| First container 15 separation and wash | 41'–44' |
| Third incubation (4 minutes) of second container 15 | 26'–40' |
| First container 15 transferred from process lane 28 to process lane 170 | 46' of 28 to 46 of 170 |
| Pretrigger introduction into first container 15 and mixing | 48 |
| Separation and wash of second container 15 | 41'–44' |
| Second container 15 transferred from process lane 28 to process lane 170 | 46' of 28 to 46 of 170 |
| Trigger and read value 1 (Total Hb) from first container 15 | 52 |
| Pretrigger introduction into second container 15 and mixing | 48 |
| Trigger and read value 2 (GlyHb) | 52 |

Reported result = $\frac{\text{value 2}}{\text{value 1}} \times 100$

As an example, this format mass also be modified as may be done with Format F. With that modification, this Format may be used to determine progesterone, testosterone and estradiol.

| Format H | |
|---|---|
| Step | Position |
| Sample introduction | 1 |
| First reagent introduction and mixing | 2–3 |
| First incubation | 4–41' |
| Separation and wash | 42'–44' |
| Container 15 transfer from process lane 28 to process lane 170 | 46' of 28 to 46 of 170 |
| Pretrigger introduction and mixing | 48 |
| Second incubation | 49–51 |
| Trigger and read | 52 |

As an example, this format may be used to determine, among other things, beta human chorionic gonadotropin (B-hCG), prolactin, progesterone, testosterone, estradiol and ferritin. It is to be noted that almost any item of interest discussed herein may be determined by properly using this format.

Format I

| Step | Position |
| --- | --- |
| Sample introduction into first container 15, possibly with diluent fluid | 1 |
| First reagent introduction into first container 15, portion of first container 15 contents moved into pipettor, remainder of container continues on process lane 28, bypassing all wash stations, to Position 25' | 2 |
| First reagent introduction into second container 15 and mixing | 2–3 |
| Second container 15 first incubation (18 minutes) | 4–17' |
| Introduction of second reagent into first container 15 and mixing (optional, enhances total Hb chemiluminescent signal) | 25'–26' |
| Second container separation and wash | 18'–21' |
| Fourth incubation (4 minutes - optional) of first container 15 | 27'–40' |
| Third reagent introduction into second container 15 and mixing | 25'–26' |
| First container 15 passes through bypass region 58 | 41'–44' |
| Third incubation (4 minutes) of second container 15 | 27'–40' |
| Pretrigger introduction into first container 15 and mixing | 48 |
| Separation and wash of second container 15 | 41'–44' |
| Trigger and read value 1 (Total Hb) from first container 15 | 52 |
| Pretrigger introduction into second container 15 and mixing | 48 |
| Trigger and read value 2 (GlyHb) | 52 |

Reported result = $\frac{\text{value 2}}{\text{value 1}} \times 100$

As an example, in Format I, it is possible to modify the format by disregarding the first container 15 after the portion of the container 15 contents has been transferred (Position 24) to he second container 15. In that case, Format 7 may be used to determine, for example, folate and vitamin B12.

Format J

| Step | Position |
| --- | --- |
| Sample introduction into container 15, possibly with diluent fluid | 1 |
| First reagent introduction and mixing | 2–3 |
| First incubation (27 minutes - two times along process lane 28) | 4–47 |
| Pretrigger introduction and mixing | 48 |
| Second incubation (1 minute) | 49–51 |
| Trigger and read | 52 |

As an example, Format J may be used to determine, among other things, total hemoglobin.

The embodiments described herein also allow for sample pretreatment which may be performed in at least two ways, indicated as Formats K and L. During performance of sample pretreatment, fluid present in the containers 15 indicated may be processed, after they are no longer significant in the pretreatment steps, in any appropriate manner, such as any of the Formats discussed above. Also, as will become clear later on, both Formats K and L are substantially similarly applicable to the other embodiment of the process path 10 discussed below.

Format K

| Step | Position |
| --- | --- |
| Sample introduction into first container 15, possibly with diluent fluid | 1 |
| First reagent introduction and mixing | 2–3 |
| First incubation (6 minutes) | 4–23 |
| Transfer portion of contents of first container 15 to second container 15 in Position 1 | 24 |
| Second reagent introduction to second container 15 and mixing (optional) | 2–3 |
| Transfer portion of contents of second container 15 to third container 15 in Position 1 | 24 |
| Third reagent introduction to third container and mixing (optional) | 2–3 |

As an example, the third container 15 may be processed according to at least one of Formats A (to determine, among other things, folate), B, C, H and J.

Format L

| Step | Position |
| --- | --- |
| Sample introduction into first container 15, possibly with diluent fluid | 1 |
| First reagent introduction and mixing | 2–3 |
| First incubation (7 minutes) | 4–23 |
| Transfer portion of contents of first container 15 to second container 15 in Position 1 | 24 |
| Second reagent introduction to second container 15 and mixing (optional) | 2–3 |

As an example, the second container 15 may be processed according to at least one of Formats A (to determine, among other things, folate, vitamin B12, confirm HBsAg), B, C, H and J.

Another embodiment is a process path 10', substantially similar to the previous embodiment, of the process path 10 is constructed to perform 50 determinations per hour. Elements similar to those described earlier, along with the same index period and assay formats are used, thereby allowing use of the same reagents albeit in an embodiment having relatively smaller physical dimensions. Following the examples discussed above, the following examples relate to this process path 10'. In these examples, it is assumed that only one pipettor is utilized. Also, whereas the previous examples performed determinations while moving a container 15 along the process lane 28 twice, the process path 10' performs determinations while moving a container 15 along the process lane 28 four times. Thus, the second time Process Position 1 is encounter is indicated as 1', the third time as 1" and the four time as 2". However, it is to be noted that more or less movements along the process lane 28 may be employed. Also, the process lane 28 of this embodiment includes 23 Process Positions with Process Position 23 being located adjacent to Process Position 1.

| Process Position | Process Step | Description |
| --- | --- | --- |
| 1 | Container 15 load | Container 15 moved from loading lane 30, if present, to process lane 28 as required |
| 1 | Pipettor | Sample deposited into container 15 by pipetting system |
| 2 | Pipettor | Reagent obtained from reagent carousel 131 deposited into container 15 |
| 3 | Mixer | Contents of container 15 are mixed by a device 86 imparting motion to the container 15 |
| 4–16 | Incubation | Contents of container 15 are incubated at a controlled temperature, about 37 degrees Celsius |
| 17 | Bypass region start | Container 15 is selectively positioned at entry to performance lane 62 or avoidance lane 64 of bypass region |
| 18 | Wash zone 1 | Container 15 in performance lane 62 undergoes magnetic separation and fluid addition |
| 19 | Wash zone 1 | Container 15 in performance lane 62 undergoes magnetic separation, container 15 contents aspiration and fluid addition |
| 20 | Wash zone 1 | Container 15 in performance lane 62 undergoes magnetic separation, container 15 contents aspiration and fluid addition |
| 21 | Wash zone 1 | Container 15 in performance lane 62 undergoes magnetic separation, and container 15 contents aspiration |
| 22 | Bypass region end | Performance and avoidance lanes 62 and 64 of bypass region merge |
| 23 | Process lane transfer | Container 15 selectively transferred from process lane 28 to process lane 170 |
| 24 | Pre-Trigger and Mixer | Reagent added to container 15 and mechanically mixed |
| 26–28 | Incubation | Contents of container 15 are incubated at controlled temperature |
| 29 | Shutter, reader, and trigger | Indicator reaction (such as chemiluminescent reaction) triggered and read with magnetic particles pulled out of solution with magnet. Shutter blocks light. |
| 30–31 | Liquid Waste Aspirate | Magnetic particles are held at a wall of the container 15 and all liquid in container 15 is aspirated and discarded |
| 32 | Container 15 unload | Container 15 removed from process lane 28 |

Given these modifications, it is possible to utilize determination formats that are substantially similar to those discussed previously. For the sake of clarity, those formats, as performed by a process path that performs 50 determinations per hour, are listed below.

Format A

| Step | Position |
| --- | --- |
| Sample introduction | 1 |
| First reagent introduction and mixing | 2–3 |
| First incubation (18 minutes) | 4–17 |
| Container 15 passes through bypass region, first incubation continues | 18–21 |
| First incubation continues | 22–17" |
| Separation and wash | 18"–21" |
| Second reagent introduction and mixing | 2'''–3''' |
| Second incubation (4 minutes) | 4'''–17''' |
| Separation and wash | 18'''–21''' |
| Container 15 transferred from process lane 28 to process lane 170 | 23''' of 28 to 23 of 170 |
| Pretrigger introduction and mixing | 24 |
| Third incubation (1 minute) | 25–28 |
| Trigger and read | 29 |
| Container 15 evacuate | 31 |
| Container 15 removal | 32 |

As an example, Format A may be used to determine at least the following items of interest: antibodies to HCV, antibodies to HIV 1/HIV 2, antibodies to hepatitis B core antigen (HBcAb), carcinoembryonic antigen (CEA), cancer antigen 19-9 (CA19-9), Hepatitis B Surface Antigen (HBsAg), antibodies to Hepatitis B Surface antigen (HBsAb), alpha-fetoprotein (AFP), Total prostate specific antigen (Total PSA), Free PSA, Thyroid stimulating Hormone (TSH), luteinizing hormone (LH), follicle stimulating hormone (FSH), beta human chorionic gonadotropin (B-hCG), Free Thyroxine (Free T4), Free triiodothyronine (Free T3), Total T4, Total T3, Prolactin and Ferritin. It is to be noted that almost any item of interest discussed herein may be determined by properly using this format. For instance, this format may also be used to determine beta human chorionic gonadotropin (B-hCG), prolactin and ferritin.

Format B

| Step | Position |
|---|---|
| Sample introduction | 1 |
| First reagent introduction and mixing | 2–3 |
| First incubation (11 minutes) | 4–17' |
| Separation and wash | 18'–21' |
| Second reagent introduction and mixing | 2"–3" |
| Second incubation (11 minutes) | 4"–17'" |
| Separation and wash | 18'"–21'" |
| Container 15 transferred from process lane 28 to process lane 170 | 23'" of 28 to 23 of 170 |
| Pretrigger introduction and mixing | 25 |
| Third incubation (1 minute) | 26–28 |
| Trigger and read | 29 |
| Container 15 evacuate | 31 |
| Container 15 removal | 32 |

As an example, Format B may be used to determine an item of interest in a sample where a relatively increased degree of sensitvity, as compared with some other formats, is desired. It is to be noted that almost any item of interest discussed herein may be determined by properly using this format.

Format C

| Step | Position |
|---|---|
| Sample introduction | 1 |
| First reagent introduction and mixing | 2–3 |
| First incubation (11 minutes) | 4–17' |
| Separation and wash | 18'–21' |
| Second reagent introduction and mixing | 2"–3" |
| Second incubation (4 minutes) | 4"–17" |
| Separation and wash | 18"–21" |
| Third reagent introduction and mixing | 2'"–3'" |
| Third incubation (4 minutes) | 4'"–17'" |
| Separation and wash | 18'"–21'" |
| Container 15 transferred from process lane 28 to process lane 170 | 23'" of 28 to 23 of 170 |
| Pretrigger introduction and mixing | 25 |
| Fourth incubation (1 minute) | 26–28 |
| Trigger and read | 29 |

-continued

Format C

| Step | Position |
|---|---|
| Container 15 evacuate | 31 |
| Container 15 removal | 32 |

As an example, Format C may be used when the item of interest relates to hepatitis, such as determinations for anti-M, HBcAb-M and HAVAb-M.

Format D

| Step | Position |
|---|---|
| Sample introduction | 1 |
| First reagent introduction and mixing | 2–3 |
| First incubation (4 minutes) | 4–17 |
| Transfer to second container 15 in position 1 | 24 |
| Second reagent introduction and mixing | 2–3 |
| Second incubation (14 minutes) | 4–17' |
| Separation and wash | 18'–21' |
| Third reagent introduction and mixing | 2"–3" |
| Third incubation (4 minutes) | 4"–17" |
| Separation and wash | 18"–21" |
| Fourth reagent introduction and mixing | 2'"–3'" |
| Fourth incubation (4 minutes) | 4'"–17'" |
| Separation and wash | 18'"–21'" |
| Container transferred from process lane 28 to process lane 170 | 23'" of 28 to 23 of 170 |
| Pretrigger introduction and mixing | 25 |
| Fifth incubation (1 minute) | 26–28 |
| Trigger and read | 29 |
| Container 15 evacuate | 31 |
| Container 15 removal | 32 |

Format E

| Step | Position |
|---|---|
| Sample introduction | 1 |
| First reagent introduction and mixing | 2–3 |
| First incubation (7 minutes) | 4–17 |
| Transfer portion of container 15 contents to second container 15, remainder of container 15 continues on process lane 28 | 24 |
| First container 15 contents continues first incubation (11 minutes) | 24–17' |
| Second reagent introduction and mixing with second container 15 contents | 2–3 |
| First container 15 passes through bypass region 58B | 18"–21" |
| Second container 15 first incubation (18 minutes) | 4–17" |
| Introduction of fourth reagent into first | 2'"–3'" |

-continued

| Format E | |
|---|---|
| Step | Position |
| container 15 and mixing (optional, enhances total Hb chemiluminescent signal) | |
| Second container separation and wash | 18'–21' |
| Fourth incubation (4 minutes - optional) of first container 15 | 4'''–17''' |
| Third reagent introducton into second container 15 and mixing | 24'–25' |
| First container 15 passes through bypass region | 18'''–21''' |
| Third incubation (4 minutes) of second container 15 | 4'''–17''' |
| First container 15 transferred from process lane 28 to process lane 170 | 23''' of 28 to 23 of 170 |
| Pretrigger introduction into first container 15 and mixing | 25 |
| Separation and wash of second container 15 | 18'''–21''' |
| Second container 15 transferred from process lane 28 to process lane 170 | 23''' of 28 to 23 of 170 |
| Trigger and read value 1 (Total Hb) from first container 15 | 29 |
| Pretrigger introduction into second container 15 and mixing | 25 |
| Trigger and read value 2 (GlyHb) | 29 |

$$\text{Reported result} = \frac{\text{value 2}}{\text{value 1}} \times 100$$

For example, in Format E, it is possible to modify the format by disregarding the first container 15 after the portion of the container 15 contents has been transferred (Position 24) to the second container 15. In that case, Format E may be used to determine, for example, folate and vitamin B12.

| Format F | |
|---|---|
| Step | Position |
| Sample introduction | 1 |
| First reagent introduction and mixing | 2–3 |
| First incubation (7 minutes) | 4–17 |
| Transfer portion of container 15 contents to second container 15, remainder of container 15 continues on process lane 28 | 23 |
| First container 15 contents continues first incubation (11 minutes) | 23–17'' |
| Second reagent introduction and mixing with second container 15 contents | 2–3 |

-continued

| Format F | |
|---|---|
| Step | Position |
| First container 15 passes through bypass region 58B | 18''–21'' |
| Second container 15 first incubation (11 minutes) | 4–17' |
| Introduction of fourth reagent into first container 15 and mixing (optional, enhances total Hb chemiluminescent signal) | 2'''–3''' |
| Second container separation and wash | 18'–21' |
| Fourth incubation (4 minutes — optional) of first container 15 | 4'''–17''' |
| Third reagent introduction into second container 15 and mixing | 2'''–3''' |
| First container 15 passes through bypass region | 18'''–21''' |
| Third incubation (11 minutes) of second container 15 | 4'''–17''' |
| First container 15 transferred from process lane 28 to process lane 170 | 23''' of 28 to 23 of 170 |
| Pretrigger introduction into first container 15 and mixing | 25 |
| Separation and wash of second container 15 | 18'''–21''' |
| Trigger and read value 1 (Total Hb) from first container 15 | 29 |
| Second container 15 transferred from process lane 28 to process lane 170 | 23''' of 28 to 23 of 170 |
| Pretrigger introduction into second container 15 and mixing | 25 |
| Trigger and read value 2 (GlyHb) | 29 |

$$\text{Reported result} = \frac{\text{value 2}}{\text{value 1}} \times 100$$

This format may be used, for example, to determine at least one of total and glycated hemoglobin. Also, this format may be modified by disregarding the first container 15 as in Format E.

| Format G | |
|---|---|
| Step | Position |
| Sample introduction | 1 |
| First reagent introduction and mixing | 2–3 |
| First incubation (6 minutes) | 4–24 |
| Transfer portion of container 15 contents to second container 15, remainder of container 15 continues on process lane 28 | 23 |
| First container 15 | 24–17'' |

Format G

| Step | Position |
|---|---|
| contents continues first 90 incubation (12 minutes) | |
| Second reagent introduction and mixing with second container 15 contents | 2–3 |
| First container 15 separation and wash | 18"–21" |
| Second container 15 first incubation (18 minutes) | 4–17" |
| Introduction of fourth reagent into first container 15 and mixing (optional, enhances total Hb chemiluminescent signal) | 2'''–3''' |
| Second container setaraton and wash | 18"–21" |
| Fourth incubation (4 minutes - optional) of first container 15 | 4'''–17''' |
| Third reagent introduction into second container 15 and mixing | 2'''–3''' |
| First container 15 separation and wash | 18'''–21''' |
| Third incubation (4 minutes) of second container 15 | 4'''–17''' |
| First container 15 transferred from process lane 28 to process lane 170 | 23''' of 28 to 23 of 170 |
| Pretrigger introduction into first container 15 and mixing | 25 |
| Separation and wash of second container 15 | 18'''–21''' |
| Second container 15 transferred from process lane 28 to process lane 170 | 23''' of 28 to 23''' of 170 |
| Trigger and read value 1 (Total Hb) from first container 15 | 29 |
| Pretrigger introduction into second container 15 and mixing | 25 |
| Trigger and read value 2 (GlyHb) | 29 |

Reported result = $\dfrac{\text{value 2}}{\text{value 1}} \times 100$

As an example, this format may also be modified as may be done with Format F. With that modification, this Format may be used to determine progesterone, testosterone and estradiol.

Format H

| Step | Position |
|---|---|
| Sample introduction | 1 |
| First reagent introduction and mixing | 2–3 |
| First incubation | 4–17''' |
| Separation and wash | 18'''–21''' |
| Container 15 transfer from process lane 28 to process lane 170 | 23''' of 28 to 23 of 170 |
| Pretrigger introduction and mixing | 25 |
| Second incubation | 26–28 |
| Trigger and read | 29 |

As an example, this format may be used to determine, among other things, beta human chorionic gonadotropin (B-hCG), prolactin, progesterone, testosterone, estradiol and ferritin. It is to be noted that almost any item of interest discussed herein may be determined by properly using this format.

Format I

| Step | Position |
|---|---|
| Sample introduction into first container 15, possibly with diluent fluid | 1 |
| First reagent introduction into first container 15, portion of first container 15 contents moved into pipettor, remainder of container continues on process lane 23, bypassing all wash stations, to Position 25' | 2 |
| First reagent introduction into second container 15 and mixing | 2–3 |
| Second container 15 first incubation (18 minutes) | 4–17" |
| Introduction of second reagent into first container 15 and mixing (optional, enhances total Hb chemiluminescent signal) | 2'''–3''' |
| Second container separation and wash | 18'''–21''' |
| Fourth incubation (4 minutes - optional) of first container 15 | 4'''–17''' |
| Third reagent introduction into second container 15 and mixing | 2'''–3''' |
| First container 15 passes through bypass region 53 | 13'''–21''' |
| Third incubation (4 minutes) of second container 15 | 4'''–17''' |
| Pretrigger introduction into first container 15 and mixing | 25 |
| Separation and wash of second container 15 | 18'''–21''' |
| Trigger and read value 1 (Total Hb) from first container 15 | 29 |
| Pretrigger introduction | 25 |

Format I

| Step | Position |
|---|---|
| into second container 15 and mixing | |
| Trigger and read value 2 (GlyHb) | 29 |

Reported result = $\frac{\text{value 2}}{\text{value 1}} \times 100$

As an example, in Format I, it is possible to modify the format by disregarding the first container 15 after the portion of the container 15 contents has been transferred (Position 24) to the second container 15. In that case, Format I may be used to determine, for example, folate and vitamin B12.

Format J

| Step | Position |
|---|---|
| Sample introduction into container 15, possibly with diluent fluid | 1 |
| First reagent introduction and mixing | 2–3 |
| First incubation (27 minutes - four times along process lane 28) | 4–47''' |
| Pretrigger introduction and mixing | 25 |
| Second incubation (1 minute) | 26–28 |
| Trigger and read | 29 |

As an example, Format J may be used to determine, among other things, total hemoglobin.

The embodiments described herein also allow for sample pretreatment which may be performed in at least two ways, indicated as Formats K and L. During performance of sample pretreatment, fluid present in the containers 15 indicated may be processed, after they are no longer significant in the pretreatment steps, in any appropriate manner, such as any of the Formats discussed above. Also, as will become clear later on, both Formats K and L are substantially similarly applicable to the other embodiment of the process path 10 discussed below.

Format K

| Step | Position |
|---|---|
| Sample introduction into first container 15, possibly with diluent fluid | 1 |
| First reagent introduction and mixing | 2–3 |
| First incubation (6 minutes) | 4–23 |
| Transfer portion of contents of first container 15 to second container 15 in position 1 | 24 |
| Second reagent introduction to second container 15 and mixing (optional) | 2–3 |
| Transfer portion of contents of second container 15 to third container 15 in Position 1 | 24 |
| Third reagent introduction to third container and mixing (optional) | 2–3 |

As an example, the third container 15 may be processed according to at least one of Formats A (to determine, among other things, folate), B, C, H and J.

Format L

| Step | Position |
|---|---|
| Sample introduction into first container 15, possibly with diluent fluid | 1 |
| First reagent introduction and mixing | 2–3 |
| First incubation (7 minutes) | 4–23 |
| Transfer portion of contents of first container 15 to second container 15 in position 1 | 24 |
| Second reagent introduction to second container 15 and mixing (optional) | 2–3 |

As an example, the second container 15 may be processed according to at least one of Formats A (to determine, among other things, folate, vitamin B12, confirm HBsAg), B, C, H and J.

Given commonality among the various embodiments of the process path discussed and exemplified above, it is to be appreciated that assay formats performed on each of the various embodiments are essentially the same. The time frames are identical. Reagents for a particular assay used on one of the embodiments may also be used on other embodiments.

Upon consideration of all of these examples and their common features, it is to be understood that the process path 10, or in other words the process lane 28, has a variable physical length. However, the effective length of the process path 10 is constant in all embodiments. This effective length represents the total distance traveled by the container 15 along the process path 10 during performance of a certain determination. The physical length, i.e. the physical dimensions of the process path 10, is variable, for instance, to make the process path 10 fit within a given space. The effective length of the process path 10 is maintained constant by moving the container 15 multiple times along the same process path 10 (4 times in the last set of examples). Maintenance of the effective length is achieved with appropriate combination of selective automatic performance of a given determination process step. In all instances, the effective length remains constant even though the physical length of a given process path 10 may be longer or shorter than other process paths 10.

It is to be noted that all of the above discussed embodiments of the process path 10 include and utilize certain common elements, such as reagents, a sample/reagent pipettor, a mixer, a wash zone and a reader. The structural elements are arranged along each embodiment of the process path 10 such that each embodiment is able to perform the same determinations in substantially the same manner by keeping the effective length of the process path 10 constant. Each of the embodiments of the process path executes determinations with approximately the same number, such as 98 in the above examples, "steps" of the container 15 along the process path 10 between sample introduction and reading. Determination of a given item of interest by one of the embodiments of the process path 10 takes substantially the same amount of time as a determination of the same item or interest by another embodiment of the process path 10. Thus, it is possible to construct a structure for performing item of interest determinations which conforms to desired physical dimensions, throughput requirements, etc., while using the common elements discussed herein by maintaining the effective length of the process path constant.

What is claimed is:

1. A structure for performing a process for determining an item of interest in a sample, the structure comprising:
    (a) a process path, the process path comprising:
        (i) a process lane in which a reaction container is moved, the process lane diverging into
        (ii) a process step performance lane where a process step of a process for determining the item of interest in the sample is performed, and
        (iii) a process step avoidance lane where no process step of the process for determining the item of interest in the sample is performed, the process step performance lane and the process step avoidance lane being disposed substantially side by side, both the process step performance lane and the process step avoidance lane converging to the process lane;
    (b) a first prime mover operatively connected with the process path for moving the reaction container along the process lane, said first prime mover, by itself, being (i) capable of moving the reaction container so as to enable the reaction container to simultaneously pass through the process step performance lane and along side of the process step avoidance lane and being (ii) capable of moving the reaction container so as to enable the reaction container to simultaneously pass along side of the process step performance lane and through the process step avoidance lane;
    (c) a first pipetting system operatively associated with the process step performance lane for introducing the sample to the reaction container moved along the process lane;
    (d) a second pipetting system operatively associated with the process step performance lane for introducing a reagent to the reaction container moved along the process lane;
    (e) a device operatively connected with the process step performance lane and selectively engagable with the reaction container for mixing the sample and the reagent in the reaction container moved along the process lane;
    (f) a second prime mover operatively connected with the process path for selectively positioning the reaction container in the process step performance lane or the process step avoidance lane; and
    (g) a reader operatively connected with the process step performance lane for determining the item of interest in the sample based upon a reaction between the sample and the reagent contained within the reaction container.

2. A structure as defined in claim 1 wherein the process path further comprises:
    (iv) a cover;
    (v) a base connected with the cover; and
    (vi) a disk rotatably disposed between the cover and the base.

3. A structure as defined in claim 2 further comprising a drain duct disposed on at least one of the cover or the base for facilitating removal of fluid from the process path.

4. A structure as defined in claim 2 further comprising a slot disposed on the disk for accepting the reaction container.

5. A structure as defined in claim 4 wherein the slot has a longitudinal axis and wherein the reaction container is movable within the slot along the longitudinal axis.

6. A structure as defined in claim 5 further comprising a third prime mover operatively connected with the process path and engagable with the reaction container for moving the reaction container along the longitudinal axis.

7. A structure as defined in claim 5 wherein the process path further comprises:
    (iv) means for moving the reaction container along the longitudinal axis.

8. A structure as defined in claim 4 wherein the slot has a latitudinally expanded width to facilitate removal of the reaction container from the slot.

9. A structure as defined in claim 1 wherein the process path further comprises:
    (iv) a loading lane for accepting the reaction container from a reaction container supply, the loading lane being operatively connected with the process lane so that the reaction container can move between the loading lane and the process lane.

10. A structure as defined in claim 9 wherein the process path further comprises:
    (v) a passageway operatively connecting the loading lane and the process lane for allowing the reaction container to move from the loading lane to the process lane.

11. A structure as defined in claim 10 further comprising:
    (h) a third prime mover operatively connected with the process path for moving the reaction container through the passageway.

12. A structure as defined in claim 1 further comprising:
    (h) a magnet connected with the process path such that the reaction container moved along the process lane encounters the magnet.

13. A structure as defined in claim 1 further comprising:
    (h) a carousel disposed adjacent the process path for supplying the reagent to the second pipetting system.

14. A structure as defined in claim 1 further comprising:
    (h) a wash station operatively connected with the process path for washing the reaction cuvette moved along the process lane.

15. A structure for performing a process for determining an item of interest in a sample, the structure comprising:
    (a) a process path, the process path comprising:
        (i) a process lane accepting a reaction container, the process lane diverging into
        (ii) a process step performance lane where a process step of a process for determining the item of interest in the sample is performed, and (iii) a process step avoidance lane where no process step of the process for determining the item of interest in the sample is performed, the process step performance lane and the process step avoidance lane being disposed substantially side by side, both the process step performance lane and the process step avoidance lane converging to the process lane;

(iv) a cover;

(v) a base connected with the cover; and (vi) a disk rotatably disposed between the cover and the base, said structure further including, a first prime mover that, by itself, is (i) capable of moving the reaction container so as to enable the reaction container to simultaneously pass through the process step performance lane and along side of the process step avoidance lane and is (ii) capable of moving the reaction container so as to enable the reaction container to simultaneously pass along side of the process step performance lane and through the process step avoidance lane.

16. A structure as defined in claim 15 further comprising:

(b) a prime mover operatively connected with the process path for selectively positioning the reaction container on the process step performance lane or the process step avoidance lane.

17. A structure as defined in claim 15 further comprising a drain duct disposed on at least one of the cover or the base for facilitating removal of fluid from the process path.

18. A structure as defined in claim 17 wherein the disk rotates in a first direction and the drain duct is oriented in the first direction to facilitate removal of fluid from the structure.

19. A structure as defined in claim 15 wherein the process path further comprises a belt movably disposed between the cover and the base, and the process lane is formed on at least one of the cover and the base.

* * * * *